(12) United States Patent
Kim et al.

(10) Patent No.: US 12,282,019 B2
(45) Date of Patent: *Apr. 22, 2025

(54) COMPOSITIONS AND METHODS TO DETECT GASTROINTESTINAL DISEASE

(71) Applicant: The Board of Supervisors of Louisiana State University and Agricultural and Mechanical College, Baton Rouge, LA (US)

(72) Inventors: Sunyoung Kim, New Orleans, LA (US); Zeromeh Gerber, Las Vegas, NV (US); Duna Penn, New Orleans, LA (US); Carl Sabottke, New Orleans, LA (US); Rebecca Buckley, Metairie, LA (US)

(73) Assignee: THE BOARD OF SUPERVISORS OF LOUISIANA STATE UNIVERSITY AND AGRICULTURAL AND MECHANICAL COLLEGE, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/957,853

(22) Filed: Sep. 30, 2022

(65) Prior Publication Data

US 2023/0184769 A1 Jun. 15, 2023

Related U.S. Application Data

(63) Continuation of application No. 16/267,120, filed on Feb. 4, 2019, now Pat. No. 11,493,515, which is a continuation-in-part of application No. PCT/US2017/045588, filed on Aug. 4, 2017.

(60) Provisional application No. 62/524,306, filed on Jun. 23, 2017, provisional application No. 62/467,487, filed on Mar. 6, 2017, provisional application No. 62/378,820, filed on Aug. 24, 2016, provisional application No. 62/371,131, filed on Aug. 4, 2016.

(51) Int. Cl.

| | |
|---|---|
| *G01N 33/53* | (2006.01) |
| *A23K 10/00* | (2016.01) |
| *A23K 20/195* | (2016.01) |
| *A23L 33/00* | (2016.01) |
| *A23L 33/17* | (2016.01) |
| *A61K 35/741* | (2015.01) |
| *A61P 1/00* | (2006.01) |
| *A61P 29/00* | (2006.01) |
| *C07K 16/40* | (2006.01) |
| *C12Q 1/42* | (2006.01) |
| *C12Q 1/68* | (2018.01) |
| *G01N 33/573* | (2006.01) |
| *A61K 9/00* | (2006.01) |

(52) U.S. Cl.
CPC .......... *G01N 33/573* (2013.01); *A23K 10/00* (2016.05); *A23K 20/195* (2016.05); *A23L 33/17* (2016.08); *A23L 33/40* (2016.08); *A61K 35/741* (2013.01); *A61P 1/00* (2018.01); *A61P 29/00* (2018.01); *C07K 16/40* (2013.01); *C12Q 1/42* (2013.01); *C12Q 1/68* (2013.01); *A23V 2002/00* (2013.01); *A61K 9/0019* (2013.01); *A61K 9/0053* (2013.01); *G01N 2333/916* (2013.01); *G01N 2800/065* (2013.01)

(58) Field of Classification Search
CPC .... G01N 33/53; G01N 33/573; G01N 33/543; G01N 2800/065; G01N 2333/916; C07K 16/40

See application file for complete search history.

(56) References Cited

U.S. PATENT DOCUMENTS

| | | | |
|---|---|---|---|
| 5,736,343 A * | 4/1998 | Landry | G01N 33/68 435/7.6 |
| 8,088,591 B2 | 1/2012 | Franzmann et al. | |
| 10,781,470 B2 | 9/2020 | Malo | |
| 11,493,515 B2 * | 11/2022 | Kim | A23K 20/195 |
| 2004/0157306 A1 | 8/2004 | Plowman et al. | |
| 2008/0038759 A1 | 2/2008 | Keren et al. | |
| 2010/0093552 A1 | 4/2010 | Panja | |
| 2011/0142817 A1 * | 6/2011 | Brands | A23L 33/40 424/94.6 |
| 2011/0159527 A1 | 6/2011 | Schlossmacher et al. | |
| 2011/0206654 A1 | 8/2011 | Hodin et al. | |
| 2012/0253771 A1 | 10/2012 | Col et al. | |
| 2014/0162370 A1 | 6/2014 | Ling et al. | |
| 2016/0232324 A1 | 8/2016 | Liu et al. | |

FOREIGN PATENT DOCUMENTS

| | | |
|---|---|---|
| EP | 0274198 | 11/1989 |
| WO | WO2018027179 A1 | 2/2018 |

OTHER PUBLICATIONS

Dvorak et al., Maternal Milk Reduces Severity of Necrotizing Enterocolitis and Increases Intestinal IL-10 in a neonatal rat model, Pediatric Research, vol. 53, No. 3, pp. 426-433. (Year: 2003).*
Whitehouse et al., Association for Academic Surgery The Protective Role of Intestinal Alkaline Phosphatase in Necrotizing Enterocolitis, Journal of Surgical Research, 163, 2010, pp. 79-85. (Year: 2010).*
Schrenkhammer et al., Time-Resolved Fluorescne-Based assay for the Determination of Alkaline Phosphatase Activity and Application to the Screening of its inhibitors, Journal of Biomolecular Screening, 13(1), 2008, pp. 9-16 (Year: 2008).*
Al-Rashida and Iqbal. Inhibition of alkaline phosphatase: an emerging new drug target. Minireviews in Medicinal Chemistry 15, 41-51 (2015).
Amer, M. D. et al. Platelet-activating factor concentration in the stool of human newborns: effects of enteral feeding and neonatal necrotizing enterocolitis. Biol Neonate. 2004; 85:159-66.

(Continued)

*Primary Examiner* — Gary Counts
(74) *Attorney, Agent, or Firm* — Baker, Donelson, Bearman, Caldwell & Berkowitz, PC

(57) ABSTRACT

This invention comprises compositions and methods to detect and treat gastrointestinal diseases.

19 Claims, 41 Drawing Sheets
(37 of 41 Drawing Sheet(s) Filed in Color)

(56) References Cited

OTHER PUBLICATIONS

Ballance, W. A., et al. Pathology of neonatal necrotizing enterocolitis: a ten-year experience. J Pediatr 117, S6-13 (1990).
Bell M J, et al. Neonatal necrotizing enterocolitis. Therapeutic decisions based upon clinical staging. Ann Surg. 1978; 187:1-7.
Biesterveld B E, et al. Intestinal alkaline phosphatase to treat necrotizing enterocolitis. J Surg Res. 2015; 196:235-40.
Bobkova, E. V. et al. Modulators of intestinal alkaline phosphatase. Phosphatase Modulators. Humana Press, Totowa, NJ, 2013. 135-144.
Borgers M. The cytochemical application of new potent inhibitors of alkaline phosphatases. Journal of Histochemistry & Cytochemistry 21, 812-824 (1973).
Cetinkaya, M. et al. Comparison of the efficacy of serum amyloid A, C-reactive protein, and procalcitonin in the diagnosis and follow-up of necrotizing enterocolitis in premature infants. J. Pediatr Surg. 2011; 46:1482-9.
Chu A, Hageman J R, Caplan M S. Necrotizing enterocolitis: predictive markers and preventive strategies. NeoReviews. 2013; 14:e113-e20.
Coursey C A, Hollingsworth C L, Wriston C, Beam C, Rice H, Bisset G, 3rd. Radiographic predictors of disease severity in neomates and infants with necrotizing enterocolitis. AJR Am J Roentgenol. 2009; 193:1408-13.
Dictionary of Pharmacy, Dennis B. Worthen (ed.), published by Haworth Press, Inc.(2004).
Eliakin, R. et al. Rat intestinal alkaline phosphatase secretion into lumen and serum is coordinately regulated. Biochim Biophys Acta. 1091:1-8 (1991).
Evennett, N. et al. Smooth muscle actin as a novel serologic marker of severe intestinal damage in rat intestinal ischemia-reperfusion and human necrotizing enterofolitis. J Surg Res. 2014; 191:323-30 (2014).
Fawley, Jr. & Gourlay, D. M. Intestinal alkaline phosphatase: a summary of its role in clinical disease. J Surg Res 202, 225-234, doi:10.1016/j.jss.201.12.008 (2016).
Fitzbiggons, S. C. et al. Mortality of necrotizing enterocolitis expressed by birth weight categories. J. Pediatr Surg. 44:1072-6 (2009).
Goldberg, R F. et al. Intesttinal alkaline phosphatase is a gut mucosal defense factor maintained by enteral nutrition. Proc Natl Acad Sci USA. 2008; 105:3551-6 (2008).
Gonzalez-Rivera, R. et al. The age of necrotizing enterocolitis onset: an application of Sartwell's incubation period model. J. Perinat. 31:519-23 (2011).
Group YICSS. Clinical signs that predict severe illness in children under age 2 months: a multi-centre study. The lancet. 371:135-42 (2008).
Heinzerling, N.P. et al. Intestinal alkaline phosphatase is protective to the preterm rat pup intestine. Pediatr Surg. 49:954-60 (2014).
Horrigan, F.D. & Danovitch, S. H. The origin of human fecal alkaline phosphatase. Am J Dig Dis 19,603-608 (1974).
International Search Report for PCT/US2017/045588 mailed Nov. 6, 2017, 2 pages.
International Search Report for PCT/US2020/16646 mailed Apr. 30, 2020, 2 pages.
Ji, J, et al. A data-driven algorithm integrating clinical and laboratory features for the diagnosis ands prognosis of necrotizing enterocolitis. PLoS One. 2014; 9:e89860.
Jiminez, J.A. et al. Animal models to study acute and chronic intestinal inflammation in mammals. Gut Pathog, 7:29. doi: 10.1186/s13099-015-0076-y, 31 pages (2015).
Kamkpanatkosol, R. et al. The relationship between reticulated platelets, intestinal alkaline phosphatase, and necrotizing enterocolitis. J Pediatr Surg 49, 273-276, doi:10.1016/j.jpedsurg.2013.11.037 (2014).
Klemperer, Friedrich W., Joseph M. Miller, and Caroline J. Hill. "The inhibition of alkaline phosphatase by beryllium." Journal of Biological Chemistry 180.1 (1949): 281-8.

Knight et al. Non-invasive analysis of intestinal development in preterm and term infants using RNA-sequencing. 2014. Scientific Reports 4, 5453.
Kosloske A M, Musemeche C A, Ball WS, Jr., Ablin D S, Bhattacharyya N. Necrotizing enterocolitis: value of radiographic findings to predict outcome. AJR A J Roentgenol. 1988; 151:771-4.
Lalles J P. Luminal ATP: the missing link between intestinal alkaline phosphatase, the gut microbiota, and inflammation? Am J Physiol Gastrointest Liver Pysiol. 2014; 2306:G824-5.
Lehmann, F. G., Hufnagel, H. & Lorenz-Meyer, H. Fecal intestinal alkaline phosphatase: a parameter for toxic damage of the small intestinal mucosa. Digestion 21, 156-162 (1981).
Lichtman J S, et al. Host-centric proteomics of stool: a novel strategy focused on intestinal responses to the gut microbiota. Mol Cell Proteomics. 2013; 12:3310-8.
Malo, M. S. A high level of intestinal alkaline phosphatase is protective against type 2 diabetes mellitus irrespective of obesity. EBioMedicine. 2015; 2:2016-23.
Malo, M. S. et al. Intestinal alkaline phosphatase preserves the normal homeostasis of gut microbiota. Gut 59, 1476-1484, doi:10.1136/gut.2010.211706 (2010).
Malo, M.S. et al. Intestinal alkaline phosphatase promotes gut bacterial growth by reducing the concentration of luminal nucleotide triphosphates. Am J Physiol Gastrointest Liver Physiol 306, G826-838, doi: 10.1152/ajpgi.00357.2013 (2014).
McFarland, L. V. Alternative treatments for Clostridium difficile disease: what really works? J. Medic. Microbiol. 2005, 54:101-111.
McLachlan, R. et al. Plasma intestinal alkaline phosphatase isoenzymes in neonates with bowel necrosis. J. Clin Pathol 46, 654-659 (1993).
Molnar, K, et al. Decreased mucosal expression of intestinal alkaline phosphatase in children with coeliac disease. Virchows Arch, 460(2):157-61 (2012).
Molnár, Kriszta, et al. Intestinal alkaline phosphatase in the colonic mucosa of children with inflammatory bowel disease. World journal of gastroenterology: WJG 18.25 (2012): 3254-3259.
Moussa, R. et al. Fecal calprotectin levels in preterm infants with and without feeding intolerance. J. Pediatr (Rio J). 2016; 92(5): 486-482.
Mulivor, R. A., Hannig, V.L. & Harris, H. Developmental change in human intestinal alkaline phosphatase. Proc Natl Acad Sci USA 75, 3909-3912 (1978).
Narisawa et al. Novel inhibitors of alkaline phosphatase suppress vascular smooth muscle cell calcification. Journal of Bone and Mineral Research 22, 1700-1710, 2007.
Neal, et al. Discovery and validation of a new class of small molecule Toll-like receptor 4 (TLR4) inhibitors. PloS One 12, e65779, 11 pages (2013).
Neu, J. & Walker, W. A. Necrotizing enterocolitis. N Engl J Med 364, 255-264, doi: 10.1056/NEJMra1005408 (2011).
Ng, P. C. et al. Host-response biomarkers for diagnosis of late-onset septicemia and necrotizing enterocolitis in preterm infants. J. Clin Invest. 2010; 120:2989-3000.
Ng, P. C. et al. The use of laboratory biomarkers for surveillance, diagnosis and prediction of clinical outcomes in neonatal sepsis and necrotizing enterocolitis. Arch Dis Child Fetal Neonatal Ed. 2015; 100:F448-52.
Ng, P.C. et al. Biomarkers for prediction and diagnosis of necrotizing enterocolitis. Clin Perinatol 40, 149-159, doi:101016/j.clp.2012.12.005 (2013).
Park, S.-Y. et al. Expression of intestinal alkaline phosphatase (IAP) in patients with inflammatory bowel disease. United European Gastroent. Journal, vol. 3, issue 5, abstract A417 (2015).
Patel, R. M. et al., for the Eunice Kennedy Shriver National Institute of Child Health and Human Development Neonatal Research Network. Causes and timing of death in extremely premature infants from 2000 through 2011. N Engl J Med. 2015: 372-331-40.
Pedregosa, F. et al. Scikit-learn: Machine learning in Python. J. Machine Learning Research 2011; 12:2825-30.
Porstmann, B. et al. Which of the commonly used marker enzymes gives the best results in colorimetric and fluorimetric enzyme immunoassays: horseradish peroxidase, alkaline phosphatase or bets-galactosidase? J Immunl Methods 79, 27-37 (1985).

(56) References Cited

OTHER PUBLICATIONS

Pourcyrous, M. et al. C-reactive protein in the diagnosis, management, and prognosis of neonatal necrotizing enterocolitis. Pediatrics. 2005; 116:1064-9.

Rabinowitz, S. S. et al. Platelet-activating factor in infants at risk for necrotizing enterocolitis. J Pediatr. 2001; 138:81-6.

Rentea, R. M. et al. Intestinal alkaline phosphatase administration in newborns is protective of gut barrier function in a neonatal necrotizing, enterocolitis rat model. J Pediatr Surg. 2012; 47:1135-42.

Riggle, K M, et al. Intestinal alkaline phosphatase prevents the systemic inflammatory response associated with necrotizing enterocolitis. J Surg Res. 2013; 180:21-6.

Rish, I. An empirical study of the naïve Bayes classifier. IJCAI 2001 workshop on empirical methods in artificial intelligence: IBM New York; 2001, pp. 41-46.

Shifrin, D A, Jr. et al. Enterocyte microvillus-derivee vesicles detoxify bacterial products and regulate epithelial-microbial interactions. Curr Biol. 2012; 22:627-31.

Shulman, R J, Buffone G, Wise L. Enteric protein loss in necrotizing enterocolitis as measured by fecal alpha 1-antitrypsin excretion. J Pediatr. 1985; 107:287-9.

Sisley, A. C. et al. Decrease in mucosal alkaline phosphatase: a potential marker of intestinal reperfusion injury. J Lab Clin Med. 1999; 133:335-41.

Stedman's Medical Dictionary for the Health Professions and Nursing, 5th ed (illustrated), Lippincott Williams & Wilkins (2005).

Strongin, W. Sensitivity, Specificity and Predictive Value of Diagnostic Tests: Definitions and Clinical Applications. Chapter 10 from Laboratory Diagnosis of Viral Infections, Lennette (ed.), Marcel Dekker, Inc. New Yorks, pp. 211-219 (1992).

Swittink, R. D. et al. 2017. Metaproteomics reveals functional differences in intestinal microbiota development of pretem infants. Molecular & Cellular Proteomics. DOI: 10.1074/mcp. RA117.000102, 29 pages.

Sylvester, K.G. et al. A novel urine peptide biomarker0based algorithm for the prognosis of necrotizing enterocolitis in human infants. Gut. 2014; 63:1284-92.

Sylvester. K. G. et al. Urine protein biomarkers for the diagnosis and prognosis of necrotizing enterocolitis in infants. J. Pediatr. 2014; 164:607-12 e1-7.

Tam A L, Camberos A, Applebaum H. Surgical decision making in necrotizing enterocolitis and focal intestinal perforation: predictive value of radiologic findings. J Pediatr Surg. 2002; 37:1688-91.

Tayman, C. et al. C5a, a complement activation product, is a useful marker in predicting the severity of necrotizing enterocolitis. Tohoku J Exp Med. 2011; 224:143-50.

Thomas D W, Henton D H. The use of fecal alkaline phosphatase as an indicator of intestinal damage. Digestion. 1985; 31:82-8.

Torzewski, M. et al. Animal models of C-reactive protein. Mediators Inflamm, vol. 2014, pp. 1-7 (2014).

Tuin, A. et al. Role of alkaline phosphatase in colitis in manand rats. Gut. 2009; 58:379-87.

Uauy, R. D. et al. Necrotizing enterocolitis in very low birth weight infants: biodemographic and clinical correlates. National Institute of Child Health and Human Development Neonatal Research Network. J Pediatr 119, 630-638 (1991).

Van Der Vekens, N. et al. Human and equine cardiovascular endocrinology: beware to compare. Cardiovascular Endocrinology 2(4): p. 67-76 (2013).

Vockley, J. et al. Differentiation of human adult and fetal intestinal alkalike phosphatases with monoclonal antibodies. Am J. Hum Genet 36, 987-1000 (1984).

Written Opinion for PCT/US2017/045588 mailed Nov. 6, 2017, 5 pages.

Written Opinion for PCT/US2020/16646 mailed Apr. 30, 2020, 4 pages.

Yang, Q. et al. Dynamic change of fecal calprotectin in very low birth weight infants during the first month of life. Neonatology. 2008; 94:267-71.

Yazji, I. et al. Endothelial TLR4 activation impairs intestinal microcirculatory perfusion in necrotizing enterocolitis via eNOS-NO-nitrite signaling. Proceedings of the National Academy of Science USA 110, 9451-9456 (2013).

Yee, W. H. et al. and the Canadian Neonatal Network. Incidence and timing of presentation of necrotizing enterocolitis in preterm infants. Pediatric. 2012; 129:e298-304.

Young, C. et al. Biomarkers for infants at risk for necrotizing enterocolitis: clues to preventing? Pediatr Res. 2009; 65:91R-7R.

\* cited by examiner

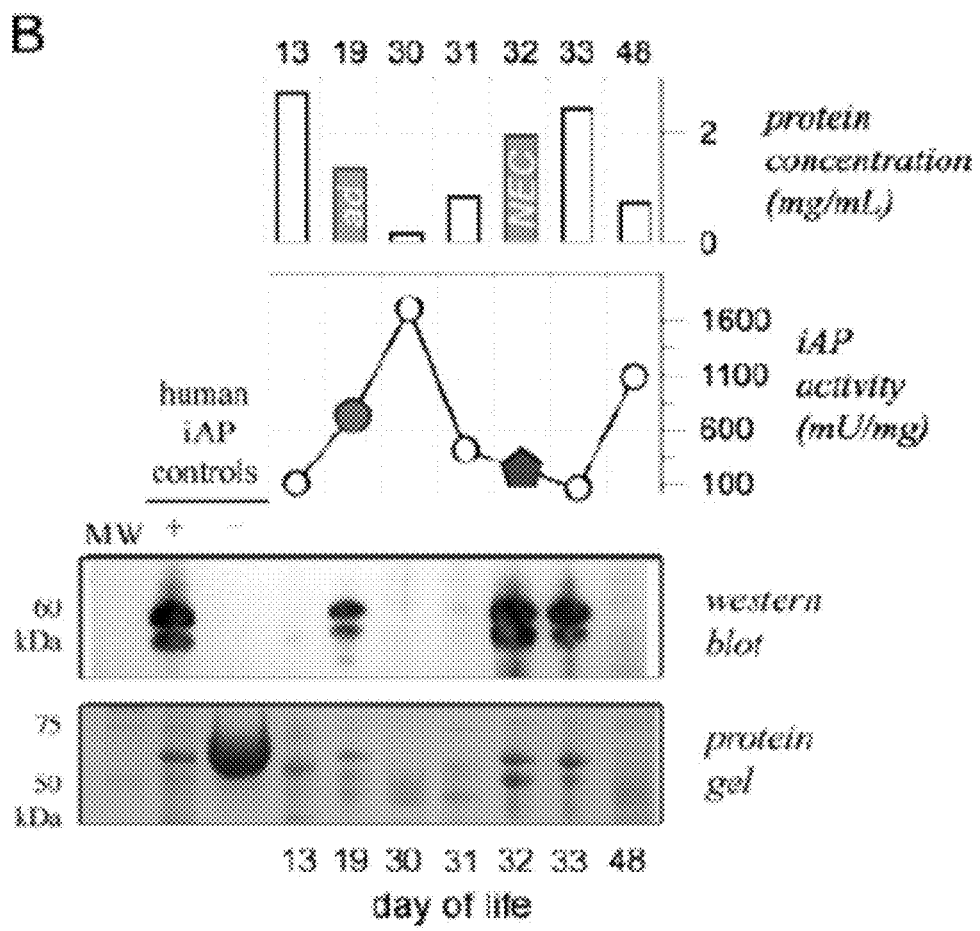
FIG. 1 CON'T

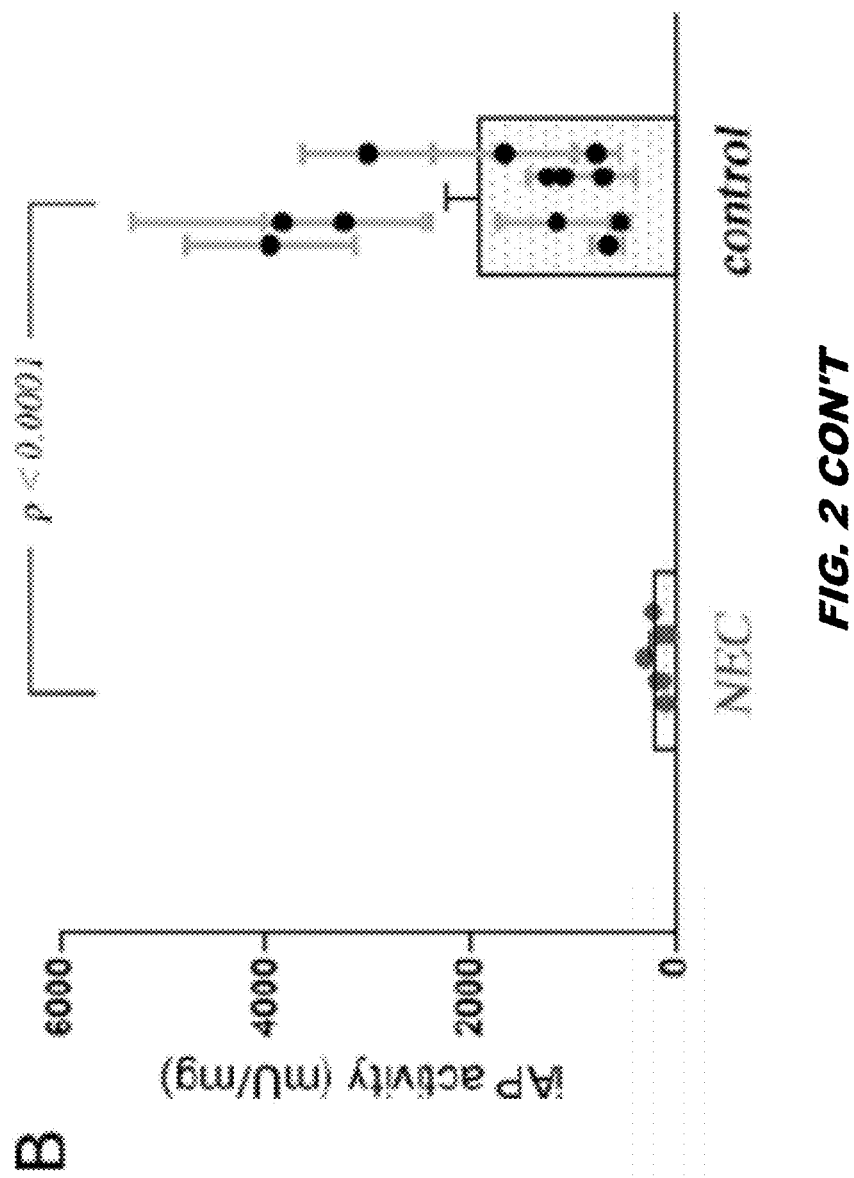
FIG. 2 CON'T

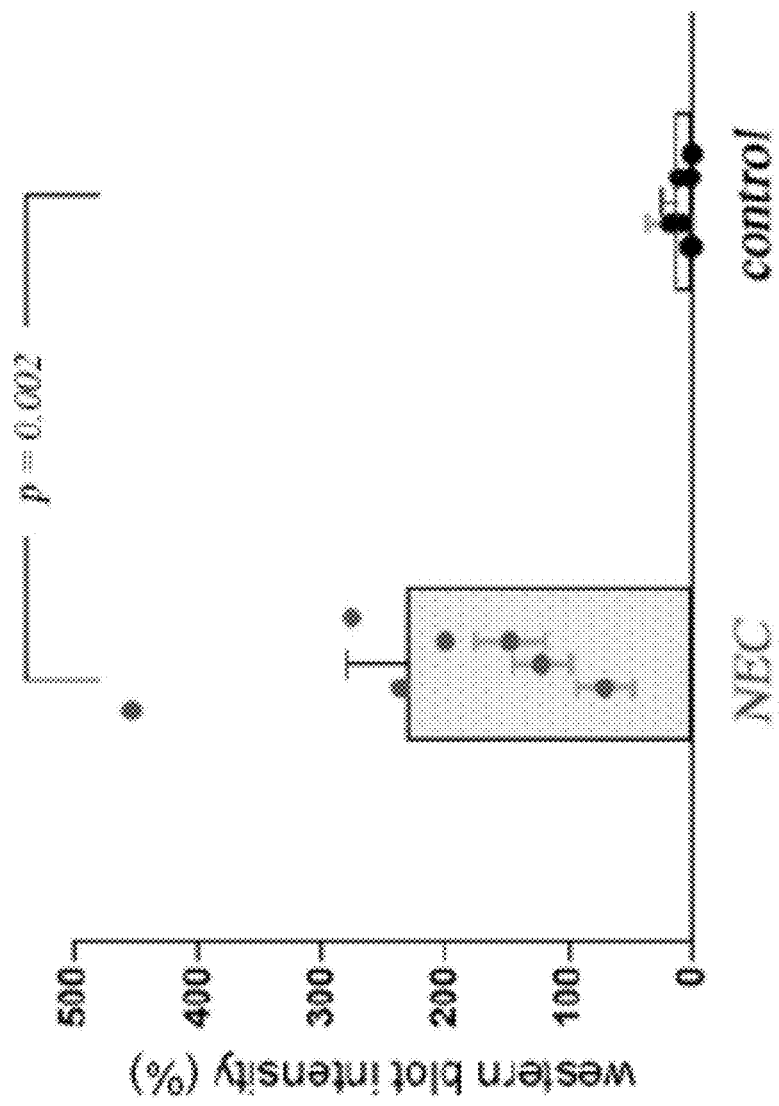
FIG. 2 CON'T

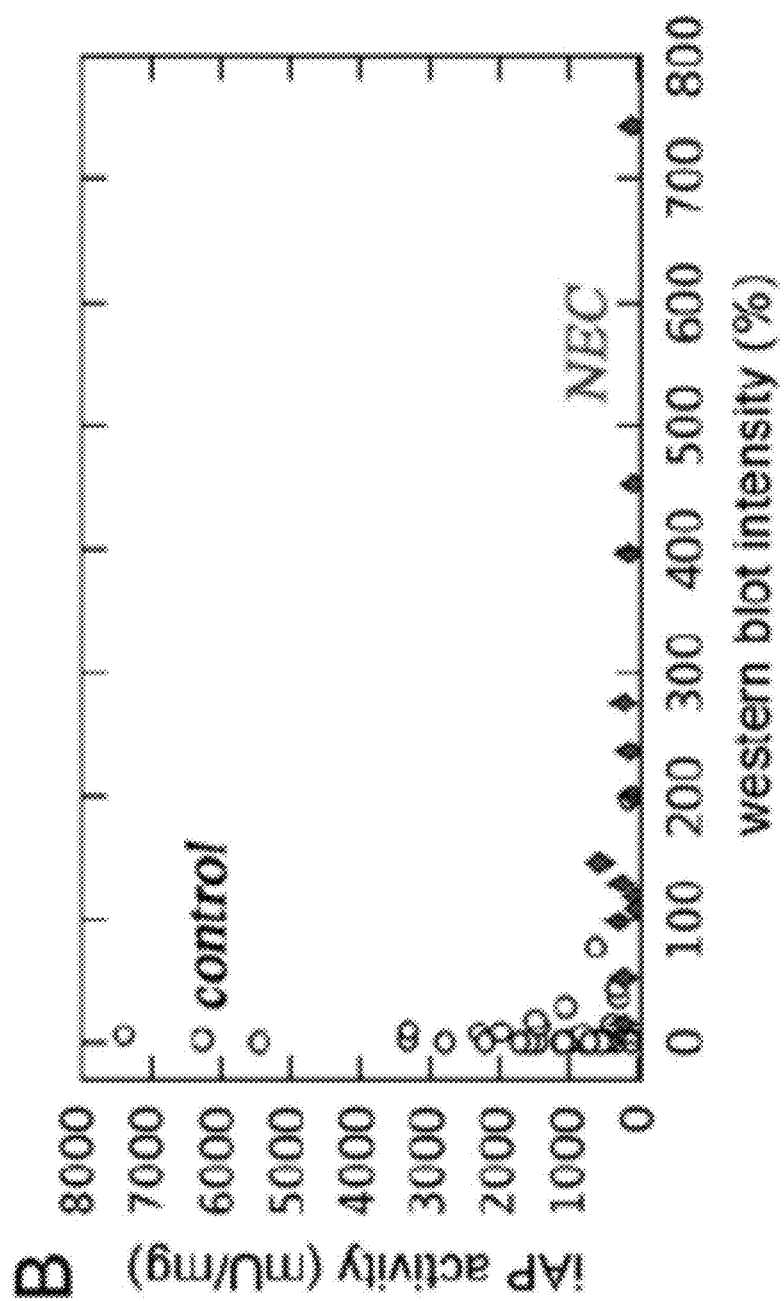
FIG. 3 CON'T

| Physical trait | | NEC infants (n=6) | Non-NEC infants (n=12) |
|---|---|---|---|
| Mean gestational age (weeks) | | 29.98 ± 3.32 | 29.87 ± 1.30 |
| Gestational age (weeks) | 23-26 | 1 | 5 |
| | 27-30 | 3 | 2 |
| | 31-34 | 1 | 4 |
| | 35-37 | 1 | 1 |
| Average birth weight (kg) | | 1.19 ± 0.58 | 1.30 ± 0.73 |
| Gender | male | 2 | 5 |
| | female | 4 | 7 |
| Bell Stage (NEC Events= 7) | I | 2 | n/a |
| | II | 2 | n/a |
| | III | 3 | n/a |

FIG. 4

Table 1. Demographics of patient enrollment in study.

| Physical trait | | NEC Infants (n=6) | Non-NEC Infants (n=12) |
|---|---|---|---|
| Bell Stage (NEC Events= 7) | I | 2 | n/a |
| | II | 2 | n/a |
| | III | 3 | n/a |
| Gestational age (WGA) | 23-26 | 1 | 5 |
| | 27-30 | 3 | 2 |
| | 31-34 | 1 | 4 |
| | 35-38 | 1 | 1 |
| Average birth weight (kg) | | 1.19 ± 0.58 | 1.30 ± 0.73 |
| Gender | male | 2 | 5 |
| | female | 4 | 7 |

*FIG. 6*

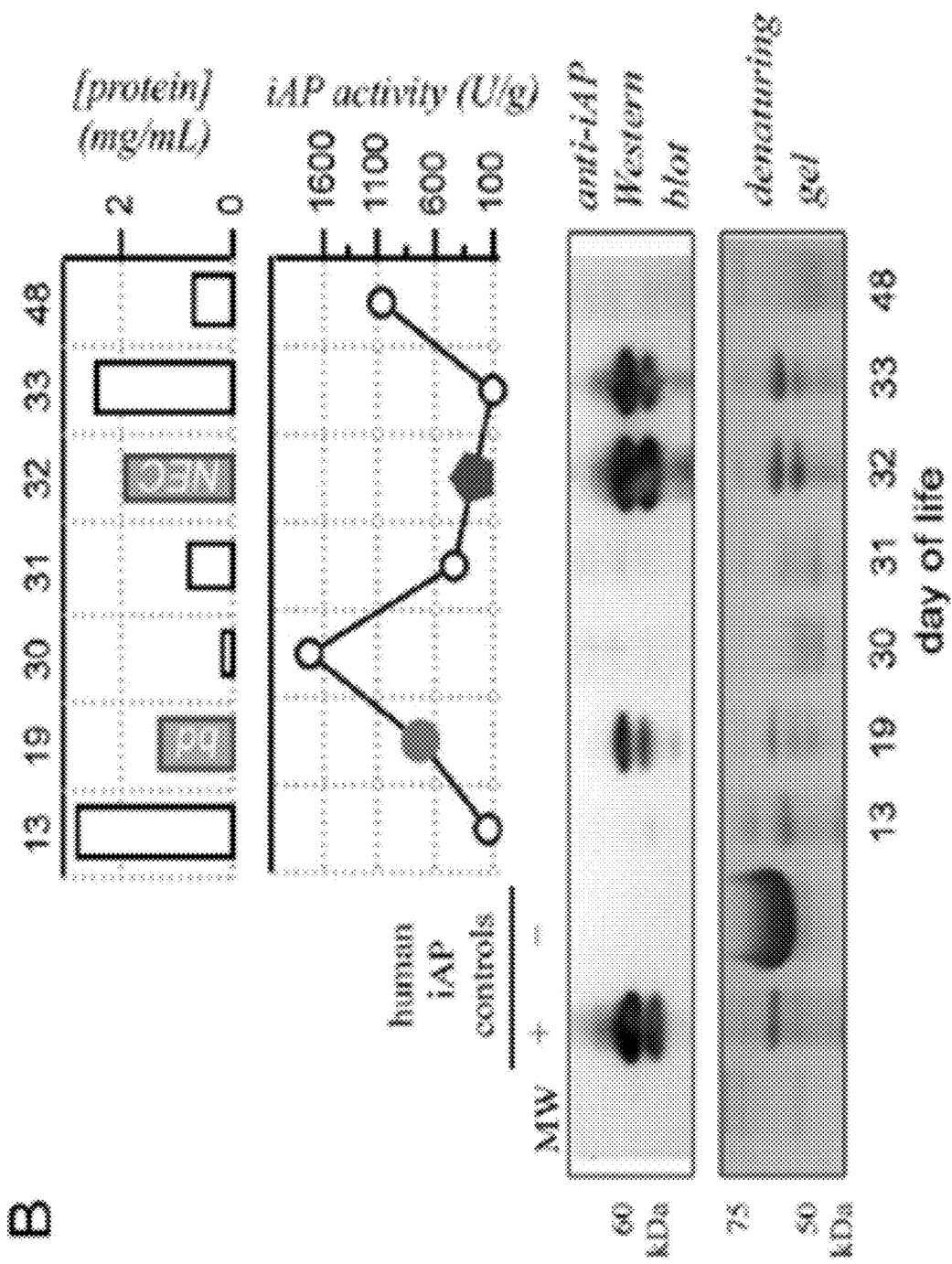
FIG. 10 CON'T

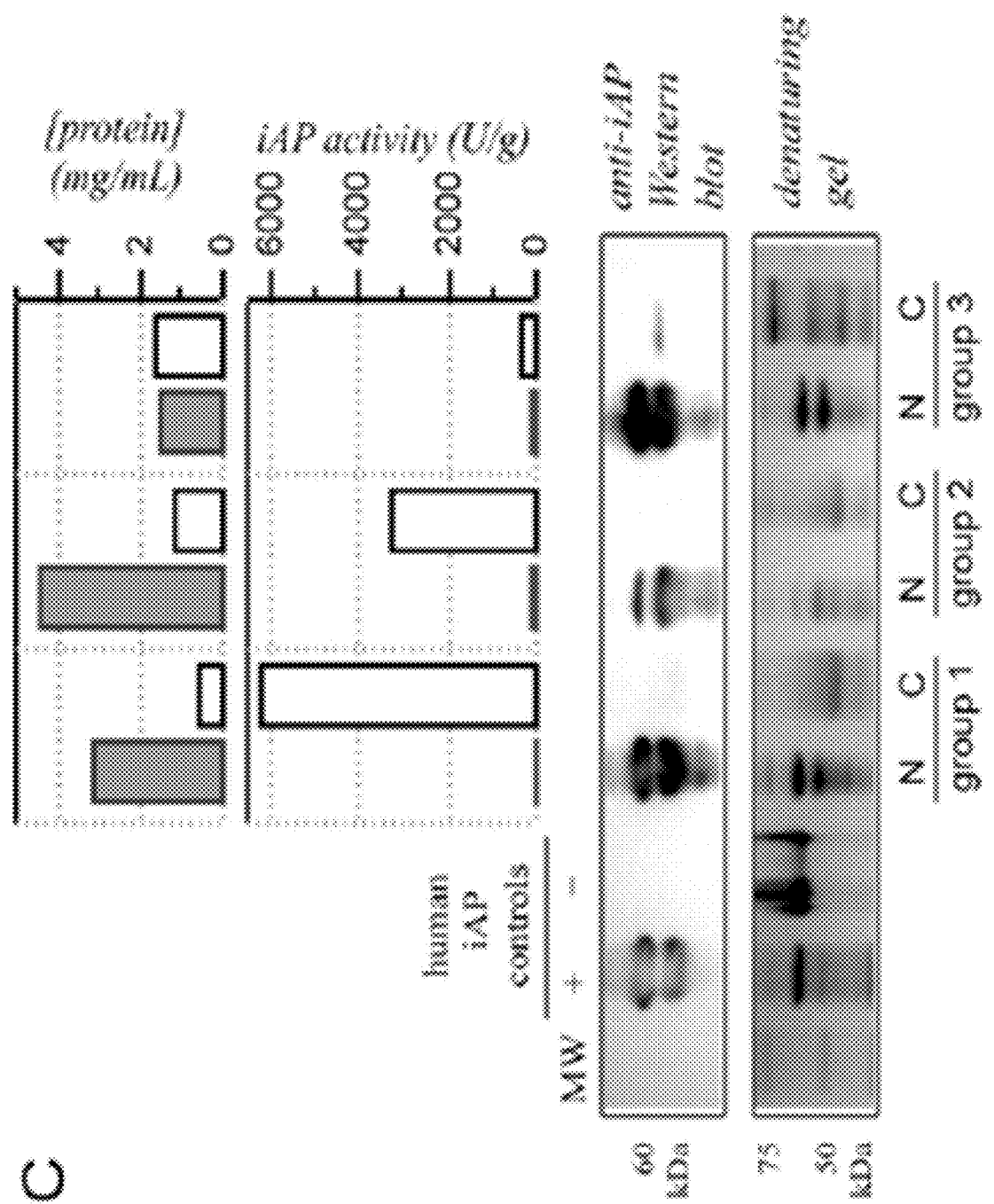
FIG. 10 CON'T

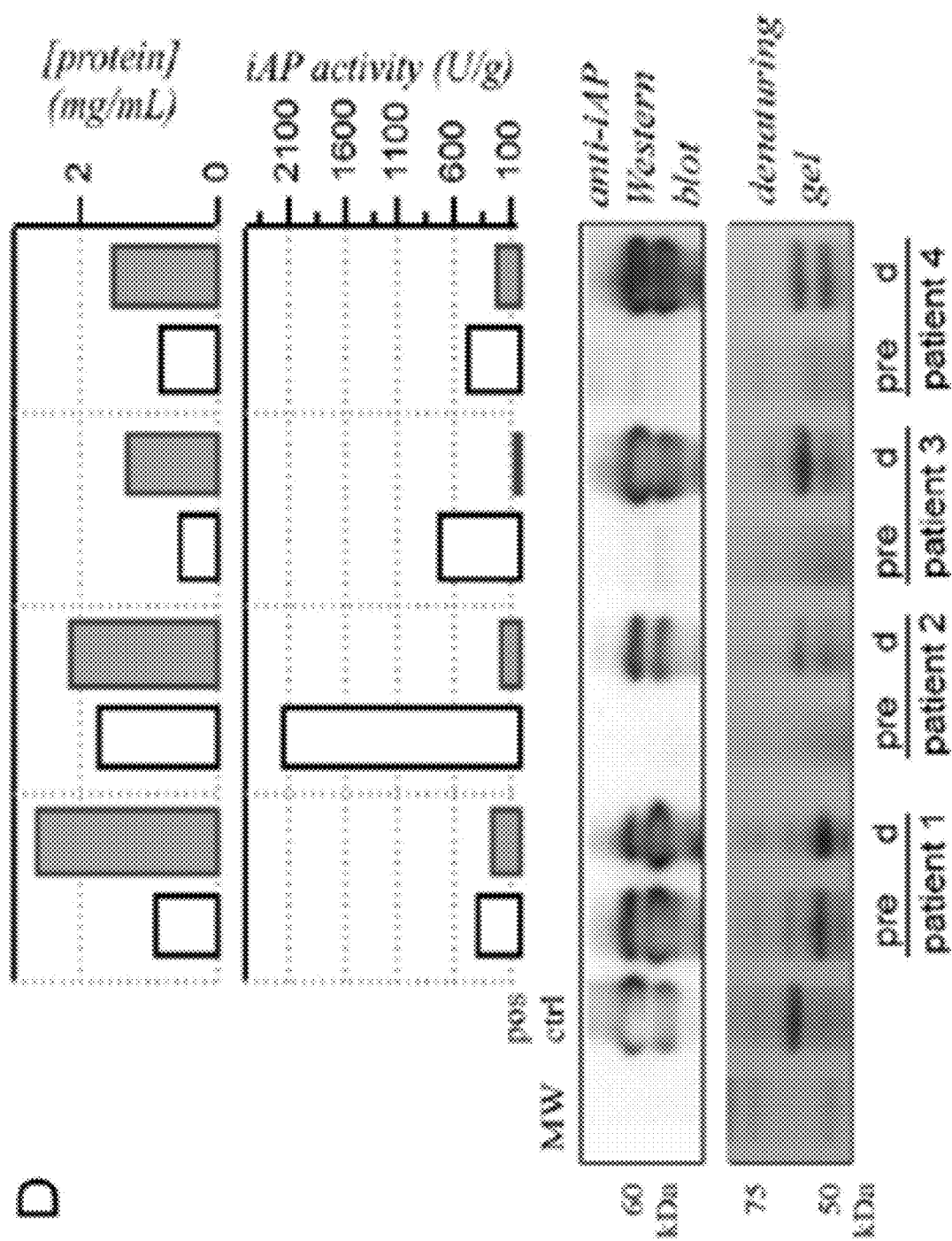
FIG. 10 CON'T

A.

B.
FIG. 11 CON'T
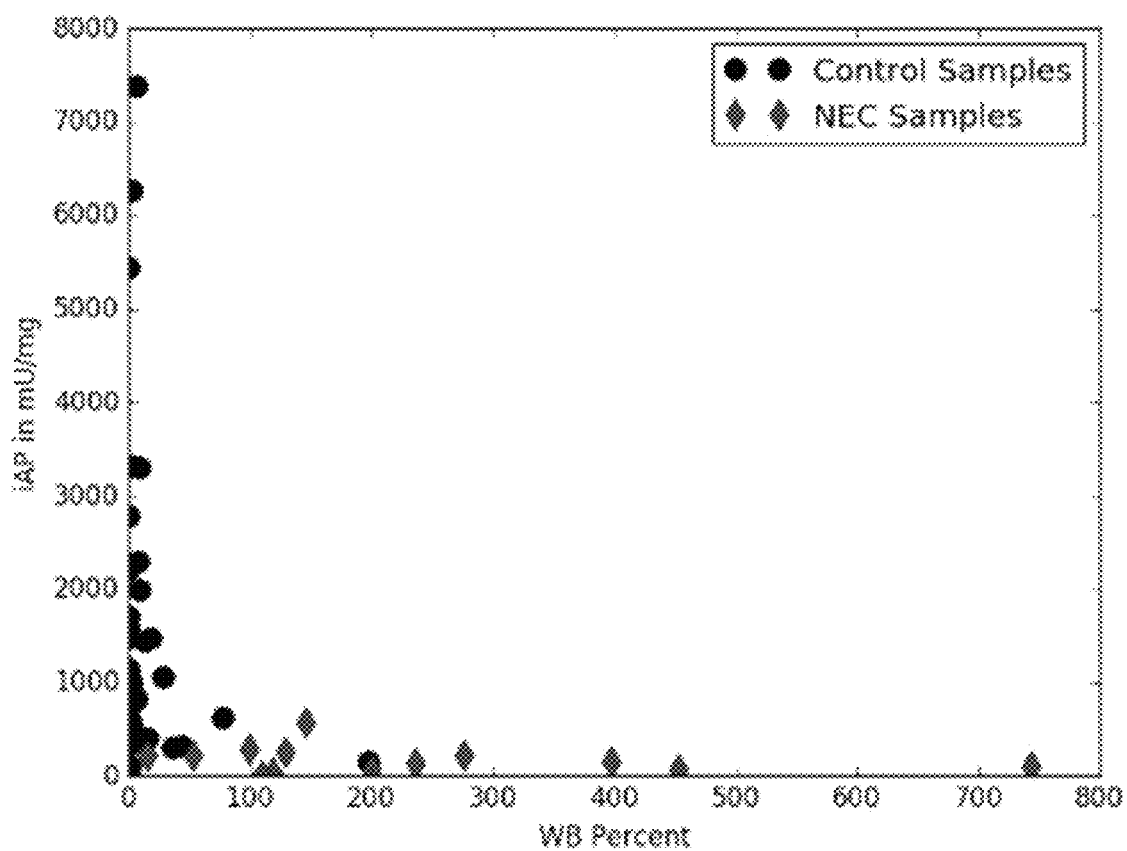

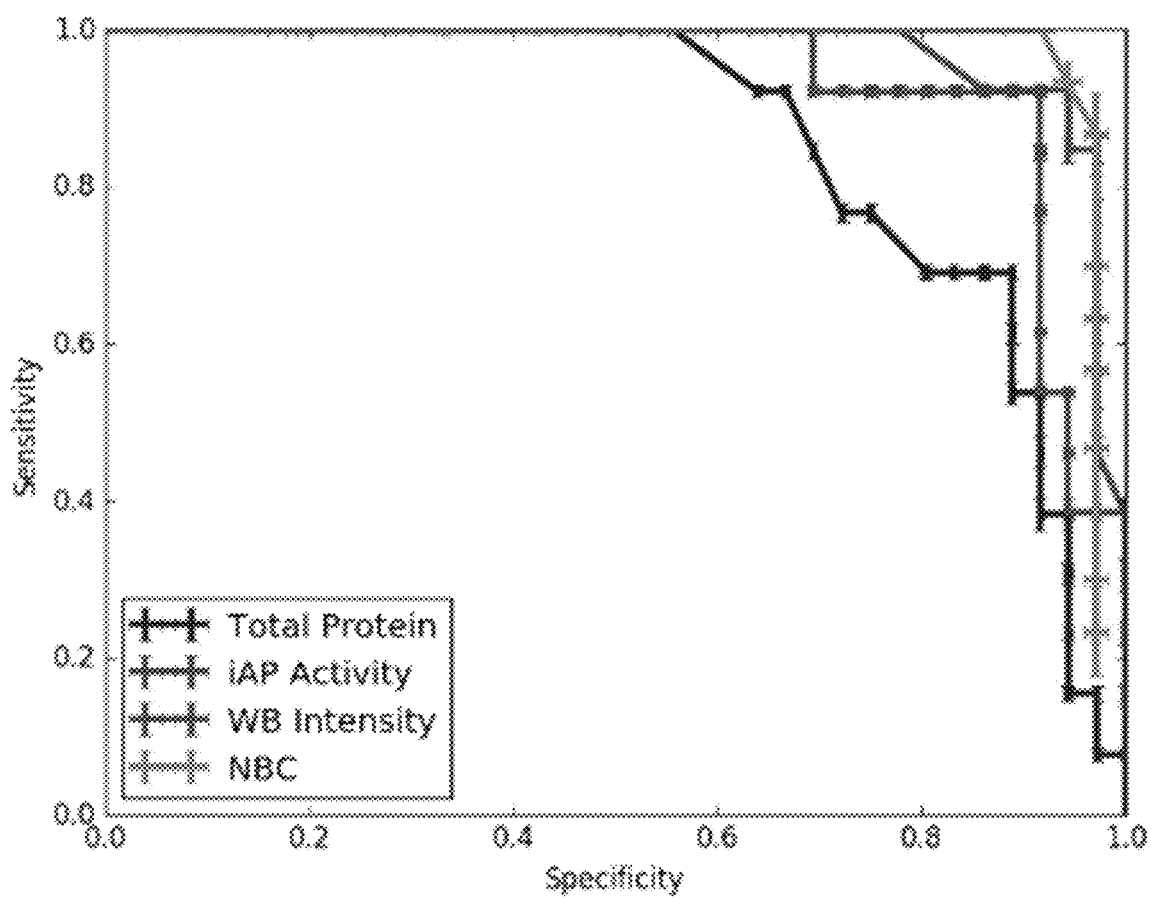
FIG. 11 CON'T

A.

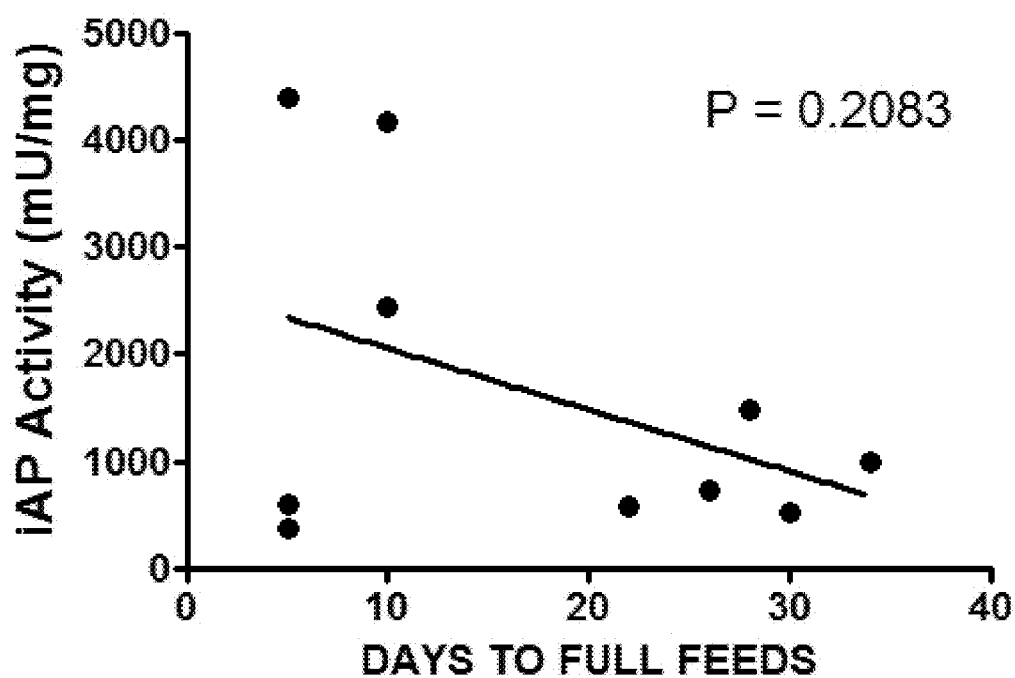
B.
FIG. 12 CON'T

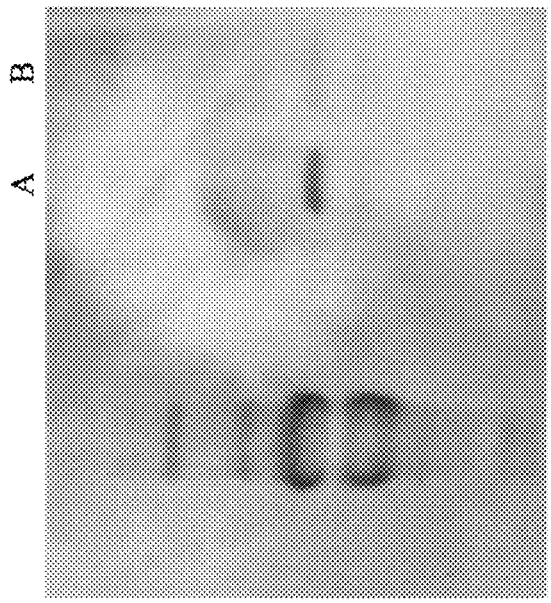
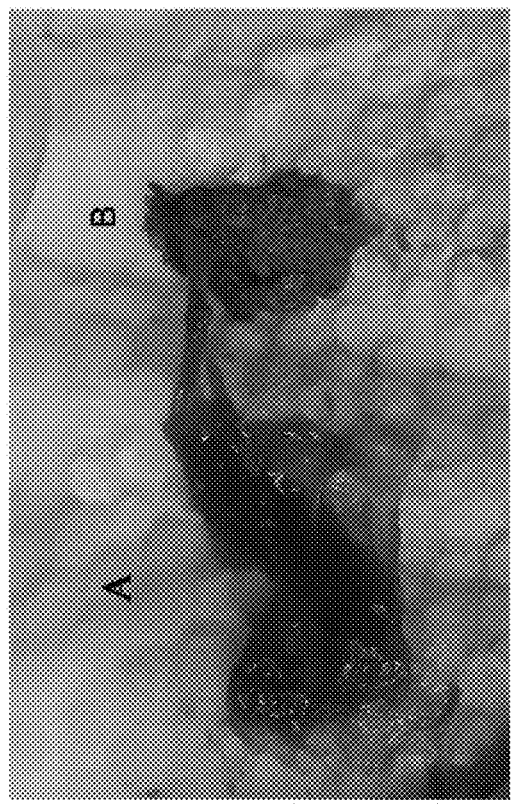
FIG. 13

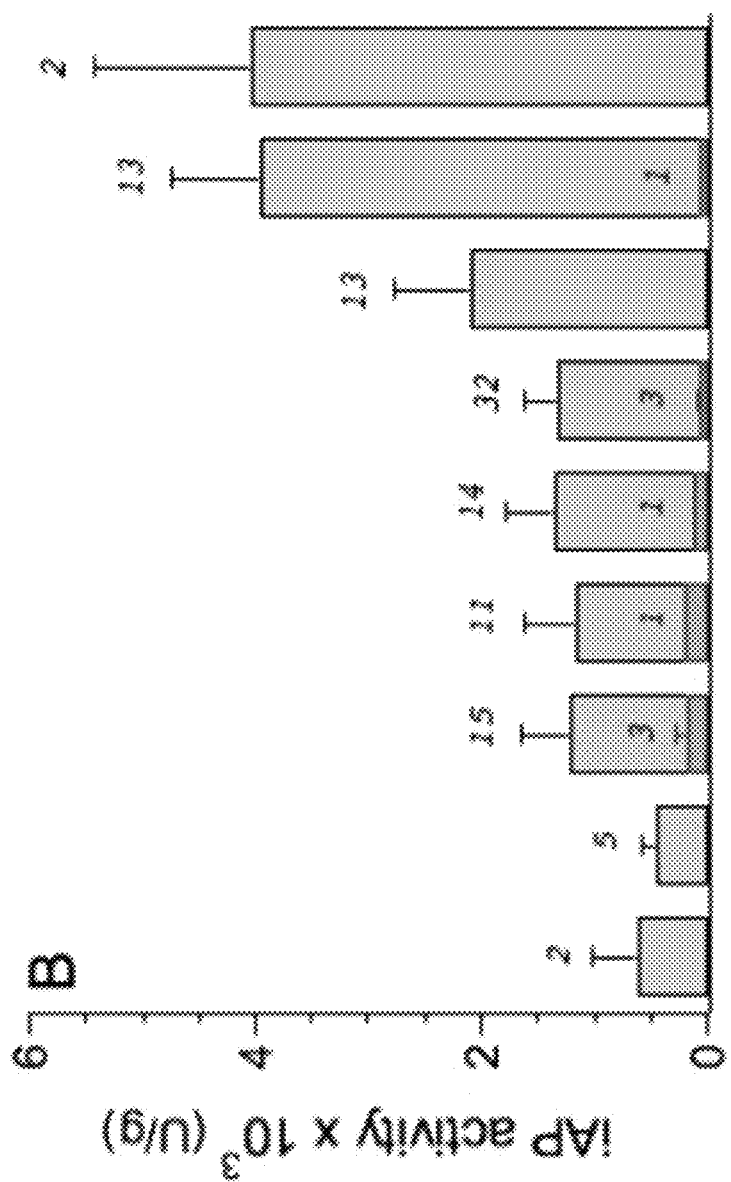
FIG. 14 CON'T

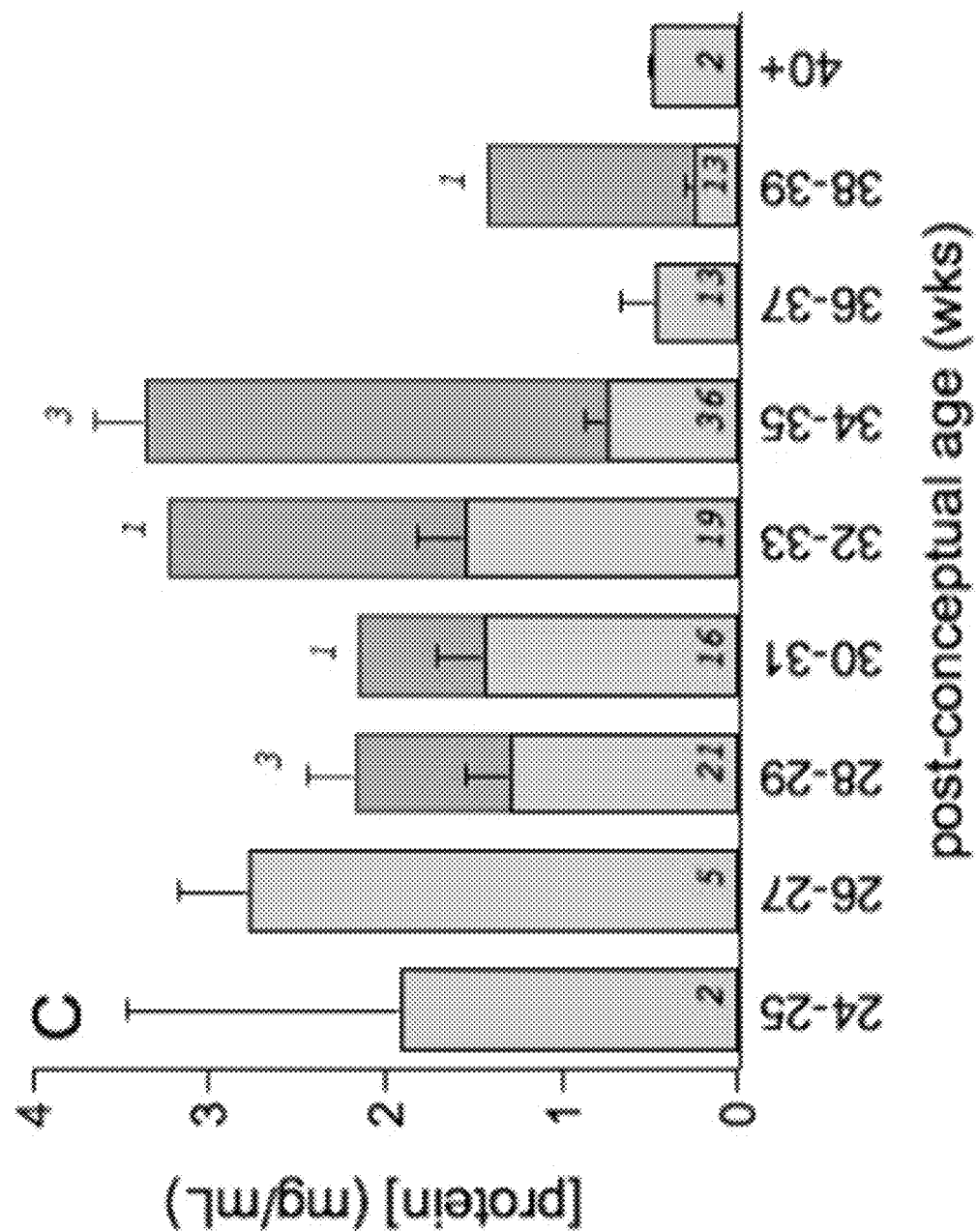
FIG. 14 CON'T

Lalles, Jean-Paul in Nutrition Reviews 2010 Vol 68

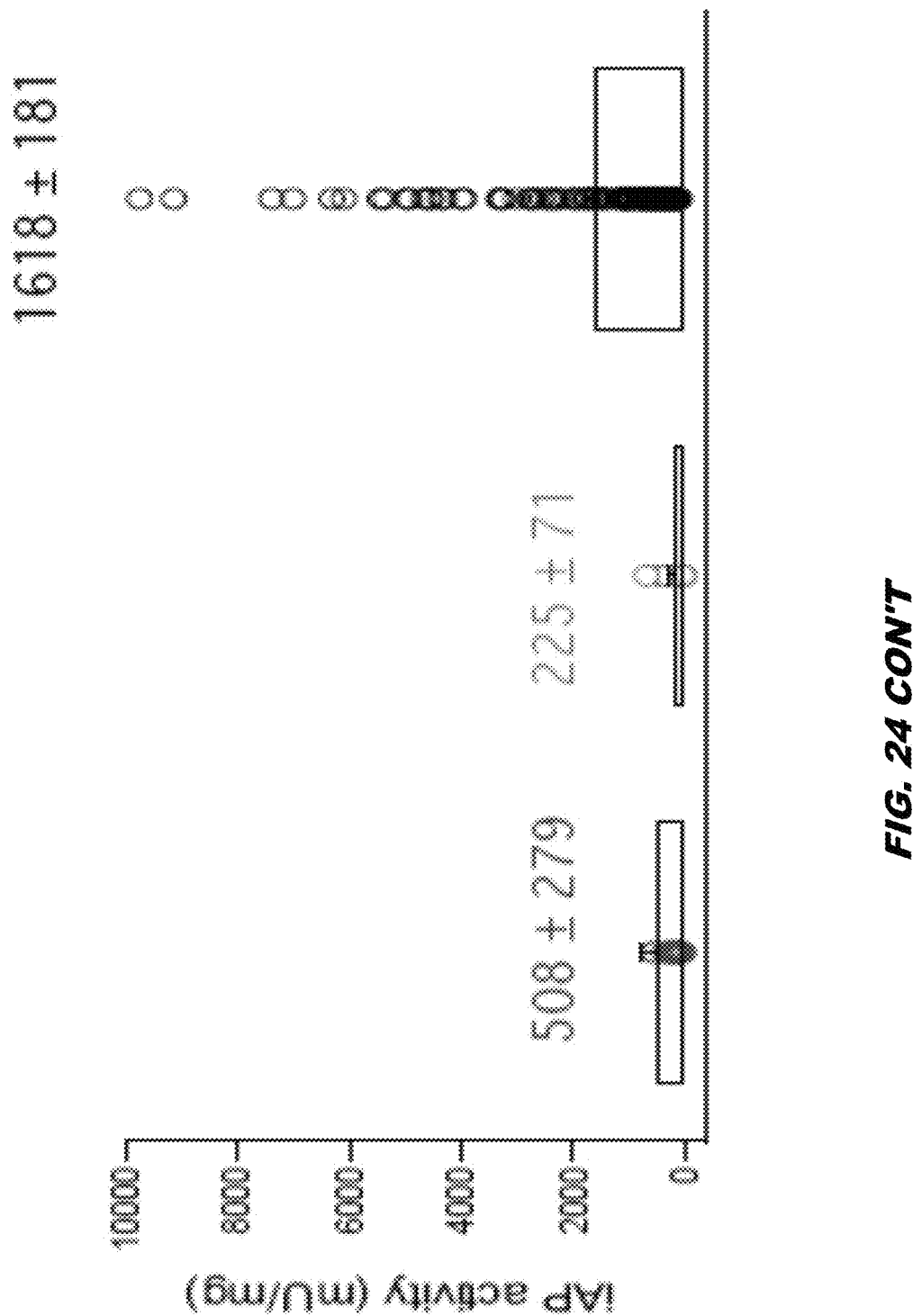
FIG. 24 CON'T

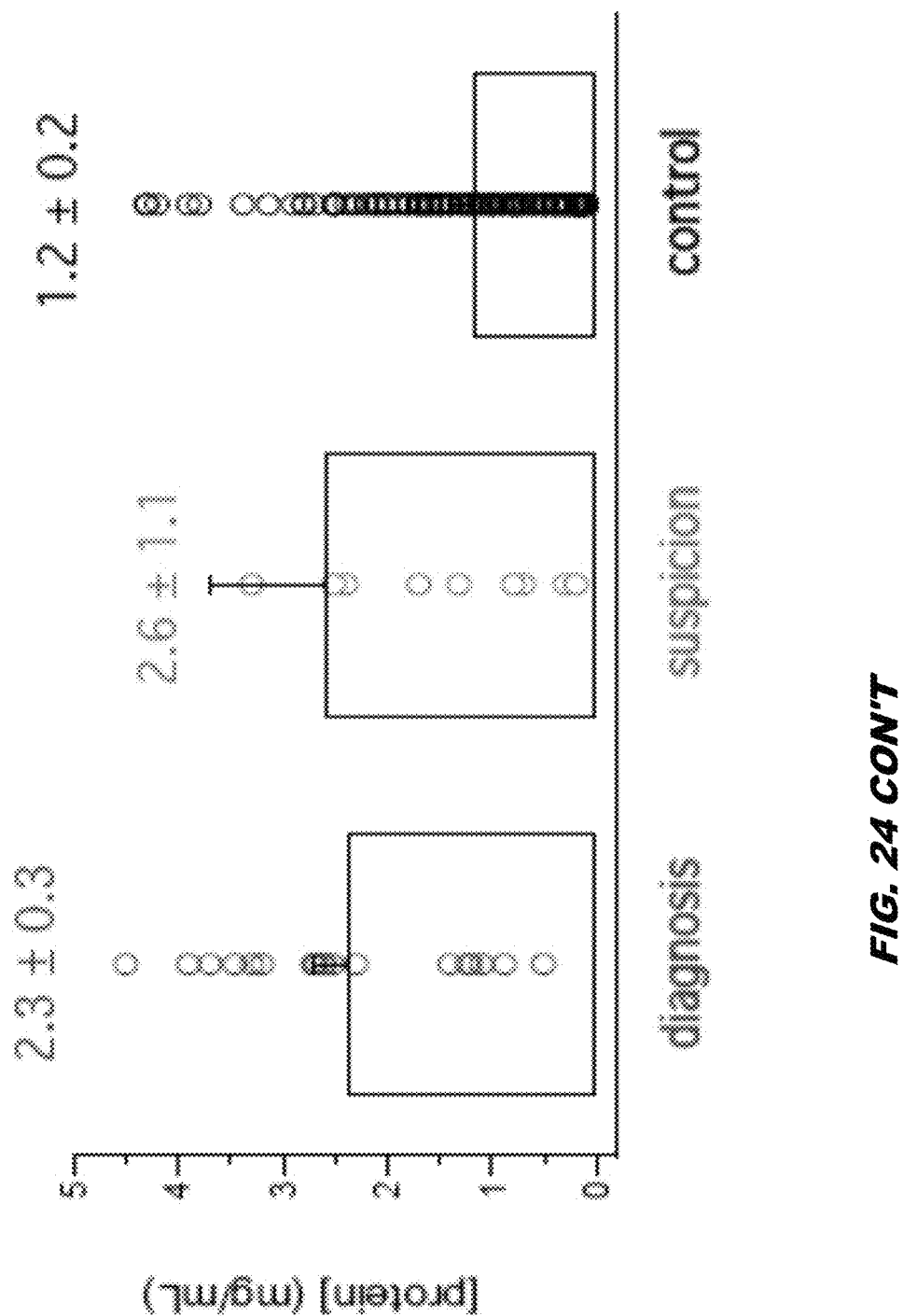
FIG. 24 CON'T

COMPOSITIONS AND METHODS TO DETECT GASTROINTESTINAL DISEASE

This application is a Continuation of application Ser. No. 16/267,120, filed Feb. 4, 2019; now U.S. Pat. No. 11,493,515, which is a Continuation in Part of International Application PCT/US2017/045588, filed on Aug. 4, 2017, which claims priority from U.S. Provisional Application No. 62/371,131, filed on Aug. 4, 2016, U.S. Provisional Application No. 62/378,820, filed on Aug. 24, 2016, U.S. Provisional Application No. 62/467,487, filed on Mar. 6, 2017, and U.S. Provisional Application No. 62/524,306, filed on Jun. 23, 2017, the entire contents of each which are incorporated herein by reference.

GOVERNMENT INTERESTS

This invention was made with government support under Grant No. R01GM097350 awarded by the National Institute of Health. The government has certain rights in the invention.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

FIELD OF THE INVENTION

This invention is directed to compositions and methods to detect and treat gastrointestinal diseases.

BACKGROUND OF THE INVENTION

Gastrointestinal diseases refer to diseases involving the gastrointestinal tract. For example, necrotizing enterocolitis (NEC) is an acquired gastrointestinal disease often seen in pre-term infants. In NEC, bacteria invade the wall of the intestine, causing local infection and inflammation. NEC is characterized by high mortality and long-term morbidity, including short gut syndrome, recurrent infection, nutritional deficiency and neurodevelopmental delay. Despite an overall net decrease in mortality for premature infants, there has been an increase in NEC-associated deaths. NEC is often difficult to diagnose and manage, due to initial nonspecific symptomatology and rapid deterioration. Clinicians currently rely on radiographic evidence to make the diagnosis in advanced stage of disease.

SUMMARY OF THE INVENTION

The present invention provides a method of identifying a subject afflicted with a gastrointestinal (GI) disease. An aspect of the invention is directed to methods for diagnosing a subject with a gastrointestinal disease. Another aspect of the invention is directed to methods for identifying a subject at risk of a gastrointestinal disease. Embodiments as described herein can further identify both early stages of gastrointestinal disease and advanced stages of gastrointestinal disease. Certain embodiments can distinguish between early stage and late stage gastrointestinal disease. For example, embodiments as described herein can diagnose advanced states of inflammation, such as that identified by radiological findings of pneumatosis intestinalis (portal vein or biliary gas). As another example, embodiments can identify early stages of the disease before rampant inflammation of the gut is physiologically evident.

In embodiments, the methods comprise incubating a biological sample from a subject with an agent that binds intestinal alkaline phosphatase (iAP), detecting in the sample iAP-bound agent, and detecting and/or measuring in the sample the amount or activity of iAP in sample, whether bound to the agent or not. In embodiments, the iAP-bound agent is at least one GI disease biomarker comprising AP enzymatic activity of iAP, iAP protein level, iAP dimerization/dissociation, post-translationally modified iAP, total protein, such as total fecal protein, or a combination thereof. In some embodiments, the GI disease biomarker is useful for diagnosing a subject with a gastrointestinal disease, and can also be indicative of a subject afflicted with a gastrointestinal (GI) disease, and/or a subject at risk of developing a GI disease. In some embodiments, a subject afflicted with a gastrointestinal (GI) disease can encompass both early and advanced stages of the disease.

In embodiments, iAP is not bound by an iAP binding agent. For example, a substrate can be provided for the enzyme in the sample, and the change of the substrate is monitored. In one embodiment, iAP is not bound for the activity assay. For example, substrate can be provided for the enzyme in the sample and the change in the enzyme can be monitored. Without being bound by theory, this can also be the same for AP-bound to enzyme where the measured change of substrate in immunoassays is for the protein tethered by the antibody system but also for any free AP in the sample.

The present invention further provides for a method of diagnosing a GI disease in a subject, such as necrotizing enterocolitis, comprising incubating a biological sample from a subject with an agent that binds intestinal alkaline phosphatase (iAP), detecting in the sample iAP-bound agent, and detecting and/or measuring in the sample the amount or activity of iAP-bound agent. In embodiments, the iAP-bound agent is at least one GI disease biomarker comprising iAP enzymatic activity, iAP protein level, iAP dimerization/dissociation, post-translationally modified iAP, total protein, such as total fecal protein, or a combination thereof, and wherein the GI disease biomarker is indicative of a subject afflicted with a gastrointestinal (GI) disease. An iAP-bound agent according to the invention can be iAP bound to its cognate substrate, an antibody that recognizes and binds to iAP, a short peptide sequence that is directed to and binds to iAP, and the like, non-limiting examples of which comprise a small-molecule activator or inhibitor of the catalytic reaction, a metal ion (tungsten is a transition state effector of alkaline phosphatases), an agent that causes allosteric release of products, a labile chemical moiety that serves as a chemical, enzymatic, or photolytic trigger, or a matrix that binds to a tagged form of iAP.

Embodiments can further comprise diagnosing the subject as having a GI disease. For example, a subject can be diagnosed as having a GI disease: if the total protein concentration in the sample is greater than about 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml or 5.0 mg/ml; if the iAP activity is less than about 10 mU/mg, 20 mU/mg, 30 mU/mg, 40 mU/mg, 50 mU/mg, 60 mU/mg, 70 mU/mg, 80 mU/mg, 90 mU/mg, 100 mU/mg, 200 mU/mg, 300 mU/mg, 400 mU/mg, 500 mU/mg, 600 mU/mg, 700 mU/mg, 800 mU/mg, 900 mU/mg, 1000 mU/mg, 1050 mU/mg, 1100 mU/mg, 1150 mU/mg, 1200 mU/mg, 1250 mU/mg, 1300 mU/mg, 1350 mU/mg 100 mU/mg, 1450 mU/mg, 1500 mU/mg, 1600 mU/mg, 1700 mU/mg, 1800 mU/mg, 1900 mU/mg; if the iAP activity is less than about 5 U/mg, 10 U/mg, 50 U/mg, 100 U/mg, 200 U/mg, 300 U/mg, 400 U/mg, 500 U/mg, 600 U/mg, 700 U/mg, 800 U/mg, 900 U/mg, 1000 U/mg; if the level of iAP protein is greater than 0.05%, 1%, 2%, 3%, 4%, 5%, 6%, 7%, 8%, 9%, 10%, 20%, 30%, 40%, 50%, 60%, 70%, 80%, 90%, 100%, 125%, 150%, 175%, 200%, 225%, 250%, 275% of a control sample, or a combination thereof. Without being bound by theory, total protein concentration in the sample as described herein can be for a stool sample in which the fresh weight to buffer is set at 1 g/mL. Otherwise, the skilled artisan knows that one can dilute or concentrate a sample to alter the protein concentration.

In embodiments, a subject can be diagnosed as having a GI disease if the total protein concentration in the sample is greater than about 1.8 mg/ml, if the iAP activity is lower than about 979 mU/mg, if the level of iAP protein is greater than 10.7% of a control sample, or a combination thereof. In some embodiments, a subject can be diagnosed as having a GI disease if the total protein concentration in the sample is greater than about 1.6 mg/ml, if the iAP activity is lower than about 1256 mU/mg, if the level of iAP protein is greater than 4.8% of a control sample, or a combination thereof.

The present invention provides a method of diagnosing a gastrointestinal (GI) disease in a subject comprising obtaining a sample from the subject, detecting the presence of at least one GI disease biomarker in the sample, wherein the GI disease biomarker can comprise intestinal alkaline phosphatase (iAP) protein, comparing the GI disease biomarker profile to that of a profile obtained from a control sample, and treating the subject. In embodiments, the control sample can comprise two or more control samples.

The present invention further provides a method of preventing the progression of a gastrointestinal disease in a subject in need thereof comprising obtaining a sample from the subject, detecting the presence of at least one GI disease biomarker in the sample, wherein the GI disease biomarker can comprise intestinal alkaline phosphatase (iAP) protein, comparing the GI disease biomarker profile to that of a profile obtained from a control sample, and treating the subject. In embodiments, the control sample can comprise two or more control samples.

The present invention further provides a method of ameliorating the symptoms associated with a gastrointestinal disease in a subject in need thereof comprising obtaining a sample from the subject, detecting the presence of at least one GI disease biomarker in the sample, wherein the GI disease biomarker can comprise intestinal alkaline phosphatase (iAP) protein, comparing the GI disease biomarker profile to that of a profile obtained from a control sample, and treating the subject. In embodiments, the control sample can comprise two or more control samples.

In embodiments, treating the subject diagnosed with a GI disease comprises administering an effective amount of antibiotics, probiotics, intravenous fluids, or a combination thereof; withholding oral feeding; administering an iAP replacement composition; an anti-inflammatory; a therapeutic; a small molecule activator and/or effector of catalytic activity; parenteral (or intravenous) nutrition or a combination thereof.

Non-limiting examples of a therapeutic that can be used according to the invention comprise Toll-like receptor (TLR) inhibitors (Neal et al. Discovery and validation of a new class of small molecule Toll-like receptor 4 (TLR4) inhibitors. PloS One 12, e65779) and interruption of eNOS-NO-nitrite signaling (Yazji et al. Endothelial TLR4 activation impairs intestinal microcirculatory perfusion in necrotizing enterocolitis via eNOS-NO-nitrite signaling. Proceedings of the National Academy of Science USA 110, 9451-9456).

Non-limiting examples of a small molecule effector of catalytic activity comprise levamisole, theophylline, triazole-based compounds, sulfonamide derivatives, phosphatase derivatives, metals, and amino acids (Borgers M. The cytochemical application of new potent inhibitors of alkaline phosphatases. Journal of Histochemistry & Cytochemistry 21, 812-824; Klemperer et al. The inhibition of alkaline phosphatase by beryllium. Journal of Biological Chemistry 180, 281-288; Bobkova et al. Modulators of intestinal alkaline phosphatase. Methods Mol Biol 1053, 135-144; Narisawa et al. Novel inhibitors of alkaline phosphatase suppress vascular smooth muscle cell calcification. Journal of Bone and Mineral Research 22, 1700-1710; al-Rashida and Iqbal. Inhibition of alkaline phosphatase: an emerging new drug target. Minireviews in Medicinal Chemistry 15, 41-51.

Non-limiting examples of such antibiotics comprise Vancomycin, Ampicillin, Zosyn (combination of piperacillin and tazobactam), Gentamycin, Flagyl (metronidazole generic), Meropenem, Metronidazole, Cefotaxime, Clindamycin, or any combination thereof. In some embodiments, an antifungal agent can further be administered. In other embodiments, the antifungal agent can be Fluconazole, Terconazole, Voriconazole, Posaconazole, Pentamidine, Itraconazole, and Ketoconazole.

Non-limiting examples of probiotic organisms include those in the genera *Lactobacillus, Lactococcus, Bifidobacteria, Pediococcus, Saccharomyces boulardii*, and related bacteria and yeast.

Non-limiting examples of such intravenous fluids comprise saline (such as 0.9% NaCl in water or 0.45% saline in water), Lactated Ringer's (0.9% NaCl with electrolytes and buffer), $D_5W$ (5% dextrose in water), $D_5NS$ (5% dextrose in 0.9% saline), $D_5$ ½ NS (5% dextrose in 0.45% saline), $D_5LR$ (5% dextrose in Lactated Ringer's), or Normosol-R. In embodiments, the intravenous fluid solution can be isotonic. In other embodiments, the intravenous fluid solution can be hypotonic.

Non-limiting examples of parenteral (or intravenous) nutrition comprise intravenous dextrose solutions, intravenous amino acid solutions, intravenous fat emulsions, intravenous vitamin and mineral supplements, or a combination thereof.

The anti-inflammatory agents can be selected from a wide variety of steroidal, non-steroidal, and salicylate water-soluble and water-insoluble drugs and their acid addition or metallic salts. Both organic and inorganic salts can be used provided the anti-inflammatory agent maintains its medicament value. The anti-inflammatory agents can be selected from a wide range of therapeutic agents and mixtures of therapeutic agents that can be administered in sustained release or prolonged action form. Non-limiting examples of anti-inflammatory agents comprise ibuprofen, naproxen, sulindac, diflunisal, piroxicam, indomethacin, etodolac, meclofenamate sodium, fenoproben calcium, ketoprofen, mefenamic acid, nabumetone, ketorolac tromethamine, diclofenac, and evening primrose oil (containing about 72% linoleic acid and about 9% gamma-linolenic acid). Nonlimiting examples of salicylate anti-inflammatory agents comprise acetylsalicylic acid, mesalamine, salsalate, diflunisal, salicylsalicylic acid, and choline magnesium trisalicylate. Nonlimiting examples of steroidal anti-inflammatory agents comprise flunisolide, triamcinoline, triamcinoline acetonide, beclomethasone diprorionate, betamethasone diproprionate, hydrocortisone, cortisone, dexamethasone, prednisone, methyl prednisolone, and prednisolone.

In embodiments, the gastrointestinal disease can comprise colitis, inflammatory bowel disease (IBD), or a combination thereof. In embodiments, colitis can comprise necrotizing enterocolitis (NEC), adult necrotizing enterocolitis (ANEC), pseudomembranous enterocolitis, infectious colitis, ulcerative colitis, Crohn's disease, ischemic colitis, and radiation colitis.

In embodiments, the sample can comprise a biological sample obtained from subject. For example, the biological sample can be a biological fluid, a biological solid, or a biological semi-solid. In embodiments, the sample can comprise fecal matter, meconium, vomit, peripheral blood, sera, plasma, or urine.

In embodiments, the GI disease biomarker can comprise iAP enzymatic activity, AP enzymatic activity, iAP protein level, iAP dimerization/dissociation, post-translationally modified iAP, total protein, such as total fecal protein, or a combination thereof. In embodiments, the post-translational modification can comprise acetylation, acylation, alkylation, amidation, butyrylation, deamidation, formylation, glypiation, glycosylation, hydroxylation, iodination, ISGylation, lipoylation, malonylation, methylation, myristoylation, palmitoylation, phosphorylation, phosphopantetheinylation, prenylation, propionylation, ribosylation succinylation, sulfation, SUMOylation, or ubiquitination.

In embodiments, the GI disease biomarker can comprise a NEC biomarker.

In embodiments, detecting can comprise an immunoassay, a colorimetric assay, a fluorimetric assay or a combination of both. In embodiments, the immunoassay can comprise a western blot assay, an enzyme-linked immunosorbent assay (ELISA), immunoprecipitation, single molecule immunoassays in femoliter chamber arrays, digital enzyme assays in both single and multiplex forms, or a combination thereof. In embodiments, the detecting comprise contacting the sample with an anti-iAP antibody. In embodiments, the anti-iAP antibody is a polyclonal or monoclonal antibody. In embodiments, detecting can comprise a kinetic assay, an endpoint assay, Bradford assay, a bicinchoninic acid (BCA) assay, a Lowry assay, a pyrogallol red protein dye-binding assay, a Coomassie blue dye-binding assay, or a combination thereof.

In still other embodiments, detecting can comprise techniques known to one skilled in the art, such as mass spectrometry (MS), RNA sequencing, and immunostaining of patient samples. For example, RNA sequencing of intestinal alkaline phosphatase or other alkaline phosphatases is rapid method of detecting molecules, such as iAP (Knight et al. Non-invasive analysis of intestinal development in preterm and term infants using RNA-sequencing. 2014. Scientific Reports 4, 5453).

In embodiments, the assay can detect phosphatase activity. Non-limiting examples of such assays comprise fluorescent, chemiluminescent, or colorimetric detection methods, an assay to detect ATP hydrolysis and/or products of ATP hydrolysis, or a combination thereof.

In embodiments, detecting can comprise a kinetic assay comprising use of 4-methylumbelliferyl phosphate, CPD Star (Disodium 2-chloro-5-(4-methoxyspiro[1,2-dioxetane-3,2'-(5-chlorotricyclo[3.3.1.1$^{3.7}$]decan])-4-yl]-1-phenyl phosphate), AttosPho (2'-[2-benzothiazoyl]-6'-hydroxybenzothiazole phosphate [BBTP]), or any other fluorometric or colorimetric signal, an assay to detect ATP hydrolysis and/or products of ATP hydrolysis (for example, malachite green, NADH-coupled, or other proprietary variation), or a combination thereof.

In embodiments, alkaline phosphatase activity, such as intestinal alkaline phosphatase activity, can be directly detected and/or measured by admixing with the biological sample for a period of time chromogenic substrates and/or fluorogenic substrates of alkaline phosphatase, such as iAP. For example, 4-methylumbelliferyl phosphate (MUP) is a fluorogenic substrate for alkaline phosphatases, and alkaline phosphatase mediated hydrolysis of its phosphate substituent yields the blue-fluorescent 4-methylumbelliferyl (excitation/emission ~386/448 nm). In embodiments, the MUP can be directly admixed with the biological sample, such as stool, allowing for the direct detection of the presence of alkaline phosphatase or the measurement of its activity.

Non-limiting examples of Alkaline phosphatase (AP) substrates comprise AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color), Fluorescein diacetate, 4-Methylumbelliferyl acetate, 4-Methylumbelliferyl casein, 4-Methylumbelliferyl-α-L-arabinopyranoside, 4-Methylumbelliferyl-β-D-fucopyranoside, 4-Methylumbelliferyl-α-L-fucopyranoside, 4-Methylumbelliferyl-β-L-fucopyranoside, 4-Methylumbelliferyl-α-D-galactopyranoside, 4-Methylumbelliferyl-β-D-galactopyranoside, 4-Methylumbelliferyl-α-D-glucopyranoside, 4-Methylumbelliferyl-β-D-glucopyranoside, 4-Methylumbelliferyl-β-D-glucuronide, 4-Methylumbelliferyl nonanoate, 4-Methylumbelliferyl oleate, 4-Methylumbelliferyl phosphate, bis(4-Methylumbelliferyl)phosphate, 4-Methylumbelliferyl pyrophosphate diester, 4-Methylumbelliferyl-3-D-xylopyranoside.

Non-limiting examples of suitable chromogenic substrates for use within the present invention comprise o-Nitrophenyl-β-D-galactopyranoside, p-Nitrophenyl-β-D-galactopyranoside, o-Nitrophenyl-β-D-glucopyranoside, p-Nitrophenyl-α-D-glucopyranoside, p-Nitrophenyl-β-D-glucopyranoside, p-Nitrophenyl-β-D-glucuronide, p-Nitrophenyl phosphate, o-Nitrophenyl-β-D-xylopyranoside, p-Nitrophenyl-α-D-xylopyranoside, p-Nitrophenyl-β-D-xylopyranoside, and Phenolphthalein-β-D-glucuronide.

In embodiments, the method as described herein further comprise diagnosing the subject with a gastrointestinal disease if the protein level of iAP in the sample is at least two standard deviations above the mean protein level of the control sample. In embodiments, the method as described herein further comprise diagnosing the subject with a gastrointestinal disease if the protein level of iAP in the sample is at least 1, 1.5, 2, 2.5, 3, 3.5, 4, 4.5, 5 standard deviations above the mean protein level of the control sample. In embodiments, the control sample can comprise two or more control samples. Embodiments can comprise 10 mg, 20 mg, 30 mg, 40 mg, 50 mg, 60 mg, 70 mg, 80 mg, 90 mg, 100 mg, 125 mg, 150 mg, 175 mg, 200 mg, 225 mg, 250 mg, 275 mg, or 300 mg fresh weight stool/mL sterile water or buffer. For example, embodiments can comprise 200 mg fresh weigh stool/mL sterile water or buffer In embodiments, the method as described herein further comprise diagnosing the subject with a gastrointestinal disease or at risk of a gastrointestinal disease if the protein level of iAP in the sample is greater than 4.8% of the control sample. In other embodiments, the method described herein further comprise diagnosing the subject with a gastrointestinal disease or at risk of a gastrointestinal disease if the protein level of iAP in the sample is greater than 107% of the control sample. In embodiments, the method as described herein further comprise diagnosing the subject with a gastrointestinal disease or at risk of a gastrointestinal disease if the protein level of iAP in the sample is greater than 2.5%, 5%, 10%, 15%, 20%, 25%, 30%, 40%, 50%, 60%, 70%, 80%, 90%, 100%, 125%, 150%, 175%, 200%, 225%, 250%, 275%, 300%, 325%, 350%, 375%, 400% of the control sample.

In embodiments, the method as described herein further comprise diagnosing the subject with a gastrointestinal disease if the level of iAP enzyme activity in the sample is at least two standard deviations below the mean iAP enzyme activity of the control sample. In embodiments, the method as described herein further comprise diagnosing the subject with a gastrointestinal disease if the level of iAP enzyme activity in the sample is at least 1, 1.5, 2, 2.5, 3, 3.5, 4, 4.5, 5 standard deviations above the mean enzyme activity of the control sample. In embodiments, the control sample can comprise two or more control samples. In embodiments, the method as described herein further comprise diagnosing the subject with a gastrointestinal disease or at risk of a gastrointestinal disease if the level of iAP enzyme activity in the sample is lower than about 10 mU/mg, 20 mU/mg, 30 mU/mg, 40 mU/mg, 50 mU/mg, 60 mU/mg, 70 mU/mg, 80 mU/mg, 90 mU/mg, 100 mU/mg, 200 mU/mg, 300 mU/mg, 400 mU/mg, 500 mU/mg, 600 mU/mg, 700 mU/mg, 800 mU/mg, 900 mU/mg, 1000 mU/mg, 1100 mU/mg, 1200 mU/mg, 1300 mU/mg, 1400 mU/mg, 5 U/mg, 10 U/mg, 50 U/mg, 100 U/mg, 300 U/mg, 400 U/mg, 500 U/mg, 600 U/mg, 700 U/mg, 800 U/mg, 900 U/mg, 1000 U/mg, for example less than 979 mU/mg or less than 1256 mU/mg. In embodiments, the method as described herein further comprise diagnosing the subject with a gastrointestinal disease or at risk of a gastrointestinal disease if the level of iAP enzyme activity in the sample is less than 1500 mU/mg, 1000 mU/mg, 500 mU/mg, for example less than 1256 mU/mg.

In embodiments, the method as described herein further comprise diagnosing the subject with a gastrointestinal disease if the fecal protein level in the sample is at least two standard deviations above the mean fecal protein level of the control sample. In embodiments, the method as described herein further comprise diagnosing the subject with a gastrointestinal disease if the fecal protein level in the sample is at least 1, 1.5, 2, 2.5, 3, 3.5, 4, 4.5, 5 standard deviations above the mean fecal protein level of the control sample. In embodiments, the control sample can comprise two or more control samples. In embodiments, the method as described herein further comprise diagnosing the subject with a gastrointestinal disease or at risk of a gastrointestinal disease if the fecal protein level in the sample exceeds 1.6 mg/ml, or for example exceeds 1.8 mg/ml. In embodiments, the method as described herein further comprise diagnosing the subject with a gastrointestinal disease or at risk of a gastrointestinal disease if the fecal protein level in the sample exceeds 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml.

In embodiments, the method as described herein further comprise treating the subject. In embodiments, treating can comprise administering to the subject diagnosed with a gastrointestinal disease an effective amount of antibiotics, probiotics, intravenous fluids, steps to withhold oral feeding, an iAP replacement composition, parenteral (or intravenous) nutrition, or a combination thereof.

In embodiments, the subject can comprise a mammal. In embodiments, the mammal can comprise a dog, cat, horse, cow, pig, or human. In some embodiments, the biomarkers of the invention can be useful for diagnosing colic in horses. In embodiments, the human can comprise an infant. In embodiments, the infant can comprise a preterm infant.

The present invention further provides a method for screening the presence of a signature in a subject, such as a subject at risk of developing a gastrointestinal disease or a subject with a non-symptomatic gastrointestinal disease, comprising obtaining a sample from the subject, measuring at least one GI disease biomarker in the sample, wherein the GI disease biomarker can comprise intestinal alkaline phosphatase (iAP) protein, comparing the GI disease biomarker profile to that of a profile obtained from a control or reference sample, and treating the subject. In embodiments, the control or reference sample can comprise two or more control samples. In embodiments, the sample is a fecal sample.

The present invention further provides a method for identifying a subject at risk for a gastrointestinal disease or a subject with a non-symptomatic gastrointestinal disease comprising obtaining a sample from the subject, measuring at least one GI disease biomarker in the sample, wherein the GI disease biomarker can comprise intestinal alkaline phosphatase (iAP) protein, comparing the GI disease biomarker profile to that of a profile obtained from a control sample, and treating the subject. In embodiments, the control sample can comprise two or more control samples.

In embodiments the gastrointestinal disease can comprise colitis, inflammatory bowel disease (IBD), or a combination thereof. In embodiments, colitis can comprise necrotizing enterocolitis, adult necrotizing enterocolitis (ANEC), pseudomembranous enterocolitis, infectious colitis, ulcerative colitis, Crohn's disease, ischemic colitis, radiation colitis.

In embodiments, the sample can comprise a biological sample obtained from subject. For example, the biological sample can be a biological fluid, a biological solid, or a biological semi-solid. In embodiments, the sample can comprise fecal matter, meconium, vomit, peripheral blood, sera, plasma, or urine.

In embodiments, the GI disease biomarker further can comprise iAP enzymatic activity, total fecal protein, iAP dimerization/dissociation, post-translationally modified iAP, or a combination thereof. In embodiments, the post-translational modification can comprise acetylation, acylation, alkylation, amidation, butyrylation, deamidation, formylation, glypiation, glycosylation, hydroxylation, iodination, ISGylation, lipoylation, malonylation, methylation, myristoylation, palmitoylation, phosphorylation, phosphopantetheinylation, prenylation, propionylation, ribosylation succinylation, sulfation, SUMOylation, or ubiquitination.

In embodiments, measuring can comprise performing an assay to determine total protein concentration, intestinal alkaline phosphatase enzyme activity, intestinal alkaline phosphatase protein concentration, or a combination thereof in the sample. In embodiments, measuring can comprise a Bradford assay, a bicinchoninic acid (BCA) assay, a Lowry assay, a pyrogallol red protein dye-binding assay, a Coomassie blue dye-binding assay, or a combination thereof. In embodiments, measuring can comprise a kinetic assay. In embodiments, the kinetic assay can comprise use of 4-methylumbelliferyl phosphate, nitrophenyl phosphate, or any other fluorometric or colorimetric signal, an assay to detect ATP hydrolysis, or a combination thereof. In embodiments, measuring can comprise an immunoassay, a colorimetric assay, fluorimetric assay or a combination of both.

In embodiments, the immunoassay can comprise a western blot assay, an enzyme-linked immunosorbent assay, immunoprecipitation or a combination thereof. In embodiments, the assay can comprise an anti-iAP antibody. In embodiments, the anti-iAP antibody is a monoclonal or polyclonal antibody.

In embodiments, methods as disclosed herein can further comprise diagnosing the subject with a gastrointestinal disease when total protein concentration in the sample is at least two standard deviations above the mean of the control sample, the concentration of intestinal alkaline phosphatase protein is at least two standard deviations above the mean of the control sample, intestinal alkaline phosphatase activity is at least two standard deviations below the mean of the control sample, or a combination thereof. In embodiments, methods as disclosed herein can further comprise diagnosing the subject with a gastrointestinal disease when total protein concentration in the sample is at least 1, 1.5, 2, 2.5, 3, 3.5, 4, 4.5, 5 standard deviations above the mean of the control sample, the concentration of intestinal alkaline phosphatase protein is at least 1, 1.5, 2, 2.5, 3, 3.5, 4, 4.5, 5 standard deviations above the mean of the control sample, intestinal alkaline phosphatase activity is at least 1, 1.5, 2, 2.5, 3, 3.5, 4, 4.5, 5 standard deviations below the mean of the control sample, or a combination thereof. In embodiments, the control sample can comprise two or more control samples.

In embodiments, methods as disclosed herein can further comprise treating the subject. In embodiments, treating can comprise administering to the subject diagnosed with a gastrointestinal disease an effective amount of antibiotics, probiotics, intravenous fluids, withholding oral feeding, an iAP replacement composition, an anti-inflammatory, a potential therapeutic, parenteral (or intravenous) nutrition, or a combination thereof.

In embodiments, the subject can be diagnosed with a gastrointestinal disease or at risk of a gastrointestinal disease if the protein concentration in fecal sample is greater than about 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml, for example 1.6 mg/ml, or for example 1.8 mg/ml. In embodiments, the subject can be diagnosed with a gastrointestinal disease or at risk of a gastrointestinal disease if the iAP activity is lower than about 10 mU/mg, 20 mU/mg, 30 mU/mg, 40 mU/mg, 50 mU/mg, 60 mU/mg, 70 mU/mg, 80 mU/mg, 90 mU/mg, 100 mU/mg, 200 mU/mg, 300 mU/mg, 400 mU/mg, 500 mU/mg, 600 mU/mg, 700 mU/mg, 800 mU/mg, 900 mU/mg, 1000 mU/mg, 1100 mU/mg, 1200 mU/mg, 1300 mU/mg, 1400 mU/mg, 5 U/mg, 10 U/mg, 50 U/mg, 100 U/mg, 200 U/mg, 300 U/mg, 400 U/mg, 500 U/mg, 600 U/mg, 700 U/mg, 800 U/mg, 900 U/mg, 1000 U/mg, for example 972 mU/mg, or for example 1256 mU/mg. In embodiments, the subject can be diagnosed with a gastrointestinal disease or at risk of a gastrointestinal disease if the iAP protein detection by anti-iAP antibody exceeds 4.8% of control via densitometry. In embodiments, the subject can be diagnosed with a gastrointestinal disease if the level of iAP protein is at least two standard deviations above the mean of the control sample. In embodiments, the control sample can comprise two or more control samples. In embodiments, the subject can comprise a mammal. In embodiments, the mammal can comprise a dog, cat, horse, cow, or human. In embodiments, the human can comprise an infant. In embodiments, the infant can comprise a preterm infant.

The present invention further provides for a disposable article, the disposable article comprising a biosensor, wherein the biosensor can comprise at least one bio-recognition element, and wherein the biosensor detects iAP in a sample.

In embodiments, the biosensor further detects iAP enzymatic activity, total fecal protein, iAP dimerization/dissociation, post-translationally modified iAP, or a combination thereof. In embodiments, the post-translational modification can comprise acetylation, acylation, alkylation, amidation, butyrylation, deamidation, formylation, glypiation, glycosylation, hydroxylation, iodination, ISGylation, lipoylation, malonylation, methylation, myristoylation, palmitoylation, phosphorylation, phosphopantetheinylation, prenylation, propionylation, ribosylation succinylation, sulfation, SUMOylation, or ubiquitination.

In embodiments, the sample can comprise a biological sample obtained from subject. For example, the biological sample can be a biological fluid, a biological solid, or a biological semi-solid. In embodiments, the sample can comprise fecal matter, meconium, vomit, peripheral blood, sera, plasma, or urine.

In embodiments, the biosensor is an immunosensor. In embodiments, the biosensor can comprise a detection signal. In embodiments, the detection signal can comprise a colorimetric signal, a fluorescent signal, or both. In embodiments, the bio-recognition element can comprise an anti-iAP antibody. In embodiments, the anti-iAP antibody can comprise a polyclonal or monoclonal antibody.

In an exemplary embodiment, the biosensor can comprise lateral flow immunoassays, also known as immunochromatography assay or a strip test. Lateral flow immunoassays comprise immunoassays adapted to operate along a single axis to suit the test strip format. A typical lateral flow test strip comprises a sample pad (an adsorbent pad onto which the test sample is applied), a conjugate or reagent pad (this contains binding agents, such as antibodies, specific to the target analyte conjugate to colored particles, such as colloidal gold nanoparticles or latex microspheres), reaction membrane (typically a nitrocellulose or cellulose acetate membrane onto which anti-target analyte binding agents, such as antibodies, are immobilized in a line that crosses the membrane to act as a capture zone or test line. A control zone will also be present, containing antibodies specific for the conjugate antibodies), and a wick or waste reservoir (a further absorbent pad designed to draw the sample across the reaction membrane by capillary action and collect it). The components of the strip are usually fixed to an inert backing material and may be presented in a simple dipstick format or within a plastic casing with a sample port and reaction window showing the capture and control zones.

In embodiments, the article can comprise a diaper to be worn by a subject, wipe for cleaning a subject, dipstick, spoon, scoopula, filter paper or swab.

In embodiments, the subject can comprise a mammal. In embodiments, the mammal can comprise a dog, cat, horse, cow, or human. In embodiments, the human can comprise an infant. In embodiments, the infant can comprise a preterm infant.

The present invention further provides for a kit for diagnosing a subject with a gastrointestinal disease. In embodiments, the kit can comprise a disposable article as described herein. In embodiments, the gastrointestinal disease can comprise colitis, inflammatory bowel disease (IBD), or a combination thereof. In embodiments, colitis can comprise necrotizing enterocolitis, adult necrotizing enterocolitis (ANEC), pseudomembranous enterocolitis, infectious colitis, ulcerative colitis, Crohn's disease, ischemic colitis, radiation colitis.

In embodiments, the kit can comprise an iAP bio-recognition element immobilized to a solid support and instructions for use of same.

In embodiments, the gastrointestinal disease can comprise colitis, inflammatory bowel disease, or a combination thereof. In embodiments, colitis can comprise necrotizing enterocolitis, adult necrotizing enterocolitis (ANEC), pseudomembranous enterocolitis, infectious colitis, ulcerative colitis, Crohn's disease, ischemic colitis, radiation colitis.

In embodiments, the bio-recognition element can comprise an antibody directed to iAP or an oligonucleotide directed to iAP, for example, that is affixed directly or indirectly to a solid support. Embodiments can also comprise a fluorescent substrate or inhibitor with high binding affinity to iAP attached to the solid support.

In embodiments, the solid support can comprise plastic, cardboard, or glass. In embodiments, the solid support can comprise a dip stick.

In embodiments, the subject can comprise a mammal. In embodiments, the mammal can comprise a dog, cat, horse, cow, or human. In embodiments, the human can comprise an infant. In embodiments, the infant can comprise a preterm infant.

The present invention further provides a diagnostic kit of molecular biomarkers for identifying a subject exhibiting or having a predisposition to develop a gastrointestinal disease. In embodiments, the kit can comprise at least one of a means for determining total fecal protein concentration, a means for determining intestinal alkaline phosphatase (iAP) activity, and an iAP bio-recognition element, wherein together represent a molecular signature that is indicative of the presence of or a predisposition to development of a gastrointestinal disease in a human subject. In embodiments, the gastrointestinal disease can comprise colitis, inflammatory bowel disease (IBD), or a combination thereof. In embodiments, colitis can comprise necrotizing enterocolitis, adult necrotizing enterocolitis (ANEC), pseudomembranous enterocolitis, infectious colitis, ulcerative colitis, Crohn's disease, ischemic colitis, radiation colitis.

In embodiments, the signature can comprise total protein concentration at least two standard deviations above the mean of a control sample, intestinal alkaline phosphatase protein concentration at least two standard deviations above the mean of a control sample, or intestinal alkaline phosphatase activity at least two standard deviations below the mean of a control sample. In embodiments, the control sample can comprise two or more control samples.

In embodiments, the signature can be selected from at least two of the group comprising total protein concentration at least two standard deviations above the mean of a control sample, intestinal alkaline phosphatase protein concentration at least two standard deviations above the mean of a control sample, and intestinal alkaline phosphatase activity at least two standard deviations below the mean of a control sample. In embodiments, the control sample can comprise two or more control samples.

In embodiments, the subject can comprise a mammal. In embodiments, the mammal can comprise a dog, cat, horse, cow, or human. In embodiments, the human can comprise an infant. In embodiments, the infant can comprise a preterm infant.

Aspects of the invention are further directed towards treating an NEC-afflicted subject by altering a feeding regimen. In one embodiment, the invention provides for a method for treating an NEC-afflicted subject. In some embodiments, the method comprises measuring, in a sample obtained from the subject according to the methods described herein, the amount or activity of iAP-bound agent, wherein the iAP-bound agent is at least one GI disease biomarker comprising iAP enzymatic activity, AP enzymatic activity, iAP protein level, AP protein level, iAP dimerization/dissociation, post-translationally modified iAP, total fecal protein, or a combination thereof; determining the post-partum developmental age of the subject; and withholding enteral feeding for a period of time sufficient to resolve gastrointestinal inflammatory processes or signs of feeding intolerance. In some embodiments, the method further comprises administering an antibiotic or an antifungal, either alone or in combination. In some embodiments, the method further comprises administering a probiotic, other biologic (such as stem cells or transcription factors), or therapeutic (such as TLR4 small molecules, alkaline phosphatase inhibitors or activators), antibiotics, intravenous fluids, an iAP replacement composition (such as that provide exogenously), a small molecule activator and/or effector of catalytic activity, an anti-inflammatory, parenteral (or intravenous) nutrition, either alone or in a combination thereof. In some embodiments, the post-partum developmental age of a subject can be 'post-menstrual age' or a 'post-menstrual developmental age'.

For example, oral feeding can be withheld for 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days.

Non-limiting examples of biologics comprise stem cells and transcription factors. The small intestine epithelium is in a constant dynamic state of flux and replaces itself every 3-6 days. This continuous renewal is necessary for maintenance of normal gut structure and function. Further, non-limiting examples of transcription factors include those that can be expressed and used for enterocyte differentiation, such as the Kruppel-like factor (GKLF or KLF4) family.

In embodiments, the feeding regiment can comprise an intermittent feeding regiment. For example, during an extended period of withholding oral feeding, there may be one or more days of feed. For example, feeding can be withheld for about 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, or 30 days, during which time there may be one or more days of oral feeding. For example, a doctor may suspect NEC and withhold feeding for a short period of time, such as one day or two days, until lab tests/examinations suggest that the baby does not have NEC, at which time they would resume feeding again. Several hours or days later, there may be another NEC scare and food would be withheld from the baby again for a period of time. Intermittent feed can occur one or more times throughout a subjects stay in the hospital. Such intermittent feeding may allow the clinician to determine the tolerability to feeding of the subject. In other embodiments, intermittent feeding may be recommended for a subject at risk of developing a gastrointestinal disorder. Other objects and advantages of this invention will become readily apparent from the ensuing description.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 4 shows demographic information of the study subjects. Averages and standard deviations are shown for gestational age and birth weight. Distribution of gestational age, gender, and Bell stage is also reported.

FIG. 6 shows demographics of patient enrollment in study.

FIG. 13 shows stool samples can be heterogeneous. There were two identifiable consistency compartments in a stool sample from a NEC patient. The stool compartments were separated and western blots were run on each compartment separately with differing results.

DETAILED DESCRIPTION OF THE INVENTION

Abbreviations and Definitions

Figure 1:
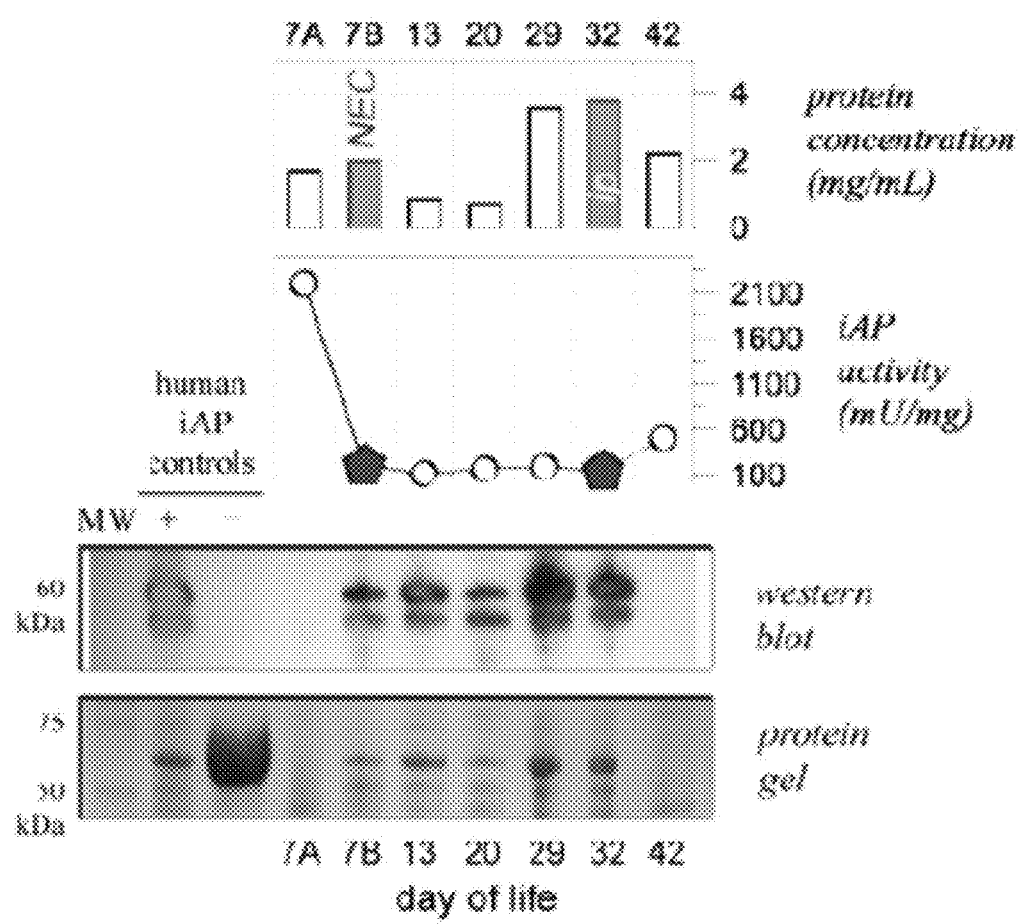
FIG. 1 shows the longitudinal measurements of total fecal protein, iAP enzymatic activity, and immunoblot detection of iAP protein is depicted for two pre-term infants. (A) Patient 1 was born at 30 weeks of gestation, developed NEC at 7 days of life, was treated medically and subsequently had recurrent NEC and an intestinal perforation on day of life 31. Infant recovered after placement of an intraperitoneal drain and 10 additional days of bowel rest and antibiotics. Red symbols and columns represent NEC episodes. 7A and 7B refer to 2 separate stool samples collected on day of life 7, one prior to and one following the diagnosis of NEC. (B) Patient 2 was born at 25 weeks of gestation, developed abdominal distension, suspicious for NEC, on DOL 19 (green symbol and column). Infant responded quickly to medical management and enteral feedings were soon resumed. Patient developed definite NEC (red symbol and column) on DOL 32, requiring assisted ventilation and aggressive medical management, but recovered fully by DOL 48. The tables below each figure illustrate which fecal assays met the criteria for NEC (+) and which did not (−). These criteria were defined by values outside the 95% confidence interval for control values. Risk for NEC was considered increased if: protein concentration exceeded 1.8 mg/ml; iAP activity was less than 979 mU/mg; or iAP protein detection by western blot exceeded 10.7% of control. Abbreviations: ip, intestinal perforation; ad, abdominal distension; MW, molecular weight ladder; and kDa, kilodalton.

Detailed descriptions of one or more preferred embodiments are provided herein. It is to be understood, however, that the present invention can be embodied in various forms. Therefore, specific details disclosed herein are not to be interpreted as limiting, but rather as a basis for the claims and as a representative basis for teaching one skilled in the art to employ the present invention in any appropriate manner.

The singular forms "a", "an" and "the" include plural reference unless the context clearly dictates otherwise. The use of the word "a" or "an" when used in conjunction with the term "comprising" in the claims and/or the specification can mean "one," but it is also consistent with the meaning of "one or more," "at least one," and "one or more than one."

Wherever any of the phrases "for example," "such as," "including" and the like is used herein, the phrase "and without limitation" is understood to follow unless explicitly stated otherwise. Similarly "an example," "exemplary" and the like are understood to be nonlimiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

The present invention is directed to compositions and methods to detect and treat gastrointestinal diseases.

Gastrointestinal Diseases

Gastrointestinal diseases refer to diseases involving the gastrointestinal tracts. For example, necrotizing enterocolitis (NEC) is an acquired gastrointestinal disease often seen in pre-term infants. In NEC, bacteria invade the wall of the intestine, causing local infection and inflammation. NEC is characterized by high mortality and long-term morbidity, including short gut syndrome, recurrent infection, nutritional deficiency and neurodevelopmental delay. Despite an overall net decrease in mortality for premature infants, there has been an increase in NEC-associated deaths. NEC is often difficult to diagnose and manage, due to initial nonspecific symptomatology and rapid deterioration.

In addition to necrotizing enterocolitis seen in neonates and preterm neonates, necrotizing enterocolitis can also affect non-neonates. For example, necrotizing enterocolitis in non-neonates, such as adults, can result from inflammatory mediators; nutritional disorders, such as anorexia or significant weight loss; gastrointestinal dysfunction; alcoholism; malabsorption; agents that block intestinal proteases; smoking; circulatory disturbances, such as reduced mesenteric blood flow, bowel ischemia, atherosclerosis of the bowel arteries; cholelithiasis; administration of drugs; immunological deficiencies, such as of the IgA secretory component or intestinal T-lymphocytes coupled with poor antibody response; fecal impaction or constipation; or infectious agents, such as bacterial infections, food borne infections and food borne illnesses.

Non-limiting examples of such drugs include those with anticholinergic properties, such as neuroleptics or phenothiazine-based neuroleptics, narcotics, inflammatory mediators, antidepressants, iron pills, laxatives, or antacids.

Non-limiting examples of such infectious agents comprise bacteria like *Klebsiella, E. coli, Enterobacter, Pseudomonas*, Clostridia and *Staphylococcus epidermidis*, viruses like Corona virus, Rota virus and Entero virus and rarely, fungi like *Candida albicans*. Enteropathogenic viruses are believed to infect epithelial cells resulting in cell destruction, necrosis and intestinal perforation.

Constipation or fecal impact can have many different causes known to art, non-limiting examples of which include antacid medicines containing calcium or aluminum, changes in diet or activities, colon cancer, dairy products, eating disorders, neurological conditions, inactivity, dehydration, consuming fiber, overuse of laxatives, pregnancy, digestive disorders, resisting the urge to have a bowel movement, medications, stress, or hypothyroidism.

Aspects of the invention pertain to gastrointestinal diseases. Gastrointestinal diseases refer to diseases involving the gastrointestinal tract, namely the esophagus, stomach, small intestine, large intestine and rectum, and the accessory organs of digestion, the liver, gallbladder, and pancreas. For example, such diseases can result from infectious, autoimmune, and physiological states. Non-limiting examples of gastrointestinal diseases include colitis, inflammatory bowel disease (IBD), gastritis, gastroenteritis, pyloric stenosis, gastric cancer, infectious diarrhea, fecal impaction, constipation, intestinal obstruction and pseudo-obstruction, or malabsorption. In addition to necrotizing enterocolitis (NEC), non-limiting examples of types of colitis comprise adult necrotizing enterocolitis (ANEC), pseudomembranous enterocolitis, infectious colitis, ulcerative colitis, Crohn's disease, ischemic colitis, radiation colitis.

Intestinal Alkaline Phosphatase (iAP)

Using a single 100-150 mg stool sample from three healthy human donors, 234 human proteins, secreted from the gastrointestinal tract, were identified. Of these, a core proteome of 57 proteins, common between these three human individuals, was identified. Despite the reproducible presence of this core proteome, the relative abundance of most shared proteins varied between the three human subjects, suggestive that the core proteome can be used for identification of host-specific proteomic signatures.

Intestinal alkaline phosphatase (iAP) is expressed in small intestinal enterocytes, co-secreted into the intestinal lumen and systemic circulation and plays an integral role in maintaining gut barrier function by detoxifying bacterial lipopolysaccharides and maintaining microbial homeostasis. As the primary alkaline phosphatase in stool, iAP has been identified as one of the 57 proteins in the core human stool proteome.

Aspects of the invention pertain to methods for diagnosing a gastrointestinal disease in a subject. For example, the method comprises the steps of obtaining a sample from the subject; detecting the presence of at least one GI disease biomarker in the sample, wherein the GI disease biomarker comprises intestinal alkaline phosphatase (iAP) protein; comparing the GI disease biomarker profile to that of a profile obtained from a control sample; and treating the subject. Embodiments can also be directed towards preventing the progression of a gastrointestinal disease in a subject in need thereof, and ameliorating the symptoms associated with a gastrointestinal disease in a subject in need thereof. In embodiments, the control sample can comprise a two or more control samples.

As used herein, "changed as compared to a control" sample or subject is understood as having a level of the analyte or diagnostic or therapeutic indicator (e.g., marker such as iAP) to be detected at a level that is statistically different than a sample from a normal, untreated, or abnormal state control sample. Determination of statistical significance is within the ability of those skilled in the art, e.g., the number of standard deviations from the mean that constitute a positive or negative result and the statistical analyses to arrive at these intervals.

If a subject is diagnosed with a GI disease, embodiments of the invention comprise treating the subject. For example, treating the subject can comprise administering to the subject an effective amount of antibiotics, probiotics, intravenous fluids, an iAP replacement composition, parenteral (or intravenous) nutrition, or a combination thereof. An additional therapeutic approach can be withholding food from the subject. Non-limiting examples of an iAP replacement composition comprise gene or protein replacement compositions.

The term "administration" or "administering" can refer to introducing a substance, such as iAP protein or an antibiotic and/or an antifungal, into a subject. In general, any route of administration can be utilized including, for example, intracoronarilly, intramyocardially, intravenously, intraarterially, or any combination thereof. For example, the iAP can be administered to the subject prior to, concurrent with, or subsequent to diagnosis of a GI disease such as NEC.

Protein therapy can be accomplished by any method that effectively introduces iAP protein or a fragment thereof into the subject to restore or enhance iAP activity. An effective amount of an iAP protein (for example an amount sufficient to reduce or eliminate the symptoms associated with gastrointestinal diseases) can be administered alone or in association with an agent that facilitates the administration or activity of the protein. The "effective amount" can be determined by one of skill in the art based on such factors as the type and severity of symptoms being treated, the weight and/or age of the subject, the previous medical history of the subject, and the selected route for administration of the agent.

In embodiments, iAP protein can be associated with lipids, such as detergents or other amphipathic molecule micelles, membrane vesicles, liposomes, virosomes, or microsomes. Lipid compositions that are naturally fusogenic or can be engineered to become fusogenic (e.g. by incorporating a fusion protein into the lipid) are especially preferred. Fusion proteins can be obtained from viruses such as parainfluenza viruses 1-3, respiratory syncytial virus (RSV), influenza A, Sendai virus, and togavirus fusion protein. Nonviral fusion proteins include normal cellular proteins that mediate cell-cell fusion. Other nonviral fusion proteins include the sperm protein PH-30 which is an integral membrane protein located on the surface of sperm cells that is believed to mediate fusion between the sperm and the egg. Still other nonviral fusion proteins include chimeric PH-30 proteins such as PH-30 and the binding component of hemaglutinin from influenza virus and PH-30 and a disintegrin (e.g. bitistatin, barbourin, kistrin, and echistatin). In addition, lipid membranes can be fused using traditional chemical fusogens such as polyethylene glycol (PEG).

In embodiments, a subject can be treated by administration of an effective amount of iAP protein, optionally in a pharmaceutically acceptable carrier or diluent. An effective amount of iAP protein can be an amount sufficient to alleviate the symptoms of a gastrointestinal disease. iAP can be administered subcutaneously, intravenously, intraperitoneally, intramuscularly, parenterally, orally, submucosally, by inhalation (for example of an aerosolized pharmaceutical composition), or other appropriate route of administration in an effective dosage range. If necessitated by a particular mode of administration, iAP can be encapsulated within a material that protects it from enzymatic degradation. In addition, prior to administration, it can be useful to administer agents to clear bacterial infection.

Alternatively, a preparation of the gene encoding iAP or a fragment thereof can be incorporated into a suitable vector for delivering the gene into a subject's cells. In embodiments, the iAP gene therapy can be transient and require repeated delivery to the subject. In other embodiments, gene therapy can offer a cure for the gastrointestinal disease. For example, if genetic material encoding iAP is incorporated into stem cells of a subject, all subsequent generations of such cells can make authentic iAP from the integrated sequences and would correct the defect. Non-limiting examples of approaches and vectors that can be useful for performing iAP gene therapy include retroviruses, adeno-associated viruses, naked DNA, DNA-lipid complexes, receptor mediated entry, or adenovirus.

Non-limiting modes of administration of treatment comprise intravenous (IV); intramucosal; intramuscular; subcutaneously, and non-invasive modes of administration, such as oral, intranasal, buccal, intrapulmonary, intrabronchial, and transdermal.

Aspects of the invention further pertain to methods for screening for the presence of a signature in a subject at risk of developing a gastrointestinal disease or a subject with a non-symptomatic gastrointestinal disease. For example, steps of the method comprise obtaining a sample from the subject; measuring at least one GI disease biomarker in the sample, wherein the GI disease biomarker comprises intestinal alkaline phosphatase (iAP) protein; comparing the GI disease biomarker profile to that of a profile obtained from a control sample; and treating the subject. Similarly, aspects can also be directed towards methods for identifying a subject at risk for a gastrointestinal disease or a subject with a non-symptomatic gastrointestinal disease. In embodiments, the control sample can comprise two or more control samples.

Aspects of the invention comprise measuring total protein concentration in a sample, intestinal alkaline phosphatase protein concentration in a sample, intestinal alkaline phosphatase enzyme activity in a sample, or a combination thereof. Samples used in such methods, and assays used to collect such measurements are described herein. For example, a subject can be diagnosed as having a GI disease if the protein concentration in the sample is greater than about 1.0 mg/ml, 1.1 mg/ml, 1.2 mg/ml, 1.3 mg/ml, 1.4 mg/ml, 1.5 mg/ml, 1.6 mg/ml, 1.7 mg/ml, 1.8 mg/ml, 1.9 mg/ml, 2.0 mg/ml, 2.1 mg/ml, 2.2 mg/ml, 2.3 mg/ml, 2.4 mg/ml, 2.5 mg/ml, 2.6 mg/ml, 2.7 mg/ml, 2.8 mg/ml, 2.9 mg/ml, 3.0 mg/ml, 3.1 mg/ml, 3.2 mg/ml, 3.3 mg/ml, 3.4 mg/ml, 3.5 mg/ml, 3.6 mg/ml, 3.7 mg/ml, 3.8 mg/ml, 3.9 mg/ml, 4.0 mg/ml, 4.1 mg/ml, 4.2 mg/ml, 4.3 mg/ml, 4.4 mg/ml, 4.5 mg/ml, 4.6 mg/ml, 4.7 mg/ml, 4.8 mg/ml, 4.9 mg/ml, 5.0 mg/ml. As another example, a subject can be diagnosed as having a GI disease if the iAP activity is lower than about 10 mU/mg, 20 mU/mg, 30 mU/mg, 40 mU/mg, 50 mU/mg, 60 mU/mg, 70 mU/mg, 80 mU/mg, 90 mU/mg, 100 mU/mg, 200 mU/mg, 300 mU/mg, 400 mU/mg, 500 mU/mg, 600 mU/mg, 700 mU/mg, 800 mU/mg, 900 mU/mg, 1000 mU/mg, 1100 mU/mg, 1200 mU/mg, 1300 mU/mg, 1400 mU/mg, 5 U/mg, 10 U/mg, 50 U/mg, 100 U/mg, 200 U/mg, 300 U/mg, 400 U/mg, 500 U/mg, 600 U/mg, 700 U/mg, 800 U/mg, 900 U/mg, 1000 U/mg. For example, a subject can be diagnosed with a gastrointestinal disease if the protein concentration in fecal sample is greater than about 1.6 mg/ml, or greater than about 1.8 mg/ml; if the iAP activity is lower than about 979 mU/m, or lower than about 1256 mU/mg; or if the level of iAP protein is at least two standard deviations above the mean of the control sample. As another example, a subject can be diagnosed as having a GI disease if the level of iAP protein is greater than about 0.05%, 1%, 2%, 3%, 4%, 5%, 6%, 7%, 8%, 9%, 10%, 20%, 30%, 40%, 50%, 60%, 70%, 80%, 90%, 100%, 125%, 150%, 175%, 200%, 225%, 250%, 275% of a control sample. For example, the subject can be diagnosed with a gastrointestinal disease if the iAP protein detection by anti-iAP antibody exceeds 10.7 of control via densitometry, or in excess of 4.8% of control via densitometry. In other embodiments, a subject can be diagnosed with a gastrointestinal disease if two of the thresholds are met, or if all three thresholds are met. In embodiments, the control sample can comprise a two or more control samples.

The term "threshold", for example a threshold indicative of NEC, refers to a value derived from a plurality of biological samples, such as donor stool samples, for a biomarker, such as iAP protein levels, iAP catalytic activity, or total fecal protein levels, above which threshold is associated with an increased likelihood of having and/or developing a gastrointestinal disease such as NEC.

Embodiments of the invention comprise diagnosing the subject with a gastrointestinal disease if the protein level of iAP in the sample, the level of iAP enzyme activity in the sample, or the fecal protein level is at least 0.5, 1, 1.5, 2, 2.5, 3, 3.5, 4, 4.5, 5, or 10 standard deviations above the mean level of the control sample. In other embodiments, a subject can be diagnosed with a gastrointestinal disease if two of the thresholds are met, or if all three thresholds are met. In embodiments, the control sample can comprise two or more control samples.

Embodiments of the invention comprise machine learning techniques or applications to determine appropriate clinical thresholds. For example, such techniques comprise those known to the field, including Naïve Bayes classifiers (NBC), linear discriminant analysis (LDA), or support vector machines (SVM). and support vector machine options. One of skill in the art readily understands that such a threshold value can vary depending on the sample size analyzed and the statistical analyses employed.

Aspects of the invention further comprise identifying and/or diagnosing both early stages of gastrointestinal disease and advanced stages of gastrointestinal disease. Certain embodiments can distinguish between early stage and late stage gastrointestinal disease. For example, embodiments as described herein can diagnose advanced states of inflammation, such as that identified by radiological findings of pneumatosis intestinalis (portal vein or biliary gas). As another example, embodiments can identify early stages of the disease before rampant inflammation of the gut is physiologically evident. Physicians currently suspect gastrointestinal disease from a range of physical signs, such as abdominal distension, abdominal tenderness, decreased bowel sounds, blood in stools, increased apnea, temperature instability, bilious aspirates, and feeding intolerance. Clinical signs for suspecting disease are dilated intestinal loops and thickened bowel walls from radiology. Laboratory findings for suspecting disease are decreased platelets, decreased or increased white blood cell count, increased band count, and metabolic acidosis. Embodiments can match identification of radiological findings of pneumatosis intestinalis (portal vein or biliary gas) in advanced stages of inflammation. The method also identifies early stages of the disease before rampant inflammation of the gut is physiologically evident.

Samples

Aspects of the invention comprise measuring or detecting biomarkers of gastrointestinal diseases in biological samples. Biomarkers of the invention can be measured in different types of biological samples. Non-limiting examples of biological samples that can be used in methods of the invention, although not intended to be limiting, include stool, plasma, cord blood, neonatal blood, cerebral spinal fluid, tears, vomit, saliva, urine, feces, and meconium. If desired, a sample can be prepared to enhance detectability of the biomarkers. For example, a sample from the subject can be fractionated. Any method that enriches for a biomarker polypeptide of interest can be used. Sample preparations, such as prefractionation protocols, are optional and may or may not be necessary to enhance detectability of biomarkers depending on the methods of detection used. For example, sample preparation can be unnecessary if an antibody that specifically binds a biomarker is used to detect the presence of the biomarker in a sample. Sample preparation can involve fractionation of a sample and collection of fractions determined to contain the biomarkers. Methods of prefractionation include, for example, size exclusion chromatography, ion exchange chromatography, heparin chromatography, affinity chromatography, sequential extraction, gel electrophoresis, mass spectrometry, and liquid chromatography.

The methods described herein can involve obtaining a biological sample from the subject, such as an infant. As used herein, the phrase "obtaining a biological sample" refers to any process for directly or indirectly acquiring a biological sample from a subject. For example, a biological sample can be obtained (e.g., at a point-of-care facility, such as a physician's office, a hospital, laboratory facility) by procuring a tissue or fluid sample (e.g., blood draw, marrow sample, spinal tap) from a subject. Alternatively, a biological sample can be obtained by receiving the biological sample (e.g., at a laboratory facility) from one or more persons who procured the sample directly from the subject. The biological sample can be, for example, feces, such as stool, a tissue (e.g., blood), cell (e.g., hematopoietic cell such as hematopoietic stem cell, leukocyte, or reticulocyte, stem cell, or plasma cell), vesicle, biomolecular aggregate or platelet from the subject.

Assays and Antibodies

Aspects of the invention comprise biomarkers of GI disease. For example, aspects comprise biomarkers of necrotizing enterocolitis. For example, biomarkers of GI disease comprise iAP enzymatic activity, iAP protein level, iAP dimerization/dissociation, post-translationally modified iAP, total fecal protein, or a combination thereof.

Aspects of the invention comprise an assay that measures iAP enzymatic activity. Aspects of the invention comprise an assay that measures iAP protein level. Aspects of the invention comprise an assay that measures iAP dimerization/dissociation. Aspects of the invention comprise an assay that measures post-translationally modified iAP. Aspects of the invention comprise an assay that measures total fecal protein.

Non-limiting examples of post-translational modifications comprises acetylation, acylation, alkylation, amidation, butyrylation, deamidation, formylation, glypiation, glycosylation, hydroxylation, iodination, ISGylation, lipoylation, malonylation, methylation, myristoylation, palmitoylation, phosphorylation, phosphopantetheinylation, prenylation, propionylation, ribosylation succinylation, sulfation, SUMOylation, or ubiquitination.

iAP is a homodimer; each protomer binds 4 divalent ($Zn^{2+}$ and $Mg^{2+}$) ions, which are essential in maintaining the structural integrity and catalytic activity of the enzymes. iAP is one of four different alkaline phosphatases found in human tissue that has been correlated with physiological function. Although it is found in high concentrations within luminal vesicles secreted by enterocytes on the microvilli brush border, small levels of iAP are released into the blood as well as the gut lumen, where in the latter travel throughout the intestinal tract.

Embodiments of the invention comprise measuring or detecting such biomarkers using assays known to the art. Non-limiting examples of assays include an immunoassay, a colorimetric assay, fluorimetric assay or a combination thereof. Non-limiting examples of immunoassays comprise a western blot assay, an enzyme-linked immunosorbent assay (ELISA), immunoprecipitation or a combination thereof. For example, a biological sample collected from a subject can be incubated together with a biomarker specific antibody, such as an anti-iAP antibody or fragment thereof, and the binding of the antibody to the biomarker in the sample is detected or measured.

In embodiments, the antibody or fragment thereof can be specific for iAP (anti-iAP). The antibody can be a polyclonal antibody or a monoclonal antibody. The antibody or fragment thereof can be attached to a molecule that is capable of identification, visualization, or localization using known methods. Suitable detectable labels include radioisotopic labels, enzyme labels, non-radioactive isotopic labels, fluorescent labels, toxin labels, affinity labels, and chemiluminescent labels.

Examples of assays that can be used in methods of the invention, although not intended to be limiting, comprise a Bradford assay, a bicinchoninic acid (BCA) assay, a Lowry assay, a pyrogallol red protein dye-binding assay, a Coomassie blue dye-binding assay, an endpoint assay, a kinetic assay, such as a kinetic assay using a fluorometric substrate such as 4-methylumbelliferyl phosphate, chemiluminescent substrates such as CSPD and CDP-Star, DynaLight Substrate with RapidGlow enhancer, or colorimetric 4-nitrophenyl phosphate, an assay to detect phosphatase reactions, an assay to detect ATP hydrolysis, or a combination thereof. In embodiments, the assays can be provided in a multi-well format, such as a 6-, 12-, 24-, 48- or 96-well plate. In embodiments, the assays can be provided in a standard cuvette, such as a 1 ml cuvette.

Total protein, such as total fecal protein, can be measured by assays known to one skilled in the art (see page 7, 27 and 85, for example, of Cardinal Health catalogue, Dublin, Ohio, 2013, which is incorporated by reference herein in its entirety, see Roche Total Protein/TP2, Cobas c502 TPUC3, or Abbott's Total Protein kit). For example, Pyrogallol Red Molybdate dye binding method provides a colorimetric method for total protein quantitation with greater linearity, using microliter volumes of biological samples in manual or automated systems. As described herein, pyrogallol red can be provided in a kit comprising reagent, controls, and reagent standards, such as 25 mg/dL, 50 mg/dL, 100 mg/dL, and 200 mg/dL.

The enzyme employed in embodiments herein, for example to detect protein levels or enzymatic activity, can be, for example, alkaline phosphatase, horseradish peroxidase, β-galactosidase and/or glucose oxidase; and the substrate can respectively be an alkaline phosphatase, horseradish peroxidase, β-galactosidase or glucose oxidase substrate (see *Molecular Probes Handbook—A Guide to Fluorescent Probes and Labeling Technologies,* 11th Edition (2010), Invitrogen, which is incorporated by reference herein in its entirety).

In embodiments, the enzyme, such as alkaline phosphatase or horseradish peroxidase, can be attached to a secondary antibody. Without being bound by theory, measurement of alkaline phosphatase can be confounded by signal from secondary antibodies. Isolated alkaline phosphatase can catalytically hydrolyze MUP to form the fluorescent product MU. Secondary antibodies, conjugated to AP, from two different commercial manufacturers, for example, can also hydrolyze MUP to form fluorescent product. When both alkaline phosphatase protein and the secondary antibody are in the same measurement, there is an increased level of catalytic activity observed. This activity can be monitored by both standard spectrophotometric readings of biochemical activity and by Western blot.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color).

Horseradish Peroxidase (HRP, sometimes abbreviated PO) substrates include, but are not limited to, 2,2' Azino-di-3-ethylbenz-thiazoline sulfonate (ABTS, green, water soluble), aminoethyl carbazole, 3-amino, 9-ethylcarbazole AEC (3A9EC, red). Alpha-naphthol pyronin (red), 4-chloro-1-naphthol (4C1N, blue, blue-black), 3,3'-diaminobenzidine tetrahydrochloride (DAB, brown), ortho-dianisidine (green), o-phenylene diamine (OPD, brown, water soluble), TACS Blue (blue), TACS Red (red), 3,3',5,5' Tetramethylbenzidine (TMB, green or green/blue), TRUE BLUE™ (blue), VECTOR™ VIP (purple), VECTOR™ SG (smoky blue-gray), and Zymed Blue HRP substrate (vivid blue).

Glucose Oxidase (GO) substrates, include, but are not limited to, nitroblue tetrazolium (NBT, purple precipitate), tetranitroblue tetrazolium (TNBT, black precipitate), 2-(4-iodophenyl)-5-(4-nitrophenyl)-3-phenyltetrazolium chloride (INT, red or orange precipitate), Tetrazolium blue (blue), Nitrotetrazolium violet (violet), and 3-(4,5-dimethylthiazol-2-yl)-2,5-diphenyltetrazolium bromide (MTT, purple). All tetrazolium substrates require glucose as a co-substrate. The glucose gets oxidized and the tetrazolium salt gets reduced and forms an insoluble formazan which forms the color precipitate.

Beta-Galactosidase substrates, include, but are not limited to, 5-bromo-4-chloro-3-indolyl beta-D-galactopyranoside (X-gal, blue precipitate).

Other examples of alkaline and acid phosphatase substrates comprise 9H-(1,3-dichloro-9,9-dimethylacridin-2-one-7-yl) phosphate, diammonium salt (DDAO phosphate), 6,8-difluoro-4-methylumbelliferyl phosphate (DiFMUP), fluorescein diphosphate, tetraammonium salt (FDP), 4-methylumbelliferyl phosphate, free acid (MUP), and 4-methylumbelliferyl phosphate, dicyclohexylammonium salt, trihydrate (MUP DCA salt).

Alkaline phosphatase activity, such as intestinal alkaline phosphatase activity, can be detected and/or measured with use of chromogenic substrates and/or fluorogenic substrates of alkaline phosphatases. For example, 4-methylumbelliferyl phosphate (MUP) is a fluorogenic substrate for alkaline phosphatases, and alkaline phosphatase mediated hydrolysis of its phosphate substituent yields the blue-fluorescent 4-methylumbelliferyl (excitation/emission ~386/448 nm). In embodiments, the alkaline phosphatase substrate can be directly admixed with the biological sample, such as stool, allowing for the direct detection of the presence of alkaline phosphatase or the measurement of its activity.

Alkaline phosphatase (AP) substrates include, but are not limited to, AP-Blue substrate (blue precipitate, Zymed catalog p. 61); AP-Orange substrate (orange, precipitate, Zymed), AP-Red substrate (red, red precipitate, Zymed), 5-bromo, 4-chloro, 3-indolyphosphate (BCIP substrate, turquoise precipitate), 5-bromo, 4-chloro, 3-indolyl phosphate/nitroblue tetrazolium/iodonitrotetrazolium (BCIP/INT substrate, yellow-brown precipitate, Biomeda), 5-bromo, 4-chloro, 3-indolyphosphate/nitroblue tetrazolium (BCIP/NBT substrate, blue/purple), 5-bromo, 4-chloro, 3-indolyl phosphate/nitroblue tetrazolium/iodonitrotetrazolium (BCIP/NBT/INT, brown precipitate, DAKO, Fast Red (Red), Magenta-phos (magenta), Naphthol AS-BI-phosphate (NABP)/Fast Red TR (Red), Naphthol AS-BI-phosphate (NABP)/New Fuchsin (Red), Naphthol AS-MX-phosphate (NAMP)/New Fuchsin (Red), New Fuchsin AP substrate (red), p-Nitrophenyl phosphate (PNPP, Yellow, water soluble), VECTOR™ Black (black), VECTOR™ Blue (blue), VECTOR™ Red (red), Vega Red (raspberry red color).

Other substrates known in the art, including those described herein, can be used with embodiments of the invention (see *Molecular Probes Handbook—A Guide to Fluorescent Probes and Labeling Technologies,* 11th Edition (2010), Invitrogen, which is incorporated by reference herein in its entirety). Further, as desired, various fluorophores known in the art can be covalently attached to the substrate, such as MUP.

Enzyme reactions can provide a highly specific, rapid and sensitive assay for detection of specific proteins in a sample, such as iAP in stool. Examples of suitable fluorogenic substrates which can be utilized within the present invention comprise Fluorescein diacetate, 4-Methylumbelliferyl acetate, 4-Methylumbelliferyl casein, 4-Methylumbelliferyl-α-L-arabinopyranoside, 4-Methylumbelliferyl-β-D-fucopyranoside, 4-Methylumbelliferyl-α-L-fucopyranoside, 4-Methylumbelliferyl-β-L-fucopyranoside, 4-Methylumbelliferyl-α-D-galactopyranoside, 4-Methylumbelliferyl-β-D-galactopyranoside, 4-Methylumbelliferyl-α-D-glucopyranoside, 4-Methylumbelliferyl-β-D-glucopyranoside, 4-Methylumbelliferyl-β-D-glucuronide, 4-Methylumbelliferyl nonanoate, 4-Methylumbelliferyl oleate, 4-Methylumbelliferyl phosphate, bis(4-Methylumbelliferyl)phosphate, 4-Methylumbelliferyl pyrophosphate diester, 4-Methylumbelliferyl-β-D-xylopyranoside.

Non-limiting examples of suitable chromogenic substrates for use within the present invention comprise o-Nitrophenyl-β-D-galactopyranoside, p-Nitrophenyl-β-D-galactopyranoside, o-Nitrophenyl-β-D-glucopyranoside, p-Nitrophenyl-α-D-glucopyranoside, p-Nitrophenyl-β-D-glucopyranoside, p-Nitrophenyl-β-D-glucuronide, p-Nitrophenyl phosphate, o-Nitrophenyl-β-D-xylopyranoside, p-Nitrophenyl-α-D-xylopyranoside, p-Nitrophenyl-β-D-xylopyranoside, and Phenolphthalein-β-D-glucuronide.

Subjects

As described herein, embodiments of the invention comprise measuring or detecting a gastrointestinal biomarker in a subject. The term "subject" or "patient" can refer to any organism to which aspects of the invention can be administered, e.g., for experimental, diagnostic, prophylactic, and/or therapeutic purposes. Typical subjects to which compounds of the present disclosure can be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. The term "living subject" refers to a subject noted above or another organism that is alive. The term "living subject" refers to the entire subject or organism and not just a part excised (e.g., a liver or other organ) from the living subject.

In embodiments herein, a subject comprises a mammal, such as a human or vertebrate animal. Examples of such include but are not limited to a dog, cat, horse, cow, pig, sheep, goat, chicken, primate, e.g., monkey, fish (aquaculture species), e.g. salmon, rat, and mouse. A human comprises a preterm neonate, an infant, a child, an adolescent, an adult, or an elderly individual.

Although aspects of the invention as described herein relate to human gastrointestinal disorders, aspects of the invention are also applicable to other nonhuman vertebrates. Aspects of the invention are applicable for veterinary use, such as with domestic animals. In general, aspects will vary according to the type of use and mode of administration, as well as the particularized requirements of individual subjects.

In embodiments, the subject can be on an antibiotic regimen. The term "antibiotic regimen" refers to the treatment or prevention of a disease, such as an infection, or method for achieving a desired change, such as the reducing or prevention of an infection, wherein said treatment comprises administering to a subject an antibiotic to effectively treat the disease or produce the physiological change. An antibiotic regimen can comprise variations known to those skilled in the art, such as antibiotic choice (for example, comprises correct medication choice, route of administration and dosing schedule), timing of administration, and duration. Non-limiting examples of such antibiotics comprise Vancomycin, Ampicillin, Zosyn (combination of piperacillin and tazobactam), Gentamycin, Flagyl (metronidazole generic), Meropenem, Metronidazole, Cefotaxime, Clindamycin, or any combination thereof. In some embodiments, an antifungal agent can further be administered. In other embodiments, the antifungal agent can be Fluconazole, Terconazole, Voriconazole, Posaconazole, Pentamidine, Itraconazole, Ketoconazole. In embodiments, methods as disclosed herein can further comprise treating the subject. In embodiments, treating can comprise administering to the subject diagnosed with a gastrointestinal disease an effective amount of antibiotics, probiotics, intravenous fluids, withholding oral feeding, an iAP replacement composition, parenteral (or intravenous) nutrition, or a combination thereof.

In an embodiment, such as a subject afflicted with NEC, antibiotics can be administered to a subject for a sufficient period of time, such as 10-14 days where antibiotics are administered to the infant. For other embodiments, such as a subject with sepsis, 7 days of antibiotics can be administered to the patient. For example, antibiotic administration and/or prescription can be for broad spectrum coverage, such as for (i) gram-positive bacteria, (ii) gram-negative bacteria, and (iii) anaerobic bacteria. Non-limiting examples of such regimens comprise Vancomycin (gram-positive including MRSA), ceftazidime (third generation cephalosporins—gram negative, some grant positive, and *Pseudomonas*), metronidazole (anaerobic coverage), oxacillin (gram positive). Non-limiting examples of general antibiotics regimes comprise ampicillin+gentamicin for possible vertically acquired infection from mother, and vancomycin+cetazidime for possible hospital acquired infections. From 46 neonatologist responses at the NEC symposium in April 2017, commonly used antibiotics/antifungals for NEC treatment are Gentamycin (32%), Vancomycin (28%), Ampicillin (25%), Zosyn (combination of piperacillin and tazobactam; 15%), Flagyl (metronidazole generic; 19%), Clindamycin (6%), Meropenem (4%), Fluconazole (antifungal agent, 7%), and other (1%).

In some embodiments, probiotics also can be administered to the subject. As used herein, probiotics refers to mono- or mixed cultures of live microorganisms that can help reestablish normal flora in the GI tract. Probiotics can enhance the immune response, elicit production of enzymes that degrade toxins and/or block attachment sites to the colon. See, See McFarland, *J. Medic. Microbiol.* 2005, 54:101-111. Non-limiting examples of probiotic organisms include those in the genera Bifidobacteria, *Lactobacillus, Lactococcus,* and *Pediococcus, Saccharomyces boulardii,* and related bacteria and yeast.

In some embodiments, intravenous fluids or intravenous therapy can be administered to the subject. Intravenous therapy can refer to the infusion of liquid substances directly into the vein of a subject. Non-limiting examples of such fluids comprise saline (such as 0.9% NaCl in water or 0.45% saline in water), Lactated Ringer's (0.9% NaCl with electrolytes and buffer), $D_5W$ (5% dextrose in water), $D_5NS$ (5% dextrose in 0.9% saline), $D_5$ ½ NS (5% dextrose in 0.45% saline), $D_5LR$ (5% dextrose in Lactated Ringer's), or Normosol-R. In embodiments, the solution can be isotonic. In other embodiments, the solution can be hypotonic.

In some embodiments, parenteral (or intravenous) nutrition can be administered to the subject. Non-limiting examples of parenteral (or intravenous) nutrition comprise intravenous dextrose solutions, intravenous amino acid solutions, intravenous fat emulsions, intravenous vitamin and mineral supplements, or a combination thereof.

In embodiments, feeding, such as oral feeding, can be withheld from the subject until feeding tolerance can be demonstrated. For example, feeding tolerance can be demonstrated when the preterm infant is capable of safely ingesting and digesting the prescribed enteral (via mouth) feeding without complications associated with gastrointestinal dysfunction or infection. Clinical evidence of feeding tolerance in very low birth weight preterm infant can include the number of days required to reach full-feeding volumes (reported ranged from 100-160 mL per kg per day), the number of episodes of feeding intolerance, the number of days feeds are withheld due to feeding intolerance symptoms, time to regain birth weight, lower leg growth, increase in weight gain, occipital-frontal head circumference, and length.

In embodiments, feeding refers to the intake of infant formula, such as EleCare (Abbott Nutrition), Neosure (Similac), EnfaCare (Enfamil), Pregestimil (Enfamil), Similac Special Care or SSC (Similac), Gentlease (Enfamil). Feeding can also refer to the intake of supplements, such as Microlipid (Nestle Health Science).

In embodiments, iAP replacement therapy can refer to protein replacement therapy. The term "protein replacement" can refer to the introduction of a non-native, purified protein, such as iAP, into an individual having a deficiency in such protein. The administered protein can be obtained from natural sources or by recombinant expression. The term also refers to the introduction of a purified protein in an individual otherwise requiring or benefiting from administration of a purified protein, e.g., suffering from protein insufficiency. The introduced protein can be a purified, recombinant protein produced in vitro, or protein purified from isolated tissue or fluid, such as, e.g., placenta or animal milk, or from plants. For example, Bifidobacteria, *Klebsiella*, and *E. Coli* alkaline phosphatases are also detected in human stool from preterm infants (Swittink et al. 2017. Metaproteomics reveals functional differences in intestinal microbiota development of preterm infants. Molecular & Cellular Proteomics. DOI: 10.1074/mcp.RA117.000102 (in press)), and can thus be sources of iAP protein for protein replacement therapy. Thus, in embodiments, increased AP activity can be a result of bacterial flora, and not from human iAP only.

Disposable Article

Aspects of the invention comprise a disposable article for detecting or measuring biomarkers of gastrointestinal diseases. The disposable article can comprise a biosensor, and can optionally comprise other components known to the art. In embodiments, the biosensor can comprise at least one bio-recognition element.

In embodiments, the biosensor can detect or measure iAP in a sample. In other embodiments, the biosensor can detect or measure iAP enzymatic activity, total fecal protein, iAP dimerization/dissociation, post-translationally modified iAP, or a combination thereof. Non-limiting examples of post-translational modifications and samples are described herein.

In embodiments, the biosensor can be an immunosensor, and can further comprise a detection signal. Non-limiting examples of detection signals comprise a radioactive signal, colorimetric signal, a fluorescent signal, chemiluminescent signal, or a combination thereof. For example, the biosensor can produce a new color or change in spectral absorption. In embodiments, the biosensor of the present invention comprises a bio-recognition element, or molecular recognition element, that provides the highly specific binding or detection selectivity for a particular analyte, such as iAP. The bio-recognition element, or system, can be a biologically derived material such as an enzyme or sequence of enzymes; an antibody or fragment thereof; a membrane receptor protein; DNA; an organelle, a natural or synthetic cell membrane; an intact or partial viable or nonviable bacterial, plant or animal cell; or a piece of plant or mammalian tissues, and generally functions to interact specifically with a target biological analyte. The bio-recognition element is responsible for the selective recognition of the analyte and the physico-chemical signal that provides the basis for the output signal. The physico-chemical signal generated by the bio-recognition element or elements can be communicated visually to the wearer or caretaker (i.e., via a color change visible to the human eye). Other embodiments can produce optical signals, which can require other instrumentation to enhance the signal. These include fluorescence, bioluminescence, total internal reflectance resonance, surface plasmon resonance, Raman methods and other laser-based methods.

Alternatively, the signal can be processed via an associated transducer which, for example, can produce an electrical signal (e.g., current, potential, inductance, or impedance) that can be displayed (e.g., on a readout such as an LED or LCD display) or which triggers an audible or tactile (e.g., vibration) signal or which can trigger an actuator, as described herein. The signal can be qualitative (e.g., indicating the presence of the target biological analyte) or quantitative (i.e., a measurement of the amount or concentration of the target biological analyte). In such embodiments, the transducer can optionally produce an optical, thermal or acoustic signal.

In any case, the signal can also be durable (i.e., stable and readable over a length of time typically at least of the same magnitude as the usage life of the article) or transient (i.e., registering a real-time measurement). Additionally, the signal can be transmitted to a remote indicator site (e.g., via a wire, or transmitter, such as an infrared or rf transmitter) including other locations within or on the article or remote devices. Further, the biosensor 60, or any of its components, can be adapted to detect and/or signal only concentrations of the target biological analyte above a predefined threshold level (e.g., in cases wherein the target biological analyte is normally present in the bodily waste or when the concentration of the analyte is below a known "danger" level).

In an embodiment, the disposable article can be a diaper to be worn by a subject. Non-limiting examples of additional disposable articles include wipe for cleaning a subject, dipstick, spoon, scoopula, filter paper, or swab.

In aspects of the invention, the disposable article as described herein can be a component of a kit useful for diagnosing a subject with a gastrointestinal disease. Additional components of kits of the invention can comprise a bio-recognition element, a support structure, and instructions for use thereof. For example, an iAP bio-recognition element, such as an antibody as described herein, can be immobilized to a solid support structure.

Non-limiting examples of the composition of the solid support structure comprise plastic, cardboard, glass, plexiglass, tin, paper, or a combination thereof. The solid support can also comprise a dip stick, spoon, scoopula, filter paper or swab.

Aspects of the invention are further directed to a diagnostic kit of molecular biomarkers for identifying a subject exhibiting or having a predisposition to develop a gastrointestinal disease. In embodiments, the kit comprises at least one of a means for determining total fecal protein concentration, a means for determining intestinal alkaline phosphatase (iAP) activity, and an iAP bio-recognition element, wherein together represent a molecular signature that is indicative of the presence of or a predisposition to development of a gastrointestinal disease in a human subject. In embodiments, the signature comprises total protein concentration at least two standard deviations above the mean of a control sample, intestinal alkaline phosphatase protein concentration at least two standard deviations above the mean of a control sample, or intestinal alkaline phosphatase activity at least two standard deviations below the mean of a control sample. In still other embodiments, the signature is selected from at least two of the group comprising total protein concentration at least two standard deviations above the mean of a control sample, intestinal alkaline phosphatase protein concentration at least two standard deviations above the mean of a control sample, and intestinal alkaline phosphatase activity at least two standard deviations below the mean of a control sample. In embodiments, the control sample can comprise two or more control samples.

In one embodiment, the kit includes (a) a container that contains components and support structures as described herein, and optionally (b) informational material. The informational material can be descriptive, instructional, marketing or other material that relates to the methods described herein and/or the use of the agents for diagnostic purposes. In an embodiment, the kit includes also includes a therapeutics, such as antibiotics, probiotics, or an iAP replacement composition.

The informational material of the kits is not limited in its form. In one embodiment, the informational material can include information about production of the components of the kit, such as molecular weight, concentration, date of expiration, batch or production site information, and so forth. In one embodiment, the informational material relates to methods of using the components of the kit, (e.g., to diagnose a subject with a GI disorder). The information can be provided in a variety of formats, include printed text, computer readable material, video recording, or audio recording, or information that provides a link or address to substantive material.

The kit can include other ingredients, such as solvents or buffers, a stabilizer, or a preservative. Optionally, the kit can comprise therapeutic agents, such as iAP replacement compositions or antibiotics, that can be provided in any form, e.g., liquid, dried or lyophilized form, preferably substantially pure and/or sterile. When the agents are provided in a liquid solution, the liquid solution preferably is an aqueous solution. When the agents are provided as a dried form, reconstitution generally is by the addition of a suitable solvent. The solvent, e.g., sterile water or buffer, can optionally be provided in the kit.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only, since alternative methods can be utilized to obtain similar results.

Example 1

Described herein are methods for diagnosis of a common, acquired gastrointestinal emergency in pre-term infants. This disease (necrotizing enterocolitis or NEC) occurs in 12% of pre-term infants; 30% of NEC patients do not survive. In total, ~5000 infants in the United States have NEC per year. The medical condition has delayed and poor diagnosis due to nonspecific symptoms. Biomarkers for reliable diagnosis are required. Using infant stool samples, three biomarker measurements are performed; classifier analysis of the three biomarkers together showed that NEC can be diagnosed with high total protein concentration, low intestinal alkaline (iAP) phosphatase activity, and high levels of intestinal alkaline phosphatase protein. The detection of intestinal alkaline phosphatase protein by western blot alone is strongly correlated with NEC diagnosis and can be used in ELISA format.

Current diagnostic methods in the clinic rely in imaging: x-ray, CT, and ultrasound. Radiography has a diagnostic success rate of only 48% at best. Embodiments as described herein have a 93% true positive rate and 95% true negative rate for disease diagnosis. Embodiments as described herein can have the potential for risk assessment and surveillance of the disease.

The method is relatively fast and inexpensive in comparison to proteomic efforts and mass spectrometry. In addition, other patent applications use serum or urine; serum is invasive and requires extraction of fluids from very fragile patients, whereas urine analysis does not provide a direct readout of the gastrointestinal distress.

Example 2

Abbreviations: AP, alkaline phosphatase; DOL, day of life; iAP, intestinal alkaline phosphatase; MUP, 4-methyl-umbelliferyl phosphate; NBC, Naïve Bayes classifier; NEC, necrotizing enterocolitis; WB, western blot Abstract Objective: Necrotizing enterocolitis (NEC) is the most common gastrointestinal emergency in premature infants and has high mortality and morbidity rates. Diagnosis and management can be difficult because of nonspecific symptomatology, inconsistent radiological findings and rapid deterioration. This investigation was undertaken to test whether fecal intestinal alkaline phosphatase (iAP) is a specific biomarker for NEC.

Study design: In a prospective, longitudinal, case control study, serial stool samples were collected from 6 NEC patients and 12 control infants for the measurement of total fecal protein, iAP activity and iAP protein detection by western blot. Data were evaluated by longitudinal assessment of individual patients, intergroup comparison and sensitivity/specificity evaluation in a classifier-based analysis.

Results: There were no significant differences in gestational age or birthweight between the 2 groups. In 2 patients followed longitudinally, fecal protein increased, iAP activity decreased, and iAP protein was detected on western blot after development of NEC. Mean fecal protein content was higher ($p=0.005$), iAP activity was lower ($p<0.0001$) and specific iAP protein band intensity on western blot was higher ($p=0.002$) in NEC patients at time of diagnosis compared with controls. A 3-feature Naïve Bayes Classifier distinguished NEC from control samples with 93% sensitivity and 95% specificity.

Conclusions: Despite a limited number of subjects and samples, the findings suggest that fecal protein, iAP activity and iAP western blot intensity undergo specific changes during NEC. Preliminary sensitivity and specificity studies suggest potential for the three-component biomarker as a non-invasive diagnostic and monitoring tool for NEC.

Introduction

Necrotizing enterocolitis (NEC) is a serious inflammatory disease of the gastrointestinal tract that affects >5000 very low birth weight (≤1500 g) infants each year.[1,2] It is characterized by high mortality (up to 30%) and long-term morbidity, including short gut syndrome, recurrent infection, nutritional deficiency and neurodevelopmental delay.[3,4] Despite an overall net decrease in mortality for premature infants, there has been an increase in NEC-associated deaths.[5] The disease is often difficult to diagnose and manage, due to initial nonspecific symptomatology and rapid deterioration. Clinicians rely on radiographic evidence, such as pneumatosis intestinalis, to make the diagnosis, but sensitivity of this finding has been reported to be as low as 44%.[6] Although many NEC biomarkers are under investigation,[7] currently none are widely utilized in clinical practice.

Without being bound by theory, intestinal alkaline phosphatase (iAP), measured in stool, offers diagnostic value as a marker for intestinal pathology. This protein is expressed in small intestinal enterocytes, co-secreted into the intestinal lumen and systemic circulation[8] and plays an integral role in maintaining gut barrier function by detoxifying bacterial lipopolysaccharides and maintaining microbial homeostasis.[9,10] As the primary alkaline phosphatase in stool,[3,4] iAP has been identified as one of the 57 proteins in the core human stool proteome.[11] Because of its protective effects, it has been investigated in animal models as a potential treatment for NEC.[12-15] However, most studies have not evaluated iAP as a diagnostic tool and only a few have examined iAP in humans. In this investigation, we examined fecal iAP as a potential biomarker for non-invasive monitoring NEC development in neonates. To our knowledge, this study is the first to investigate fecal iAP levels in human premature infants in order to establish its relationship to NEC.

Methods

Study Design and Participants. This prospective, longitudinal case control study was approved by the institutional review board of the Louisiana State University School of Medicine. It has been carried out according to the Code of Ethics of the World Medical Association (Declaration of Helsinki). After obtaining written parental informed consent, 18 premature infants from 23-37 weeks of gestational age were enrolled at Children's Hospital of New Orleans and Touro Infirmary Hospital. Demographic data of 6 NEC patients and 12 control infants are shown in Table 1. All patient samples were de-identified prior to analysis. Patient records were retrospectively evaluated to determine clinical correlatives. No patients in this study had known chromosomal abnormalities or congenital anomalies that precluded enteral feeding.

Sample Collection/Preparation: Stool samples were collected serially from diapers of study subjects after spontaneous stooling. Stool was stored briefly in hospital specimen refrigerators, until transport to the lab in cooler boxes. In the initial processing step, about 200 mg of stool was measured, and sterile, molecular grade water (Sigma Aldrich) was added to make a desired concentration of 200 mg/ml. The mixture was vigorously vortexed for 30-60 s, or until a well-mixed slurry was evident. The mixture was then centrifuged at 22,000×g for 30 min at 4° C. The supernatant was collected and was stored at −20° C. until assays were performed.

Protein concentration: The concentration of total protein in the stool supernatant was determined by Bradford assay (Coomassie Plus Protein Assay Reagent, Thermo-Scientific), using bovine serum albumin as the standard.

Denaturing gel electrophoresis and western blot: Supernatants of stool samples were mixed with 6× gel loading buffer (375 mM Tris pH 6.8, 50% (w/v) glycerol, 600 mM dithiothreitol, 420 mM sodium dodecyl sulfate) and boiled for 5 mins. A total of 10 µg of total protein was loaded per lane of a denaturing 4-12% Bis-Tris gel (Novex, Life Technologies). The positive control was small intestinal tissue lysate (Abcam). Purified bovine alkaline phosphatase from intestinal mucosa (Sigma Aldrich) was used as a negative control. Duplicate gels were run: one was Coomassie-stained to visualize all proteins in each lane and proteins in the second were transferred onto a PVDF membrane for immunoblotting detection of intestinal alkaline phosphatase. The membrane was serially blocked in 5% (w/v) nonfat dry milk in 50 mM Tris-HCl pH 7.5, 150 mM NaCl, and 0.1% Tween, incubated with primary rabbit polyclonal antibodies against human iAP (Abcan, ab7322 or ab198101), washed, and incubated with horseradish peroxidase-conjugated goat anti-rabbit secondary antibodies (Abcam, ab6721) at room temperature. Chemiluminescent signal was initiated using Pierce ECL western blotting substrate (ThermoScientific) and captured on developed photographic film (AFP Imaging). Western blot densitometry was performed on scanned films (Biorad GelDoc XR) using Image J. In the digitized western blots, the 60 kDa band, which corresponded to iAP, was manually identified. Equivalent areas were quantitated for each lane of each western blot. The negative control was subtracted from each patient sample and the difference was calculated as a percentage of the positive control standard.

Fecal AP catalytic activity: Alkaline phosphatase activity was measured with use of 4-methylumbelliferyl phosphate (MUP) as a fluorescent substrate (Abcam, ab83371) in the presence and absence of L-phenylalanine, an inhibitor of iAP. Relative fluorescence units (RFUs) at 360/440 nm were measured using a Spectra Max M2e spectrophotometer (Molecular Devices, Sunnyvale, CA). Ninety-six-well black optical bottom plates were used. Standards and negative controls were prepared for each plate run. Total AP activity was determined as: AP activity (mU/mL)=(B×dilution factor)/(T×V), in which B is nmol of product; V is volume of sample added to the well; T is reaction time; and U is the amount of enzyme causing hydrolysis of 1 µmol of MUP per minute at pH 10.0 and 25° C. A 100 mM stock of L-phenylalanine (purity >98%; Sigma Aldrich) was freshly prepared in molecular grade water each day of use. A final assay concentration of 10 mM Phe was used to assess inhibition of iAP-specific activity.

Statistical and computational analyses for AP biomarker classification: Differences in means between the NEC and control groups for total fecal protein, iAP activity and intensity of 60 kDa iAP band on western blots were tested using the nonparametric Mann-Whitney U-test; p-values <0.05 were considered significant. Potential biomarker efficacy was assessed via sensitivity (true positive rate) and specificity (true negative rate) calculation. Of the 49 unique fecal samples under analysis, 13 were obtained from NEC patients at the time of clinical diagnosis. Thirty-six samples are labeled as controls, of which 27 were from control subjects and 9 were from NEC patients during healthy intervals. For each variable of interest, specificity and sensitivity was initially obtained using a simple threshold-based classifier. Subsequently, using the scikit-learn package in Python,[16] multi-variable classifier performance was executed by training Naïve Bayes Classifiers (NBC). An NBC assumes each feature is statistically independent; however, it can perform well on multi-feature classification problems, even when the assumption of statistically independent features does not hold.[17] For each classifier, we computed standard error for our sensitivity and specificity estimations by performing five rounds of stratified jackknife resampling, in which 20% of the data was excluded for each round of resampling. We used a 5-fold stratified cross-validation scheme where, for each fold, the NBC was trained on 80% of the data, and the resulting classifier was tested for sensitivity and specificity on the remaining 20% of the data.

Results

Longitudinal Studies: To explore whether the 3 stool parameters correlated with NEC, two preterm infants were observed over time and their stool samples were monitored repeatedly.

Patient 1 (FIG. 1A) was diagnosed with NEC on day of life (DOL) 7. After 14 days of medical treatment, including bowel rest and antibiotics, clinical symptoms and pneumatosis intestinalis resolved. Enteral feeding was restarted with variable success until the baby experienced recurrent NEC and subsequent intestinal perforation on DOL 31. Three fecal analyses were performed: soluble protein concentration, catalytic activity of iAP, and immunoblot detection of iAP. Two stool samples were obtained on DOL 7: before NEC diagnosis (7A, FIG. 1A) and the bloody stool later in the day (7B, FIG. 1A). Data from five other stool samples (DOL 13, 20, 29, 32, and 42) also are presented.

Longitudinal monitoring of patient 1 showed that the 3 candidate biomarkers had diagnostic value (FIG. 1A). The DOL 7A stool sample had a protein concentration of 1.85 mg/mL, catalytic activity of 2218 U/g, and no detectable signal at 60 kDa in the western blot. The DOL 7B stool sample, collected several hours later, had a protein concentration of 2.1 mg/mL, catalytic activity of 250 U/g, and clear immunodetection of iAP. Comparison of the two stool samples from the same patient immediately before and after the onset of NEC indicated that a precipitous drop in iAP activity and an increase of iAP protein are characteristic of NEC.

These biomarkers also exhibited surveillance value. After initial NEC diagnosis on DOL 7, low iAP enzymatic activity and immunodetection of high iAP protein levels persisted in stool samples collected during the period of medical treatment, apparent "recovery", and reinstitution of enteral feeding. The infant subsequently experienced a reoccurrence of NEC with intestinal perforation on day of life 31. In combination, increased fecal protein, low iAP enzymatic activity and high levels of iAP protein in western blots heralded the perforation. After 10 days of treatment that included peritoneal drainage, bowel rest and antimicrobial therapy, the stool collected on DOL 42 had assay values that approximated those prior to the diagnosis of NEC.

Longitudinal monitoring also suggested the prognostic potential of the three candidate biomarkers. Patient 2 (FIG. 1B) was diagnosed with suspected NEC on DOL 19, kept on "NEC watch" (NEC surveillance, bowel rest, antibiotics) for several days before resumption of enteral feedings. Although a definite diagnosis of NEC was not made until DOL 32, stool samples on DOL 13 and 19 had two out of three biomarkers in the positive range for NEC association, potentially forecasting NEC.

Figure 2:
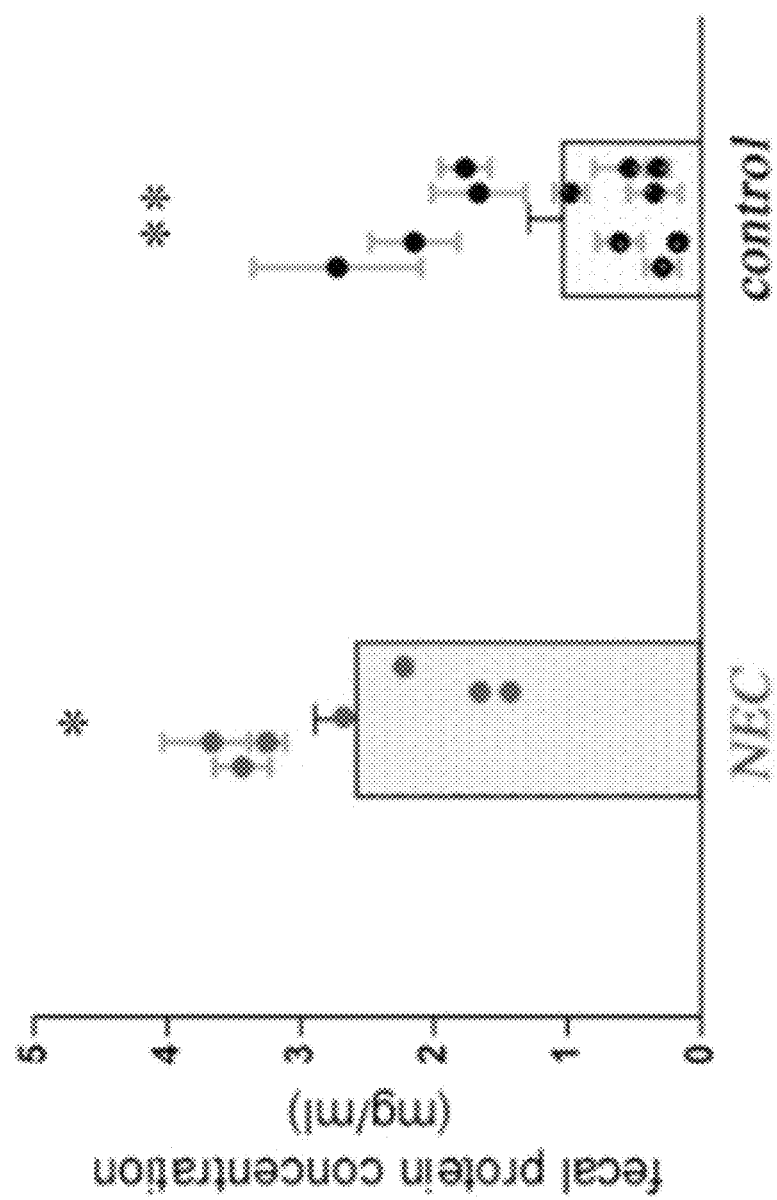
FIG. 2 shows increased concentration of total fecal protein, decreased fecal iAP enzymatic activity, and increased iAP detection on western blot at the time of NEC diagnosis. In the following panels, red circles represent individual stool samples collected during 7 distinct NEC events from 6 patients; black circles represent a composite average f standard error of 2-17 stool samples from 12 control patients. Red and grey columns represent the mean±standard error of all samples collected in NEC events and of all samples from control subjects, respectively. (A) Protein concentrations were higher in stool samples from patients at the time of NEC diagnosis compared with control samples (p-value=0.005). (B) iAP activity was lower in stool samples from patients at time of NEC diagnosis compared with control samples (p-value <0.0001). (C) Amount of iAP protein in stool, quantified by comparison with a positive control standard, was higher in patients at the time of NEC diagnosis compared with control samples (p-value=0.002). Statistical test: Mann-Whitney.

Cross-sectional Studies: In surveys of fecal material collected from 6 NEC and 12 control infants, there were marked differences for the 3 in vitro measurements between stool samples from patients with active NEC and those of controls (FIG. 2). The mean SEM protein concentration of 2.62±0.33 mg/mL in stool samples from patients at the time of NEC diagnosis differed significantly from the level of 0.98±0.25 mg/mL found in fecal samples from control patients matched for post-conceptual age (p=0.005, FIG. 2A). Furthermore, NEC patients had a more than ten-fold lower mean fecal iAP enzymatic activity at the time of diagnosis compared with controls matched for post-conceptual age (162±30 mU/mg vs. 1826±376 mU/mg, NEC vs. control, respectively, p<0.0001, FIG. 2B).

Finally, samples from the 2 patient populations differed significantly (p=0.002) in the relative amount of specific iAP protein, determined by densitometric analysis of immunoblots probed with anti-human iAP antibody and expressed as a percent of a standard positive control. We found nearly a 30-fold higher iAP protein in stool samples from NEC patients compared with samples from healthy premature subjects (215.0±47.6% vs. 7.2±2.3%, NEC vs. control, respectively, FIG. 2C). In summary, stool samples from infants with NEC have increased total protein, decreased iAP enzyme activity, and increased iAP protein at the time of diagnosis compared with healthy controls.

Sensitivity Specificity Studies: In a 3-dimensional scatterplot (FIG. 3A), biomarkers from NEC samples (red circle) cluster independently from controls (black circles), suggesting high sensitivity and specificity can be achieved with these biomarkers. Despite some overlap, the potential for distinguishing between NEC and control patient samples remained clear even when total fecal protein levels were removed as a variable (FIG. 3B). We evaluated sensitivity and specificity directly with both single variable threshold classifiers and a Naïve Bayes Classifier (NBC), which classified the samples based on integration of all 3 tests (FIG. 3C). Clearly, there is a tradeoff between sensitivity and specificity. If maximal sensitivity, or the true positive rate, is the dominant goal, the 3-feature NBC biomarker performs best with 100% sensitivity and 92% specificity. However, if the goal is to simultaneously maximize both sensitivity and specificity, then the 3-feature NBC showed performance of 93% sensitivity and 95% specificity. The iAP activity level considered alone also performs almost as well in this case by achieving both sensitivity and specificity levels of 92%, when using a threshold of 300 mU/mg iAP activity. Perhaps unsurprisingly, though, total fecal protein level alone is not as robust a biomarker for NEC. At 92% sensitivity, specificity falls to 67% using a protein threshold of 1.35 mg/mL. Consequently, fecal iAP activity level and 60 kDa western blot intensity levels hold promise individually as NEC biomarker candidates. However, total fecal protein activity level is only likely to have utility if considered as part of a multi-feature diagnostic evaluation.

Discussion

The diagnosis and management of NEC is complicated by our current inability to accurately identify the disease prior to the development of irreversible intestinal damage. Clinical parameters alone cannot accurately predict disease progression in the majority of patients.[18] Although radiography, the cornerstone of NEC diagnosis and staging,[19] is rapid and accessible in intensive care units, this measure of disease pathology provides qualitative, rather than quantitative, endpoints. There is well-documented variability in interpretation of observable radiological signs determining disease severity.[6, 20, 21] Disturbingly, the hallmark radiological finding, pneumatosis intestinalis, was reported in only 44% of pathology-confirmed NEC.[22]

Quantitative markers, measured as a ratio or on an interval scale, are still needed to achieve a better understanding of NEC, e.g., to distinguish between normal and pathological biological processes or monitor a response to clinical interventions. The clinical definition of NEC could be significantly improved with a shift from sole dependence on clinical impression and imaging findings to an expanded diagnostic palette including reliable molecular biomarkers. Identification of molecular NEC biomarkers amenable to adoption in clinical practice has the potential to reduce neonatal deaths, morbidity, and associated healthcare costs. Moreover, characterization of such parameters can provide insight into cellular integrity, protein expression, and changes in gastrointestinal metabolism. Obtained from serum, urine, feces, and buccal swabs, the discovery of candidate biomarkers for NEC is a focus of current research.[23-25]

Our study demonstrated a correlation between 3 in vitro fecal parameters and patient pathology that is compatible with findings from animal studies. The increased concentration of total fecal protein measured in NEC patients likely is associated with mucosal sloughing and disease-associated inflammatory products, such as serum amyloid A, anaphylatoxin, C-reactive protein, platelet-activating factor, calprotectin, and alpha-1 antitrypsin.[26-31] Of these inflammation-based biomarkers, the latter three have been measured directly in neonatal stool samples.[27, 28, 32-34] However, biomarkers associated with inflammation, while often associated with gastrointestinal pathology, are not specific for NEC diagnosis.

In our study, increased iAP detection via western blot was inversely correlated with lower intestinal AP enzymatic activity in the NEC patients' fecal samples at the time of diagnosis. Our findings are consistent with other reports in the literature. First, biopsied intestinal tissue from patients with inflammatory bowel disease displayed lower AP activity, based on enzyme histochemical analysis.[35] Second, serum iAP was shown to be increased in patients who would go on to develop NEC; however, AP levels were monitored only by gel electrophoresis, and no positive detection of intestinal alkaline phosphatase was detailed.[36] Third, in animal models of induced NEC, the terminal ileum tissue samples in rats showed a decrease in protein content, activity and immunofluorescence specific for alkaline phosphatase.[14, 37] Lastly, decreased mucosal AP activity was also reported in animal models, following ischemia reperfusion.[38] Increased shedding of mucosal protein, including inactivated iAP, could account for our findings.

We had several criteria in evaluating the translational promise of our NEC biomarkers. First, the molecular signatures should be direct readouts of gastrointestinal disease and readily detectable. In this study, we evaluated three candidates: total fecal protein, specific iAP activity, and western blot band intensity for iAP. Monitoring total protein levels in stool has a pathophysiological justification, since high protein levels in stool are closely linked to poor mucosal integrity in the immature neonatal intestine that can be exaggerated by inflammation. The appeal of iAP as a biomarker lies in its tissue-specific expression in the small intestine and its secretion into the mucous layer and gut lumen.[39, 40] It is also responsible for majority of AP enzymatic activity in stool[41, 42] and has been used as a measure of toxic damage to the small intestine in animal models.[43, 44] All three of our stool biomarker candidates showed significant mean differences between NEC patients at the time of diagnosis versus control subjects (FIG. 2).

Second, essential features for a clinically useful molecular biomarker are ease of patient sample handing and a rapid turn-around time of <3 hours. Fresh weight-to-volume standardization in sterile water is rapid, requires minimal reagents, and allows storage in small disposables that facilitate packing and transport. Measurement of protein concentration requires less than 30 minutes. In its current implementation, iAP enzymatic assays and western blots can be completed in one or two hours, respectively.

Our third criterion in the evaluation of our NEC biomarker is the potential to outperform radiographic diagnosis. As a reference, a 7-parameter analysis of clinical diagnostic criteria established by the WHO Integrated Management of Childhood Illness program reported that 85% sensitivity and 75% specificity was high.[45] The detection of pneumatosis intestinalis has a sensitivity of only 44%.[22] In contrast, performance data for our diagnostic approach, including specific iAP activity, immunoblot detection and the three-parameter NBC, were promising, as both sensitivity and specificity were greater than 90%. We also note that, in general, marker performance is more robust for a positive diagnostic readout, such as increased immunoblot detection and protein concentration, than for a negative diagnostic readout: the latter mode is more susceptible to false positive (and false negative) diagnoses. Although future studies that involve a larger patient population can alter our performance data, we conclude that this stool sample analysis has potential clinical utility for improving prognostic diagnosis and subsequent surveillance for NEC.

Challenges to adopting our fecal biomarker analysis as a diagnostic tool for NEC are the heterogeneous composition of some stool samples, the intermittent and variable stooling pattern of some neonates, and the lack of immediate, on-demand test results. However, our 3-feature fecal biomarker analysis has the advantages of requiring less time, no special training or expertise, and is inexpensive in comparison with proteomics or mass spectrometry techniques. Adaptation of the test to continuous, noninvasive surveillance of preterm infants in newborn intensive care units would provide objective measures to assess mucosal integrity, help assess risk associated with feeding regimens, and contribute to our understanding of NEC.

In future studies, our Naïve Bayes Classifier methodology can be extended to simultaneously analyze iAP enzymatic activity, western blot signal and other candidate NEC biomarkers, such as fecal calprotectin and platelet-activating factor.[7] These fecal biomarkers could be added to our classification scheme without the need for additional blood or urine samples from the neonatal patient. The classifier performance of protein biomarkers in urine samples to distinguish between NEC and sepsis patients has been analyzed, and indeed, the efficiency of distinguishing between NEC and sepsis patients was decreased compared with that distinguishing between NEC and normal patients.[46] If our proposed biomarker scheme can maintain high sensitivity and specificity on a larger population of patients with a more complex group of controls, then iAP measurement in conjunction with machine learning analysis of other biomarker candidates could lead to significant advances in NEC diagnosis and management.

REFERENCES CITED IN THIS EXAMPLE

[1] Fitzgibbons S C, Ching Y, Yu D, Carpenter J, Kenny M, Weldon C, Lillehei C, Valim C, Horbar J D, Jaksic T. Mortality of necrotizing enterocolitis expressed by birth weight categories. J Pediatr Surg. 2009; 44:1072-6.

[2] González-Rivera R, Culverhouse R C, Hamvas A, Tarr P I, Warner B B. The age of necrotizing enterocolitis onset: an application of Sartwell's incubation period model. J Perinat. 2011; 31:519-23.

[3] Yee W H, Soraisham A S, Shah V S, Aziz K, Yoon W, Lee S K, Canadian Neonatal Network. Incidence and timing of presentation of necrotizing enterocolitis in preterm infants. Pediatrics. 2012; 129:e298-304.

[4] Young C, Sharma R, Handfield M, Mai V, Neu J. Biomarkers for infants at risk for necrotizing enterocolitis: clues to prevention? Pediatr Res. 2009; 65:91R-7R.

[5] Patel R M, Kandefer S, Walsh M C, Bell E F, Carlo W A, Laptook A R, Sanchez P J, Shankaran S, Van Meurs K P, Ball M B, Hale E C, Newman N S, Das A, Higgins R D, Stoll B J, Eunice Kennedy Shriver National Institute of Child H, Human Development Neonatal Research Network. Causes and timing of death in extremely premature infants from 2000 through 2011. N Engl J Med. 2015; 372:331-40.

[6] Tam A L, Camberos A, Applebaum H. Surgical decision making in necrotizing enterocolitis and focal intestinal perforation: predictive value of radiologic findings. J Pediatr Surg. 2002; 37:1688-91.

[7] Chu A, Hageman J R, Caplan M S. Necrotizing enterocolitis: predictive markers and preventive strategies. NeoReviews. 2013; 14:e113-e20.

[8] Eliakim R, Mahmood A, Alpers D H. Rat intestinal alkaline phosphatase secretion into lumen and serum is coordinately regulated. Biochim Biophys Acta. 1991; 1091:1-8.

[9] Lalles J P. Intestinal alkaline phosphatase: multiple biological roles in maintenance of intestinal homeostasis and modulation by diet. Nutr Rev. 2010; 68:323-32.

[10] Lalles J P. Luminal ATP: the missing link between intestinal alkaline phosphatase, the gut microbiota, and inflammation? Am J Physiol Gastrointest Liver Physiol. 2014; 306:G824-5.

[11] Lichtman J S, Marcobal A, Sonnenburg J L, Elias J E. Host-centric proteomics of stool: a novel strategy focused on intestinal responses to the gut microbiota. Mol Cell Proteomics. 2013; 12:3310-8.

[12] Biesterveld B E, Koehler S M, Heinzerling N P, Rentea R M, Fredrich K, Welak S R, Gourlay D M. Intestinal alkaline phosphatase to treat necrotizing enterocolitis. J Surg Res. 2015; 196:235-40.

[13] Riggle K M, Rentea R M, Welak S R, Pritchard K A, Jr., Oldham K T, Gourlay D M. Intestinal alkaline phosphatase prevents the systemic inflammatory response associated with necrotizing enterocolitis. J Surg Res. 2013; 180:21-6.

[14] Rentea R M, Liedel J L, Welak S R, Cassidy L D, Mayer A N, Pritchard K A, Jr., Oldham K T, Gourlay D M. Intestinal alkaline phosphatase administration in newborns is protective of gut barrier function in a neonatal necrotizing enterocolitis rat model. J Pediatr Surg. 2012; 47:1135-42.

[15] Heinzerling N P, Liedel J L, Welak S R, Fredrich K, Biesterveld B E, Pritchard K A, Jr., Gourlay D M. Intestinal alkaline phosphatase is protective to the preterm rat pup intestine. J Pediatr Surg. 2014; 49:954-60.

[16] Pedregosa F, Varoquaux G, Gramfort A, Michel V, Thirion B, Grisel O, Blondel M, Prettenhofer P, Weiss R, Dubourg V. Scikit-learn: Machine learning in Python. J Machine Learning Research. 2011; 12:2825-30.

[17] Rish I. An empirical study of the naive Bayes classifier. IJCAI 2001 workshop on empirical methods in artificial intelligence: IBM New York; 2001. p. 41-6.

[18] Ji J, Ling X B, Zhao Y, Hu Z, Zheng X, Xu Z, Wen Q, Kastenberg Z J, Li P, Abdullah F, Brandt M L, Ehrenkranz R A, Harris M C, Lee T C, Simpson B J, Bowers C, Moss R L, Sylvester K G. A data-driven algorithm integrating clinical and laboratory features for the diagnosis and prognosis of necrotizing enterocolitis. PLoS One. 2014; 9:e89860.

[19] Bell M J, Temberg J L, Feigin R D, Keating J P, Marshall R, Barton L, Brotherton T. Neonatal necrotizing enterocolitis. Therapeutic decisions based upon clinical staging. Ann Surg. 1978; 187:1-7.

[20] Kosloske A M, Musemeche C A, Ball W S, Jr., Ablin D S, Bhattacharyya N. Necrotizing enterocolitis: value of radiographic findings to predict outcome. AJR Am J Roentgenol. 1988; 151:771-4.

[21] Coursey C A, Hollingsworth C L, Wriston C, Beam C, Rice H, Bisset G, 3rd. Radiographic predictors of disease severity in neonates and infants with necrotizing enterocolitis. AJR Am J Roentgenol. 2009; 193:1408-13.

[22] Ballance W A, Dahms B B, Shenker N, Kliegman R M. Pathology of neonatal necrotizing enterocolitis: a ten-year experience. J Pediatr. 1990; 117:S6-13.

[23] Evennett N, Cerigioni E, Hall N J, Pierro A, Eaton S. Smooth muscle actin as a novel serologic marker of severe intestinal damage in rat intestinal ischemia-reperfusion and human necrotising enterocolitis. J Surg Res. 2014; 191:323-30.

[24] Ng P C, Ma T P, Lam H S. The use of laboratory biomarkers for surveillance, diagnosis and prediction of clinical outcomes in neonatal sepsis and necrotising enterocolitis. Arch Dis Child Fetal Neonatal Ed. 2015; 100:F448-52.

[25] Sylvester K G, Ling X B, Liu G Y, Kastenberg Z J, Ji J, Hu Z, Peng S, Lau K, Abdullah F, Brandt M L, Ehrenkranz R A, Harris M C, Lee T C, Simpson J, Bowers C, Moss R L. A novel urine peptide biomarker-based algorithm for the prognosis of necrotising enterocolitis in human infants. Gut. 2014; 63:1284-92.

[26] Pourcyrous M, Korones S B, Yang W, Boulden T F, Bada H S. C-reactive protein in the diagnosis, management, and prognosis of neonatal necrotizing enterocolitis. Pediatrics. 2005; 116:1064-9.

[27] Amer M D, Hedlund E, Rochester J, Caplan M S. Platelet-activating factor concentration in the stool of human newborns: effects of enteral feeding and neonatal necrotizing enterocolitis. Biol Neonate. 2004; 85:159-66.

[28] Yang Q, Smith P B, Goldberg R N, Cotten C M. Dynamic change of fecal calprotectin in very low birth weight infants during the first month of life. Neonatology. 2008; 94:267-71.

[29] Tayman C, Tonbul A, Kahveci H, Uysal S, Koseoglu B, Tatli M M, Dilmen U. C5a, a complement activation product, is a useful marker in predicting the severity of necrotizing enterocolitis. Tohoku J Exp Med. 2011; 224:143-50.

[30] Cetinkaya M, Ozkan H, Koksal N, Akaci O, Ozgur T. Comparison of the efficacy of serum amyloid A, C-reactive protein, and procalcitonin in the diagnosis and follow-up of necrotizing enterocolitis in premature infants. J Pediatr Surg. 2011; 46:1482-9.

[31] Ng P C, Ang I L, Chiu R W, Li K, Lam H S, Wong R P, Chui K M, Cheung H M, Ng E W, Fok T F, Sung J J, Lo Y M, Poon T C. Host-response biomarkers for diagnosis of late-onset septicemia and necrotizing enterocolitis in preterm infants. J Clin Invest. 2010; 120:2989-3000.

[32] Rabinowitz S S, Dzakpasu P, Piecuch S, Leblanc P, Valencia G, Kornecki E. Platelet-activating factor in infants at risk for necrotizing enterocolitis. J Pediatr. 2001; 138:81-6.

[33] Moussa R, Khashana A, Kamel N, Elsharqawy S E. Fecal calprotectin levels in preterm infants with and without feeding intolerance. J Pediatr (Rio J). 2016.

[34] Shulman R J, Buffone G, Wise L. Enteric protein loss in necrotizing enterocolitis as measured by fecal alpha 1-antitrypsin excretion. J Pediatr. 1985; 107:287-9.

[35] Tuin A, Poelstra K, de Jager-Krikken A, Bok L, Raaben W, Velders M P, Dijkstra G. Role of alkaline phosphatase in colitis in man and rats. Gut. 2009; 58:379-87.

[36] Kampanatkosol R, Thomson T, Habeeb O, Glynn L, Dechristopher P J, Yong S, Jeske W, Maheshwari A, Muraskas J. The relationship between reticulated platelets, intestinal alkaline phosphatase, and necrotizing enterocolitis. J Pediatr Surg. 2014; 49:273-6.

[37] Whitehouse J S, Riggle K M, Purpi D P, Mayer A N, Pritchard K A, Jr., Oldham K T, Gourlay D M. The protective role of intestinal alkaline phosphatase in necrotizing enterocolitis. J Surg Res. 2010; 163:79-85.

[38] Sisley A C, Desai T R, Hynes K L, Gewertz B L, Dudeja P K. Decrease in mucosal alkaline phosphatase: a potential marker of intestinal reperfusion injury. J Lab Clin Med. 1999; 133:335-41.

[39] Goldberg R F, Austen W G, Jr., Zhang X, Munene G, Mostafa G, Biswas S, McCormack M, Eberlin K R, Nguyen J T, Tatlidede H S, Warren H S, Narisawa S, Millan J L, Hodin R A. Intestinal alkaline phosphatase is a gut mucosal defense factor maintained by enteral nutrition. Proc Natl Acad Sci USA. 2008; 105:3551-6.

[40] Shifrin D A, Jr., McConnell R E, Nambiar R, Higginbotham J N, Coffey R J, Tyska M J. Enterocyte microvillus-derived vesicles detoxify bacterial products and regulate epithelial-microbial interactions. Curr Biol. 2012; 22:627-31.

[41] Horrigan F D, Danovitch S H. The origin of human fecal alkaline phosphatase. Am J Dig Dis. 1974; 19:603-8.

[42] Malo M S. A high level of intestinal alkaline phosphatase is protective against type 2 diabetes mellitus irrespective of obesity. EBioMedicine. 2015; 2:2016-23.

[43] Lehmann F G, Hufnagel H, Lorenz-Meyer H. Fecal intestinal alkaline phosphatase: a parameter for toxic damage of the small intestinal mucosa. Digestion. 1981; 21:156-62.

[44] Thomas D W, Henton D H. The use of fecal alkaline phosphatase as an indicator of intestinal damage. Digestion. 1985; 31:82-8.

[45] Group YICSS. Clinical signs that predict severe illness in children under age 2 months: a multi-centre study. The Lancet. 2008; 371:135-42.

[46] Sylvester K G, Ling X B, Liu G Y, Kastenberg Z J, Ji J, Hu Z, Wu S, Peng S, Abdullah F, Brandt M L, Ehrenkranz R A, Harris M C, Lee T C, Simpson B J, Bowers C, Moss R L. Urine protein biomarkers for the diagnosis and prognosis of necrotizing enterocolitis in infants. J Pediatr. 2014; 164:607-12 e1-7.

Example 3

Introduction

Necrotizing enterocolitis (NEC) is an extremely serious inflammatory disease of the gastrointestinal tract that primarily affects premature infants. It occurs in up to 10% of very low birth weight infants (≤1500 g at birth) and is characterized by high mortality (up to 30%) and significant long term morbidity, including infantile short gut syndrome, recurrent infection, parenteral nutrition related cholestasis, nutritional deficiency and neurodevelopmental delay (1).

Despite advances in the field of neonatology, NEC is responsible for increasing deaths in very premature infants (2). The exact cause of the disease is still not well understood, making diagnosis and management a challenge. The course of the disease often involves initial nonspecific symptomatology and rapid clinical deterioration. Although many biomarkers are currently under investigation as potential aides in diagnosing NEC, none are widely utilized to determine the true integrity of the challenged intestine (3).

Intestinal alkaline phosphatase (iAP) has become an enzyme of interest in the study of gastrointestinal disease. Produced and secreted by enterocytes in the proximal small intestine, iAP activity is found throughout the small and large intestine (4). It is the primary alkaline phosphatase (AP) detected in stool (5,6). It has a variety of functions such as cleaving of lipopolysaccharide (LPS) produced by gram-negative bacteria and interfering with activation of Toll-like receptors in the gut (7). It dephosphorylates ATP and has been shown to affect microbial homeostasis through this interaction (8).

With such broad functions involving gut homeostasis, one might expect iAP to be altered in NEC. In rats, Biesterveld et al. demonstrated decreased endogenous iAP catalytic activity during induced NEC and a subsequent increase during recovery from insult (9). Lehmann and Lorenz Meyer observed an increase in fecal iAP after induced toxic damage to the small intestine in rats, followed by a marked reduction in fecal iAP (10). They suggested that fecal iAP could be used as a parameter for toxic damage to the small intestine (10). Thomas and Henton later investigated the use of fecal iAP as a potential marker for intestinal damage but found wide variability (11). They suggested a longitudinal approach to determine clinical usefulness (11). Supplemental iAP has been shown to abate some of the systemic inflammatory responses associated with NEC (9, 12, 14). A recent study proposed serum iAP as a potential biomarker and found a tendency for high iAP levels in infants who later developed NEC (15). These observations suggested the hypothesis that iAP might be a useful biomarker for NEC.

The focus of our study was to establish whether fecal iAP could be used as diagnostic tool for NEC. Fecal iAP measurements are less invasive compared to serum measurements in premature neonates who are already subject to multiple serological examinations. To date, no studies have been published that have investigated fecal iAP in human neonates and its relationship to NEC. We hypothesized that fecal iAP can be used as an objective and specific biomarker for diagnosing NEC and for monitoring the course of NEC once disease is established.

Development of Methodology

In preparation for this study, I sought and obtained Institutional Board Review approval. I designed an informed consent and enrolled a total of 20 infants. I enlisted the help of NICU nurses to help with collection and came up with a system of labeling that would protect patient confidentiality. Stool samples were collected prospectively and charts were reviewed retrospectively to determine clinical correlatives. The literature on fecal iAP measurements is sparse. I found a reference describing how rat fecal matter was mixed with water then centrifuged to obtain a supernatant 16 and so I proceeded with a similar methodology for handling of human stool samples. We determined that 200 mg of measured stool was sufficient to allow for easy supernatant collection and protein quantification. The consistency of stool was highly variable, making wet weight an unreliable parameter. Fecal total protein content (determined by Bradford assay) was used to standardize iAP measurements.

To confirm the presence of IAP in stool we chose western blot (WB) as an initial assay. Surprisingly, positive detection of the protein in stool was extremely difficult in our healthy controls. In fact, there were over 10 samples analyzed that yielded negative results, with no band signal or signal at a much lower than expected position. Initially, we thought our negative results were from failures in handling and/or storage. However, even same-day measurement of freshly acquired stool samples did not yield evidence of protein recognition by anti-iAP antibodies on western blot. It was only upon analyzing a stool sample from our first NEC patient that we found evidence of the full length protein on western blot. When we enrolled a second NEC patient we again had positive results locating the iAP on WB.

Determination of the presence of iAP protein on WB in at least some experiments gave us confidence to move forward with our research. We then performed experiments to determine the ideal handling and storage techniques. We subjected some samples to several days in the refrigerator at 4° Celsius and after 5 days in the refrigerator there was no significant degradation of the protein. Western blots showed continued positive detection of iAP by anti-iAP. Enzymatic activity measurements showed minimal variance from day to day. We also froze our supernatants at −20° Celsius but determined that short periods of storage in the refrigerator at the hospital was acceptable.

We thought that 200 mg of stool would be needed to produce reliable results. In one case, although we collected only 10 mg of stool at the time of NEC diagnosis, we were still able to demonstrate a strong band for fecal iAP on western blot, indicating usefulness of the test even when small amounts of feces are available.

Figure 5:
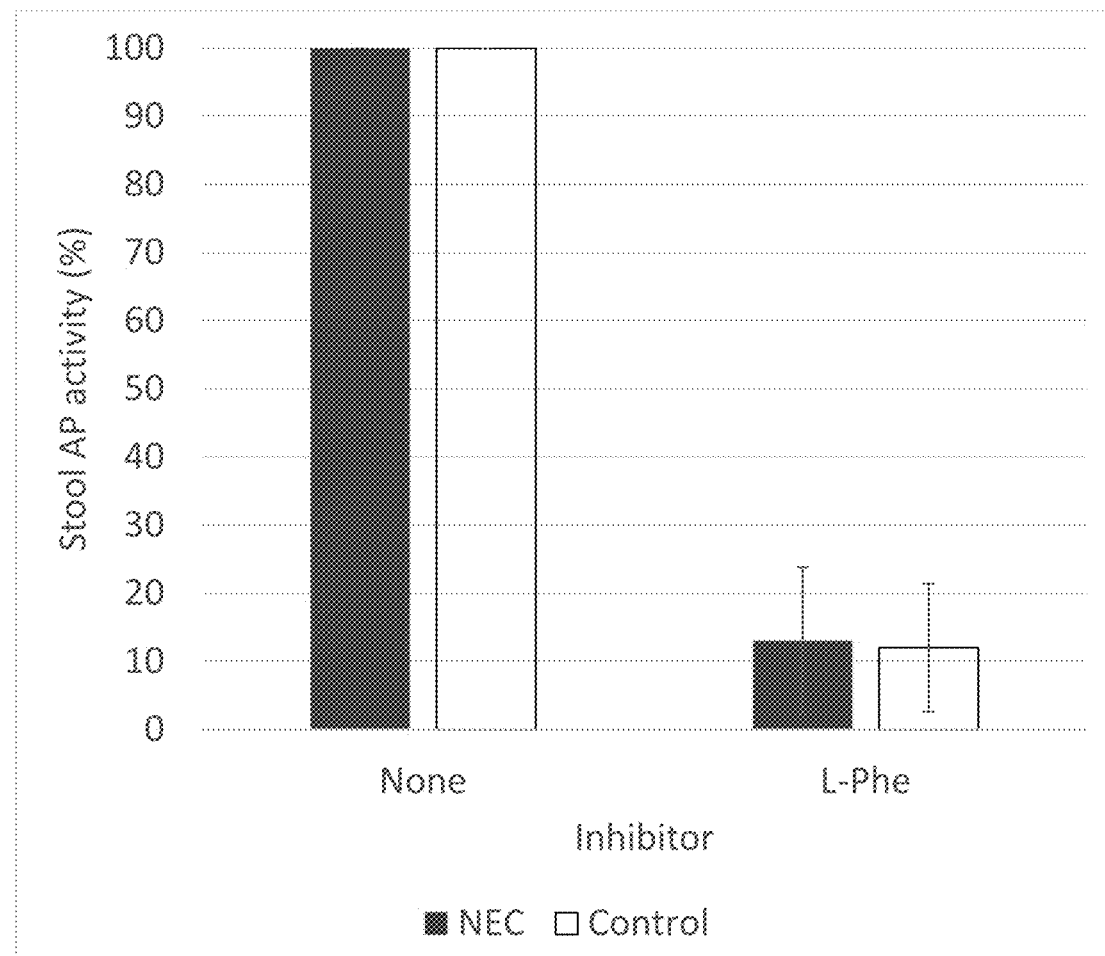
FIG. 5 shows Alkaline phosphatase activity was mostly due to intestinal alkaline phosphatase (iAP). Activity was inhibited by L-Phe which is a specific inhibitor of intestinal alkaline phosphatase activity. There was no observable difference in the degree of inhibition between NEC samples and control samples. NEC samples showed 90% inhibition with standard deviation+/−10. Control samples showed 91% inhibition with standard deviation of +/−9. This represents 12 samples from 6 NEC patients and 64 samples from control patients (n=18).

We chose fluorometric assays to measure activity, because of its sensitivity (detection sensitivity of ~1 µU) over colorimetric methods (17). We were surprised to find there was evidence of alkaline phosphatase activity even in the samples that did not yield a signal on WB. Since our fluorometric activity assays are not specific for intestinal alkaline phosphatase, other alkaline phosphatases in stool can have caused the discrepancy between WB and activity assays. Our next set of investigations were designed to measure the actual activity of iAP present by performing sample assays in the presence and absence of L-phenylalanine (L-Phe), a specific inhibitor of iAP (4, 18). L-Phe blocked 90%±10% (SD) of AP activity in samples from NEC patients and 91%±9% (SD) of AP activity in those from controls, indicating that iAP was the major contributor to alkaline phosphatase activity in the fecal samples studied (FIG. 5). This finding is in agreement with previous reports (3,4) confirming that iAP is the most common AP in stool.

Methods

Study Design and Participants—This was a prospective, case-control study. After obtaining parental informed consent, 20 premature infants from 23-37 weeks gestational age (WGA) were enrolled at Children's Hospital of New Orleans and Touro Infirmary Hospital. Six infants had NEC defined by Bell staging (19). Infants with known chromosomal abnormalities or congenital anomalies that would preclude them from feeding were excluded. Fecal samples from 2 subjects were excluded from statistical analysis due to dissimilar handling. Demographic data of the remaining 18 subjects (6 NEC patients and 12 controls) are shown in Table 1. Handling of Stool—Stool samples were collected serially from diapers of study subjects after spontaneous stooling. Stool was stored briefly at the hospital in specimen refrigerators. The samples were transported in cooler boxes to the lab for initial processing. About 200 mg of stool was measured out, when possible, and molecular grade water was added to make a desired concentration of 200 mg/ml. The mixture was vigorously vortexed for 30 secs to 1 min or until a well-mixed slurry was evident. The mixture was then centrifuged at 22,000×g for 30 min at 4° C. The supernatant was collected and was stored at −20° C. until assays were performed.

Determination of protein concentration—Total protein concentration in stool supernatant was determined by Bradford assay (Coomassie Plus Protein Assay Reagent, Thermo-Scientific), using bovine serum albumin as the standard.

Denaturing gel electrophoresis and western blot—Supernatants of stool samples were mixed with gel loading buffer (375 mM Tris pH 6.8, 50% (w/v) glycerol, 600 mM dithiothreitol, 420 mM sodium dodecyl sulfate) then boiled for 5 mins. A total of 10 micrograms of total protein was loaded per each lane of precast denaturing 4-12% Bis-Tris gel (Novex, Life Technologies). Duplicate gels were run. One gel was stained with Coomassie and the other gel electroblotted onto polyvinylidene difluoride membrane (PVDF) and blocked in 5% nonfat dry milk with Tris buffered Saline and Tween® 20 (50 mM Tris HCl, 150 mM NaCl, Tween® 20). The PVDF was incubated with primary antibodies to full length human iAP ab7322/ab198101 (Abcam) and horseradish peroxidase conjugated Goat antirabbit secondary antibodies ab6721 (Abcam). We used Pierce ECL western blotting substrate (Thermo-scientific) as the peroxidase substrate for chemoluminescence. A developer (AFP Imaging; Mount Kisco, NY) was used to produce films after WB and an imager (Biorad GelDoc XR; Hercules, CA) was used to scan western blots and gels. Densitometry was done to analyze digitized images of western blots. We manually identified bands at 60 kDa on the western blots, which corresponded to intestinal alkaline phosphatase. We then calculated the area relative to background for each 60 kDa band and then expressed this value as a percentage of the positive control. Positive controls were hepatocellular carcinoma whole cell lysate or small intestine tissue lysate (Abcam). Purified bovine alkaline phosphatase from intestinal mucosa (Sigma Aldrich) was used as a negative control.

Fecal iAP Activity—Alkaline phosphatase activity was ascertained with the use of 4-methylumbelliferyl phosphate as a fluorescent substrate ab83371 (Abcam). Substrate background controls and background controls were done to improve accuracy. Relative fluorescence units (RFUs) at 360/440 nm wavelengths were measured using a Spectra Max M2e spectrophotometer (Molecular Devices, Sunnyvale, CA). Ninety-six well black, optical bottom plates were used. Reaction wells for samples, standards and negative background controls were prepared each time the assay was performed and total alkaline phosphatase activity was determined using:

$$\text{ALP activity (mU/ml)} = (B/T)/V \times \text{dilution factor}$$

in which B is nmol of 4-methylumbelliferone (4-MU), V is volume of sample added to the well, and T is reaction time. U is the amount of enzyme causing hydrolysis of 1 μmol of product per minute at pH 10.0 and 25° C. (glycine buffer). A 100 mM stock of L-phenylalanine (purity >98%; Sigma Aldrich) was freshly prepared in molecular grade water each day assays were performed. A final concentration of 10 mM of L-Phe was added to each well to inhibit iAP activity.

Computational and statistical analyses for iAP biomarker classification—We included 18 infants in our analysis of fecal protein and fecal iAP datasets due to uniformity in handling of the stool and similar gestational ages. Differences in means between the NEC and control groups for total fecal protein, iAP activity and intensity of iAP protein band on WB were tested using the nonparametric Mann-Whitney U-test (GraphPad Instat v. 3; La Jolla, CA). Linear regression analysis was used to determine correlations between days until full feeds and total fecal protein and between days until full feeds and iAP activity (GraphPad Prism v7; La Jolla, CA). P-values less than 0.05 were considered significant. Igor Pro (Lake Oswego, OR) was used to generate FIG. 10.

A separate subset of data was used for 51 fecal samples (from 6 NEC patients and 7 controls) for which we had available measurements of specific iAP activity, WB and fecal protein. For western blot band intensity, and total fecal protein levels, we analyzed the distributions of these measurements and investigated the sensitivity and specificity of these measurements when utilized as prognostic and diagnostic biomarkers. Sensitivity is equivalent to the true positive rate for a classifier, while specificity is 1−FPR (the false positive rate) for a classifier. For each of our three variables of interest, we first investigated the specificity and sensitivity obtained using a simple threshold based classifier. For each of these classifiers, we computed standard error for our sensitivity and specificity estimations by performing five rounds of jackknife resampling in which 20% of the data was excluded from the estimation of sensitivity and specificity for each round of resampling. Our data was stratified by class label during this resampling process, so that for each round of resampling 6-7 control samples and 3-4 NEC samples (20% of each class total) were excluded from the analysis.

After investigating single variable classifiers, we explored the utility of multi-variable classifiers by training Naïve Bayes Classifiers (NBC) using the scikit-learn package in Python (20). A Naïve Bayes Classifier assumes that each feature used in classification is statistically independent (21). This naïve assumption is untrue for our three features (iAP activity level, total protein, and WB intensity). However, prior work in the machine learning community has shown that NBCs can perform well on multi-feature classification problems even when the assumption of statistically independent features does not hold (21). To avoid overfitting of the multi-feature classifier, we used a 5-fold stratified cross-validation scheme where, for each fold, the NBC was trained on 80% of the data, and then the resulting classifier was tested on the remaining 20% of the data in order to estimate sensitivity and specificity.

Results

Figure 7:
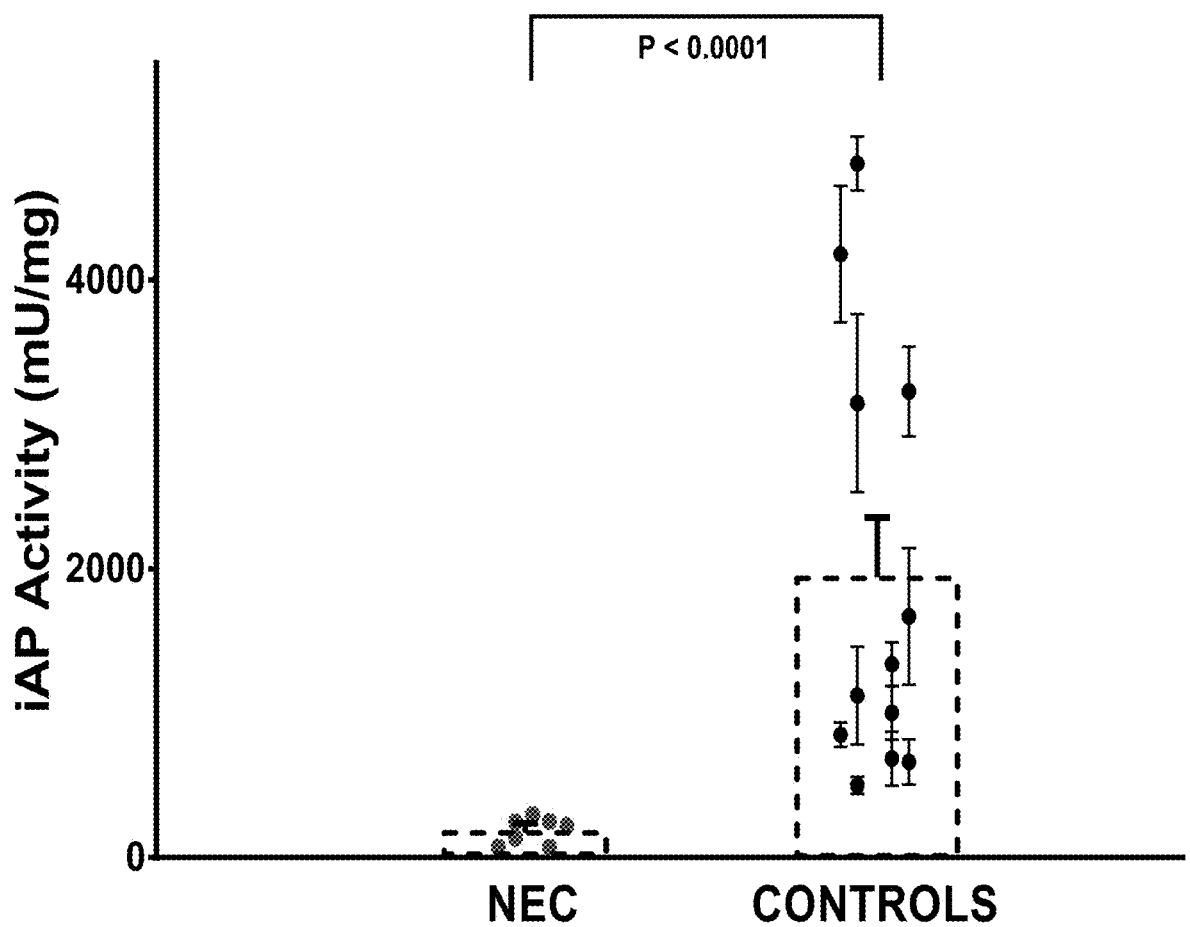
FIG. 7 shows iAP activity was lower in stool samples from patients at time of NEC diagnosis compared to control samples. The red circles represent iAP activity during 7 distinct NEC events of 6 patients (post conceptual age: 29-43 weeks). Each black circle represents a composite average+/−SEM of 2-8 stool samples from each of 12 controls (post-conceptual ages 29-45 weeks). Statistical significance analysis: Mann-Whitney Test, P<0.0001.
Figure 8:
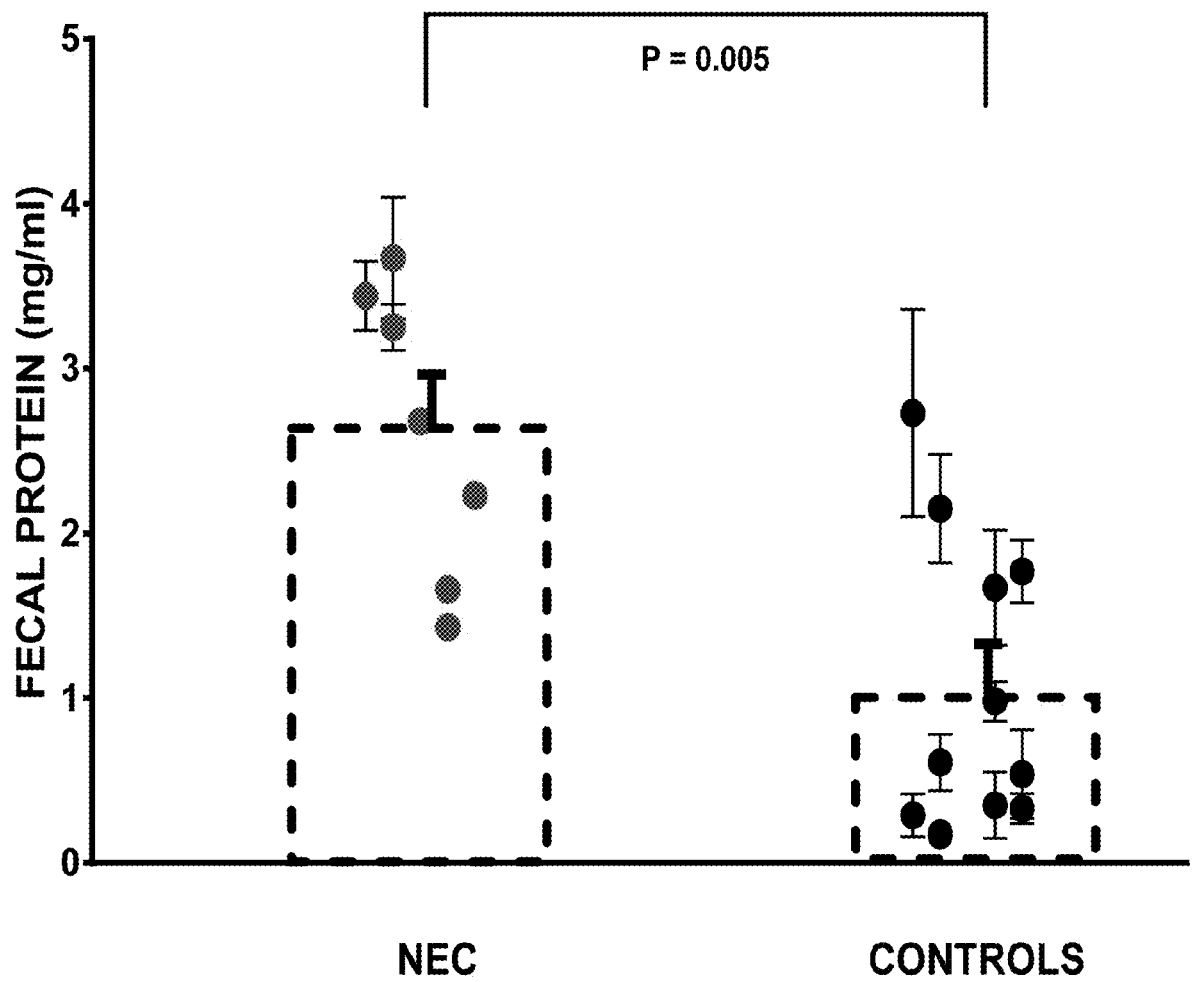
FIG. 8 shows total fecal protein was higher in stool samples from patients at the time of NEC diagnosis compared to control samples. The red circles represent total fecal protein levels during 7 distinct NEC events of 6 patients (post conceptual age: 29-43 weeks). Each black circle represents a composite average=/−SEM of 2-16 stool samples from 12 controls (post conceptual ages: 29-45 weeks). Statistical analysis: Mann-Whitney Test, P=0.005
Figure 9:
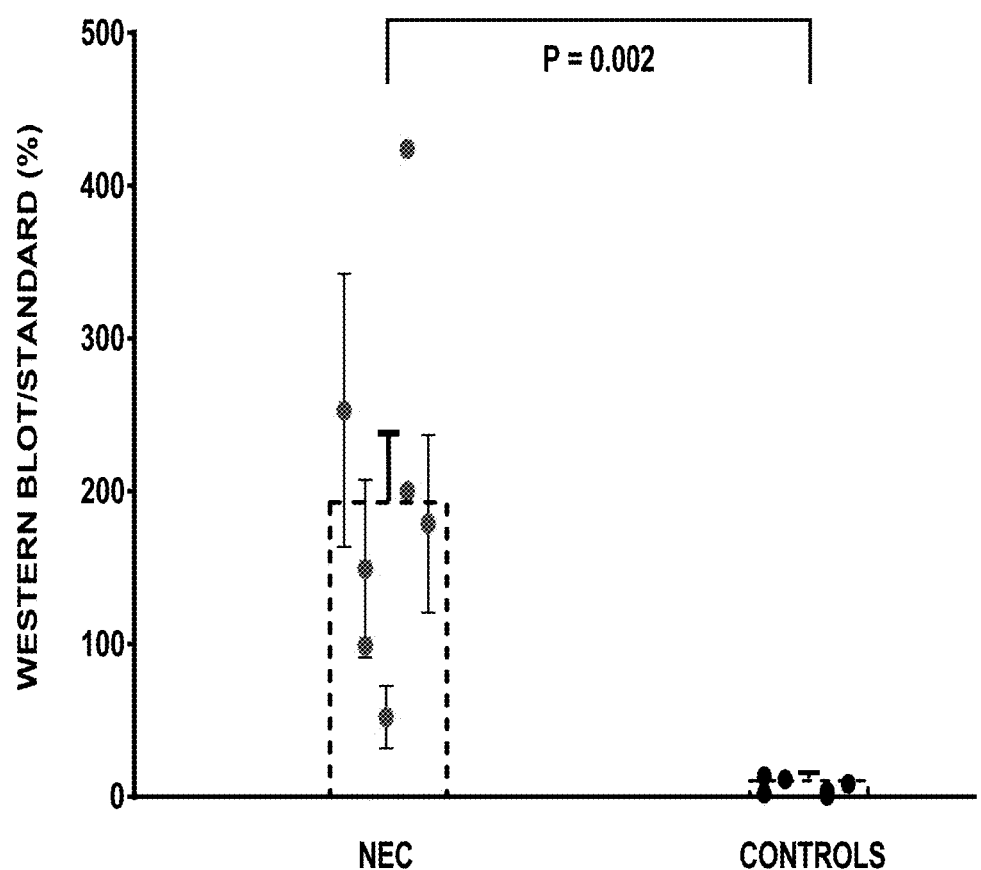
FIG. 9 shows the intensity of iAP protein signal quantified as a percentage of positive control signal was much higher in stool samples from patients at the time of NEC diagnosis compared to control samples. The red circles represent the intensity of iAP protein signal during 7 distinct NEC events of 6 patients (post conceptual age: 29-43) Each black circle represents at least 1 stool sample from 7 controls (post conceptual age 29-35 weeks). Statistical analysis: Mann-Whitney Test, P=0.002

Compared with multiple samples from the controls roughly matched for the gestational and chronological age, stools from NEC patients at the time of diagnosis had decreased iAP activity (FIG. 7), increased total fecal protein (FIG. 8) and increased detection of iAP protein (FIG. 9). Fecal iAP activity was low at the time of diagnosis of NEC compared to averaged controls. When the Mann-Whitney test was applied there was statistical significance between the groups. The mean values for fecal iAP activity was 184 mU/mg with a standard error of measurement (SEM) of 34 vs 1932 mU/mg in the control group with SEM of 433 ($P<0.0001$). This is illustrated in FIG. 2.

Figure 3:
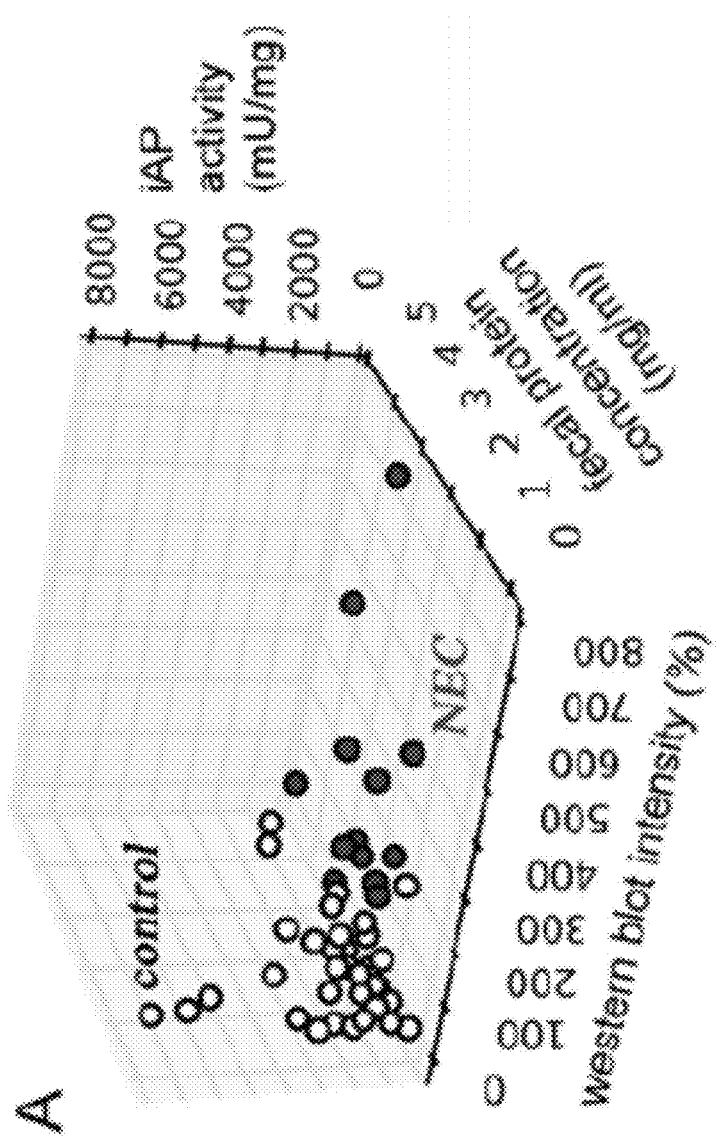
FIG. 3 shows fecal iAP-related measurements have high specificity and sensitivity. (A) 3-dimensional scatterplot of measurements for our biomarker candidates, where red diamonds represent NEC samples and black circles represent controls. (B) A 2-dimensional projection of the 3-dimensional scatterplot that relates exclusively to iAP activity and western blot intensity measurements. (C) Sensitivity and specificity curves for each biomarker candidate individually, as well as for a combined Naïve Bayes Classifier that considers all 3 features simultaneously. Analysis covers 49 samples with 13 NEC samples, 9 NEC patient-derived control samples, and 27 control patient-derived control samples. The Spearman correlation coefficient was 0.19 for comparison of western blot intensity and total protein content, −0.48 for total protein content and iAP activity, and −0.58 for iAP activity and western blot intensity.
Figure 3:
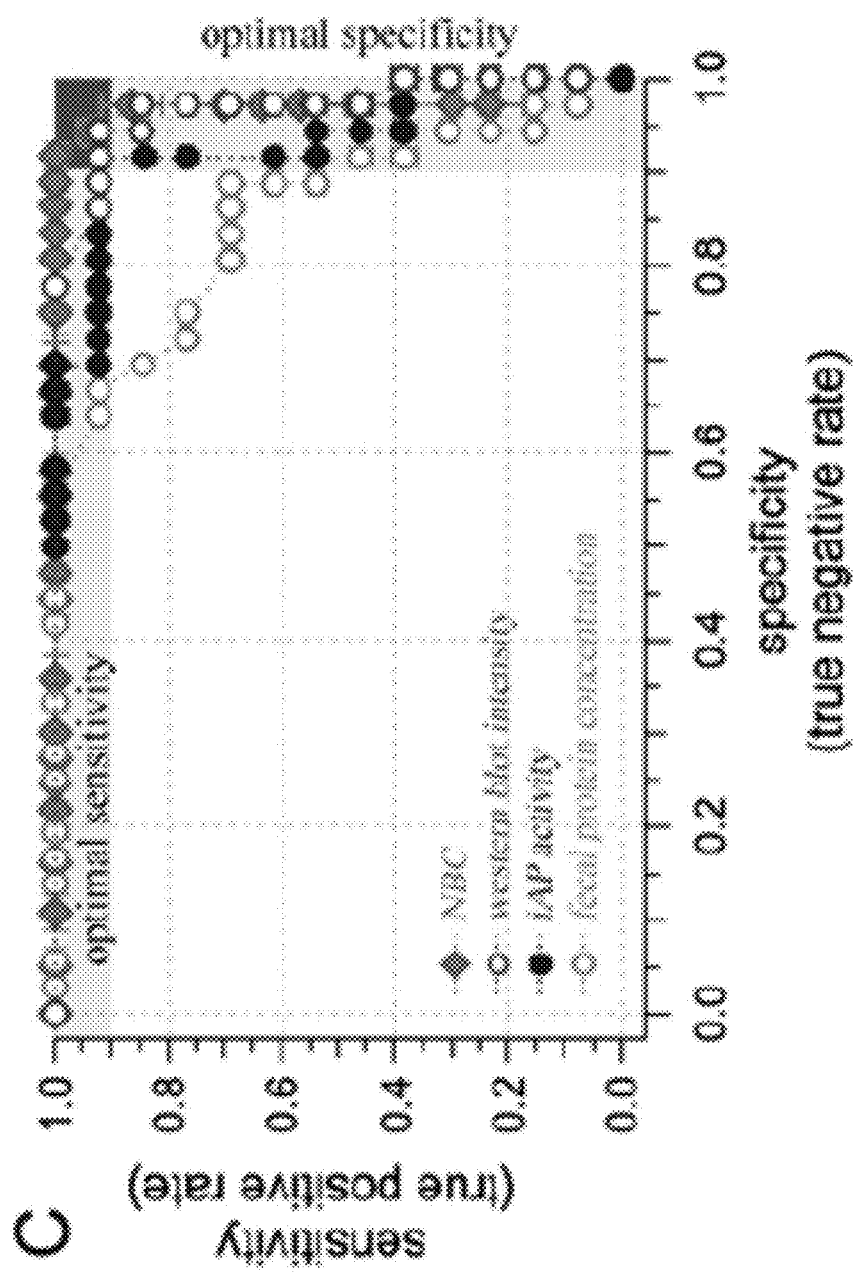

We found that NEC patients had significantly higher amounts of fecal protein at the time of diagnosis compared to matched controls for post conceptual age. We averaged protein amount from individual non-NEC patients between 29-43 PCA and compared this to the patient stool samples at the time of diagnosis of NEC totaling 7 events from 6 patients (FIG. 3). Nonparametric tests (Mann-Whitney) were used to compare the non-normally distributed data and there was a statistically significant difference (P=0.005) between the groups. Mean at time of diagnosis was 2.62 with SEM of 0.33 in NEC patient samples compared to a mean of 0.98 with SEM of 0.25 in averaged controls.

WB quantification by percentage of positive control was performed using 7 NEC events in 6 patients and 7 control patients. Mean WB percent in the NEC patient samples was 193% vs 6% in controls (P=0.0022). The standard error of measurement was 45 in NEC vs 1.9 in controls. (FIG. 4).

Figure 10:
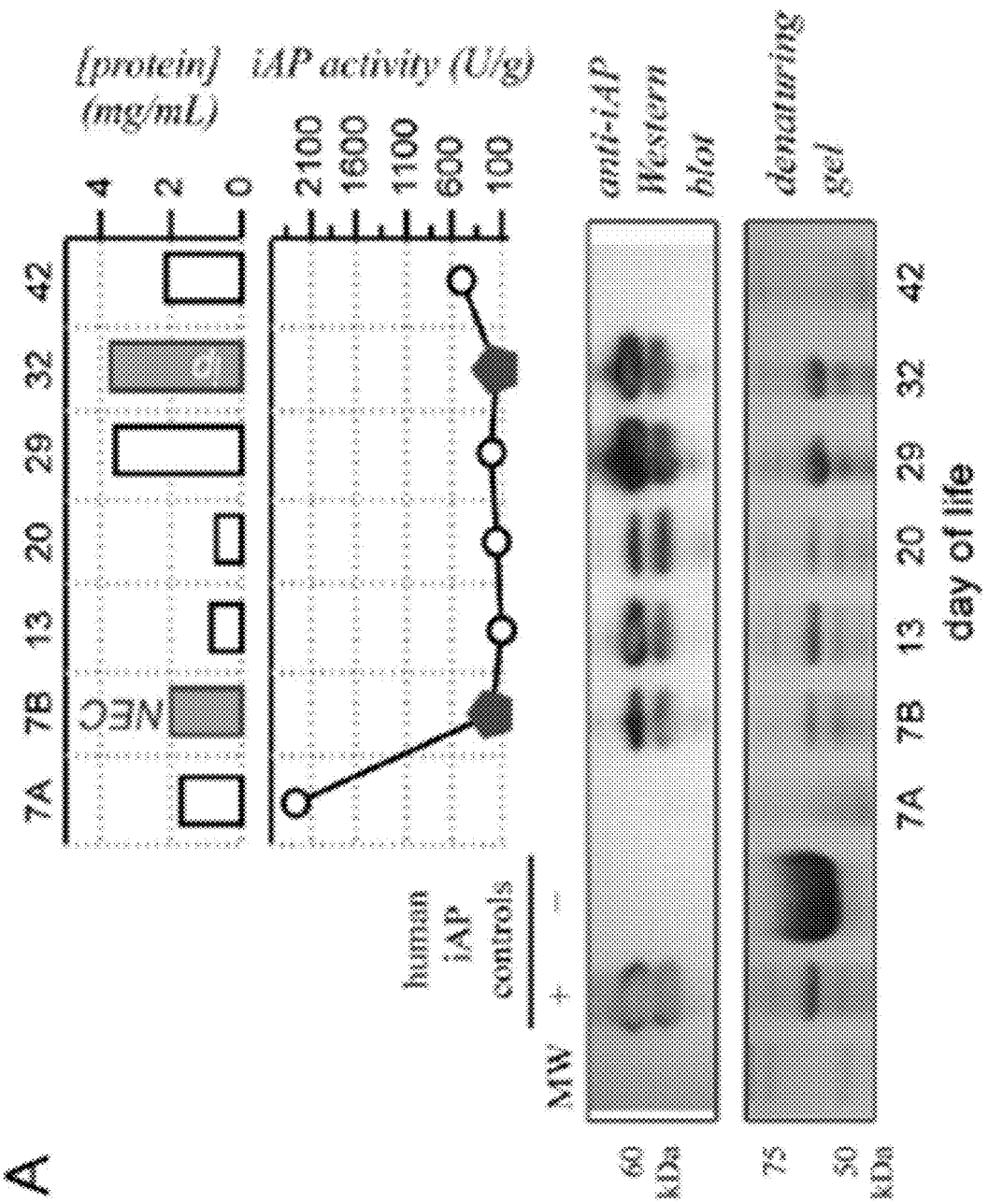
FIG. 10 shows there are decreased fecal iAP enzymatic activity, increased total fecal protein and increased iAP detection on WB at the time of NEC diagnosis. (A) Illustrates longitudinal measurements of iAP activity, total fecal protein and iAP enzymatic activity in a NEC patient who subsequently developed perforation. The red points and columns represent NEC episodes. There is a precipitous decrease in fecal iAP activity corresponding to time of diagnosis demonstrating fecal iAP activity as a diagnostic tool for NEC. There is emergence of intense iAP protein detection on western blot. The patient completes 14 days of treatment, but had an intestinal perforation (ip) on day of life 31. After 10 additional days of bowel rest there was no longer strong detection of iAP by the anti-iAP antibody and a trend towards higher iAP activity. (B) There is a similarly observed decreased fecal iAP activity and increased iAP amounts at the time of NEC diagnosis in a second patient. The green point represents an episode of bloody stool and corresponds to suspected NEC with bowel distension (bd). There was emergence of iAP detection during NEC surveillance that was no longer evident until NEC diagnosis on day of life 32. Again noted was a drop in activity surrounding the diagnosis of NEC (red dot and column) and trend towards higher activity and decreased iAP detection on WB after recovery. (C) NEC was associated with low fecal iAP activity, high fecal protein and high fecal iAP amounts (on WB). Three samples from 3 NEC patients (labeled N, red columns) at the time of NEC diagnosis were are matched with 3 samples from 3 control subjects (labeled C, white columns) with similar gestational and chronological age. The difference in group 3 is less striking and can have represented subclinical disease in a premature infant with feeding intolerance (D) This figure represents sequential stool sampling pre-diagnosis (labeled pre, white column) and at the time of diagnosis (labeled d, red column) in 4 NEC patients with corresponding iAP enzymatic activity, total fecal protein and iAP detection on western blot.

The antibody we chose for western blot analysis did not easily detect iAP in stool except in the cases of NEC. Longitudinal observations of 2 patients with NEC are shown in FIGS. 10A and 10B. Panel A highlights a premature infant with prolonged course of NEC followed by perforation. It shows a precipitous drop in iAP activity and appearance of iAP protein on WB at the time of initial NEC diagnosis, a persistently low iAP activity and evidence of iAP protein on WB during initial therapy until subsequent perforation. After Penrose drain placement and ten days of bowel rest, there was no longer evidence of high iAP protein on the WB, but there was an increase in fecal iAP activity. Panel B highlights a different infant with multiple NEC surveillance events (one event is represented by the green point) prior to NEC. The suspected NEC episode was associated with evidence of iAP protein on WB, but normal iAP activity. This resolved before the precipitous drop in the iAP activity and emergence of high iAP protein on WB at the time of NEC. After medical management and recovery from NEC, iAP activity increased and there was no longer iAP protein demonstrable on WB. FIG. 10 Panel C shows 3 groups of samples, each consisting of stool from a NEC patient at the time of diagnosis compared with that from a closely matched control. Groups 1 and 2 clearly show increased total fecal protein, decreased iAP activity, and evidence of iAP protein on WB. In group 3, there was no significant difference in iAP activity and total fecal protein, but the western blot clearly differentiates between the NEC and control samples. FIG. 5 Panel D shows stools taken prior to and at the time of diagnosis from 4 different NEC patients. Using each patient as his or her own control, the diagnosis of NEC was associated with decreased iAP activity, increased total fecal protein and the demonstration of iAP protein on WB.

Figure 11:
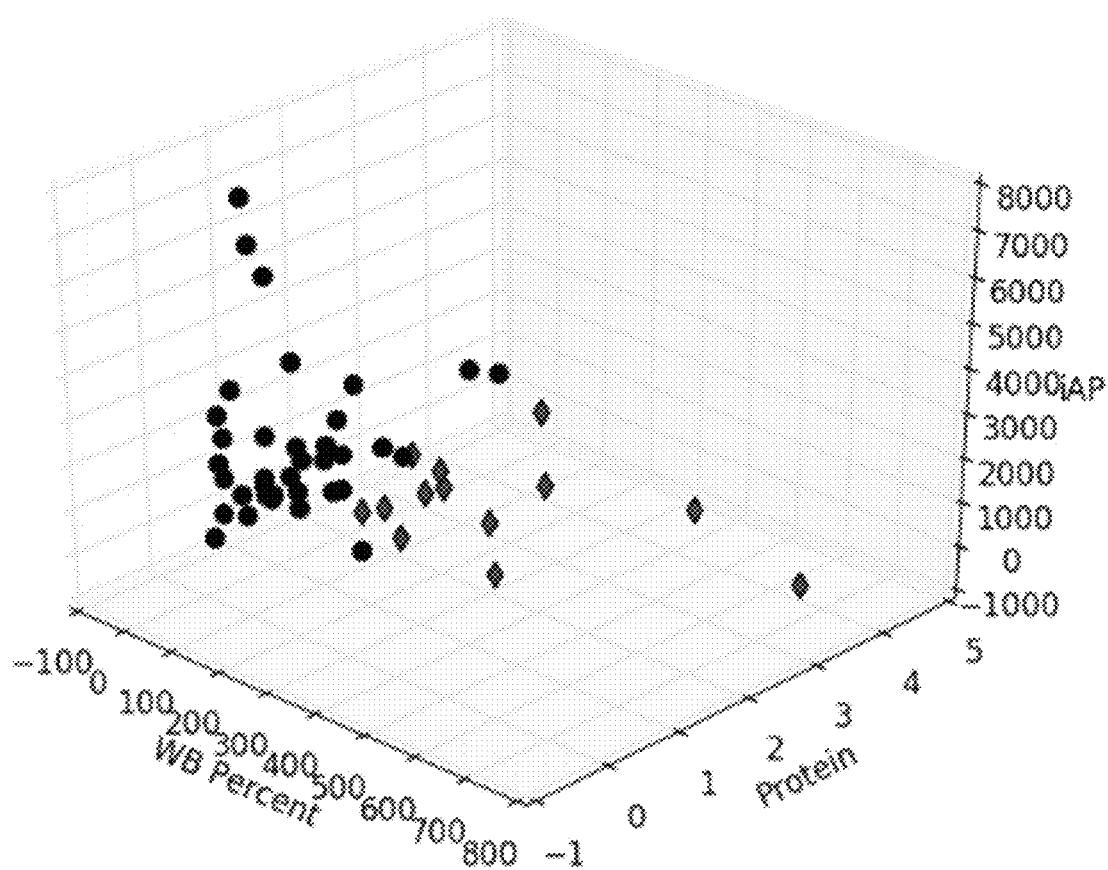
FIG. 11 shows that combining all 3 biomarkers has possible clinical utility and improvement in sensitivity and specificity. Figure Represents data points from 6 NEC patients and 7 controls with a total of 51 samples included. (A) illustrates a 3D scatterplot graph comparing WB data, fecal iAP activity and fecal protein The red diamonds represent averaged total fecal protein, iAP activity and WB percentage of fecal samples from NEC patients at the time of diagnosis. The black circles represent averaged total fecal protein, iAP activity and WB percentage of control points (inclusive of NEC patients in disease-free period) (B) Represents a 2D scatterplot graph that shows the relationship between fecal iAP activity and WB percentage. There is clustering of control samples (black circles) in lower WB percentage and tendency towards high activity. The opposite is demonstrated with NEC samples whereby there is higher WB percentage and low activity. (C) Schematic illustrating Naïve Bayes Classifier used to demonstrate sensitivity and specificity of all three biomarkers individually and in combination to improve performance.

FIG. 11 Panel A is a 3D scatterplot illustrating NEC samples and controls with fecal iAP activity, fecal protein and WB data points. NEC samples are labeled in red. Panel B depicts a 2D scatterplot showing iAP activity and WB percentage. There is high activity and low WB percentage in controls. Combining all 3 biochemical assays increased sensitivity and specificity observed despite low sample amounts and patient numbers. FIG. 6 panel C demonstrates the utility of examining multiple features simultaneously by depicting the tradeoff between sensitivity and specificity for multiple threshold values and multiple feature selections. Western blot intensity considered alone performs best with 100% sensitivity at 70% specificity for a detection threshold of 10% positive control band intensity. However, if 100% sensitivity is not required and the goal is to simultaneously maximize both sensitivity and specificity, then the 3 feature Naïve Bayes Classifier performs best by reaching a sensitivity of 95% and a specificity of 93%. The iAP activity level considered alone performs almost as well in this case by achieving a sensitivity level of 95% and a specificity of 91% when using a threshold of 300 mU/mg iAP activity. When western blot intensity level is considered alone at 95% sensitivity, the specificity level is 88% using a 30% positive control band intensity threshold. However, perhaps unsurprisingly, total fecal protein level alone is not specific for NEC. In order for total fecal protein level to achieve 95% sensitivity, the specificity must drop to 44% using an interpolated threshold of 1.02 mg/mL. Consequently, fecal iAP activity level and 60 kDa western blot intensity levels hold promise individually as NEC biomarker candidates.

Figure 12:
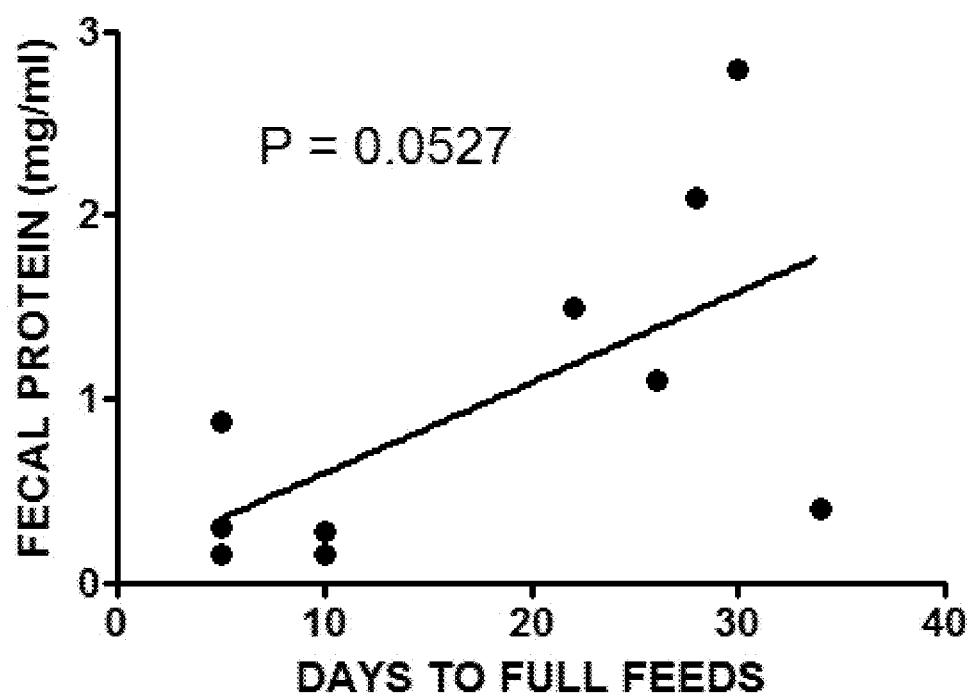
FIG. 12 shows there was an identifiable trend towards lower fecal protein (Panel A) and higher fecal iAP enzymatic activity (Panel B) in those infants who tolerated feeds well and advanced rapidly to full feeds without issue. Graph represents average total fecal protein and fecal iAP activity in stool from 10 control patients during the first month of life related to the duration of time until achievement of full enteral feeds.

There was a noted trend towards higher fecal protein in controls with feeding intolerance, as defined by the number of days needed to reach target enteral feeding volume (FIG. 12). The opposite trend is seen in iAP activity although the association is much less striking.

Heterogeneity of stool could interfere with the reliability of the test. In one particular inhomogeneous stool, the mucous-containing portion (FIG. 13A) resembled other NEC samples, whereas the more solid portion of the stool (FIG. 13B) was similar to control in terms of iAP protein on WB and iAP activity.

Discussion

In our study, we observed alterations in total fecal protein, iAP protein by WB and iAP activity in stools from NEC patients at the time of diagnosis. The high protein levels in stool of NEC patients at the time of diagnosis can reflect loss of mucosal integrity in an already immature intestine as well as inflammatory products associated with the disease. Shulman et al. demonstrated a similar trend with significantly increased alpha 1 antitrypsin in stool at the time of NEC diagnosis compared to controls (22).

Intestinal alkaline phosphatase is expressed primarily in the apical enterocytes of the small intestine, making it an ideal, relatively specific candidate biomarker for localizing gastrointestinal disorders such as NEC. It adheres closely to the membrane but is also shed into the lumen (4). iAP was recently demonstrated by Shifrin et al. to be distributed into the mucus layer and gut lumen via microvillar vesicle shedding (23). During inflammatory insult and bowel necrosis, disruption of the mucosal barrier and cell death, as well as shedding of the mucosal lining, would lead to an increased release of mucosal proteins such as iAP into the feces. The rarity of iAP signal on western blot, but high iAP activity in the stools of control subjects is still not well understood. Perhaps the normal shedding process changes free luminal iAP structure in a way that does not allow for recognition by our particular antibody. The immunogen for the antibody is full length native human iAP from small intestinal tissue and it can be more sensitive to the membrane bound full length protein. Alternatively, there are 2 known isoenzymes of iAP, the fetal and adult forms that undergo developmental changes (24,25). It can be that NEC inflammation is associated with production of an isoenzyme recognized by our antibody, whereas iAP produced under normal conditions is another isoenzyme that is not recognized. In any case, the difference in WB findings is highly suggestive of a conformational difference in fecal IAP between the healthy and diseased state.

The sudden decrease in overall fecal iAP activity that we found in fecal samples from NEC patients at the time of NEC diagnosis was similarly found in rat pups with induced NEC (13,26). Whitehouse et al. demonstrated via intestinal histology and tissue sampling of terminal ileum a decrease in tissue iAP protein and activity (26). The cellular loss, and presumed shedding into the intestinal lumen, that is used to explain decreased iAP protein and activity, at the tissue level, can also help explain increased iAP protein and decreased activity in the stool of patients with NEC. It is interesting to note that adult patients with inflammatory bowel disease were found to exhibit lower AP activity in biopsied intestinal tissue (27).

The mechanism for low iAP activity at the time of NEC does not appear to be due to an initial deficiency since we observed a rapid decline in activity from normal levels in some NEC patients. The loss of iAP enzymatic activity can reflect damage to the enzyme's catalytic site. In an animal model, Sisley et al. demonstrated decreased mucosal AP activity following ischemia reperfusion and suggested that the metal binding sites can be more susceptible to oxidative damage (28).

The drop in fecal iAP activity with a corresponding sudden appearance of fecal iAP protein on WB sometimes happens just hours prior to diagnosis. This observation indicates that the use of activity assays and western blot for iAP detection can offer diagnostic value with an initial event. An additional biomarker of this sort can offer little benefit in cases where NEC can be identified readily by traditional means (bloody stools, pneumatosis intestinalis etc.). However, use of fecal iAP would be most beneficial in establishing the diagnosis in those with subclinical disease or in those who lack clear radiographic evidence. Although thought to be pathognomonic for NEC, Ballance et al. showed that pneumatosis intestinalis was actually present in only 48% of pathologically confirmed in the NEC patient population (29). Fecal iAP could be also used during recovery from NEC to gauge the integrity of the bowel and guide feeding strategies in our most vulnerable patient population and to determine the length of time needed for recovery. Without being bound by theory, the needs of some children can vary from 7-14 days of treatment that is considered standard management.

These biomarkers can even be useful in patients without NEC. We observed a tendency for control infants with feeding intolerance and delayed achievement of full enteral feeding to have higher total fecal protein and lower iAP activity. Control infants who tolerated feeds well exhibited low total fecal protein and very high iAP activity. We have no information yet concerning the presence or absence of iAP protein by WB as it relates to feeding intolerance. If this is confirmed by larger studies, it would provide more incentive to explore the potential benefit of iAP supplementation in these cases. More studies are needed to establish normal values for each parameter at all gestational and chronological ages, and to determine dietary and other factors that can influence them.

No method is without limitations. A potential confounding factor of fecal iAP testing is the heterogeneous nature of stool. We had one stool sample collected at the time of NEC diagnosis that had two distinct consistencies namely mucous and normal appearing stool. We separated the parts and the normal appearing stool had results similar to controls, whereas the mucous-containing portion had the expected low iAP activity and high iAP signal on western blot (FIG. 13). We did not include these data points in our analysis due the wide discrepancy of stool preparation. This was the only sample with this problem and the frequency of this occurrence is unknown. Another challenge we faced was the infrequent and sporadic stooling patterns associated with prematurity that did not allow for exact standardized collection times among subjects. In the clinical realm, depending solely on stool samples might lead to delayed diagnosis due to poor stooling. No biomarker will substitute for a good physical exam and clinical expertise. Probably the best use of fecal iAP as a biomarker would be as an adjunct in establishing the diagnosis of NEC, monitoring disease progression and in surveillance or monitoring of high risk groups.

In our examination of 3 potential NEC biomarkers related to intestinal alkaline phosphatase, we have demonstrated that stool sample analysis has potential clinical utility for improving diagnosis of necrotizing enterocolitis. We have shown that specific iAP activity levels and western blot band intensity can both be used to identify NEC patient fecal samples with high sensitivity and specificity when considered independently. We have also shown that multiple features can be combined using a Naïve Bayes Classifier in order to simultaneously achieve better levels of sensitivity and specificity. Moreover, in future work, our Naïve Bayes Classifier methodology can be extended to simultaneously analyze iAP activity, western blot band intensity, and multiple other candidate NEC biomarkers which were beyond the scope of this current study.

Conclusion

Fecal iAP protein on WB, and total fecal protein are increased, but fecal iAP activity is decreased in patients with NEC at the time of diagnosis. Measurements of iAP protein by WB, iAP activity and fecal protein amounts are useful biomarkers individually, but sensitivity and specificity of diagnosis can be improved by combining the 3 parameters. More studies are needed to determine sensitivity and specificity of each assay individually and in combination.

REFERENCES CITED IN THIS EXAMPLE

1 Neu, J. & Walker, W. A. Necrotizing enterocolitis. N Engl J Med 364, 255-264, doi:10.1056/NEJMra1005408 (2011).
2 Patel, R. M. et al. Causes and timing of death in extremely premature infants from 2000 through 2011. N Engl J Med 372, 331-340, doi:10.1056/NEJMoa1403489 (2015).
3 Ng, P. C., Chan, K. Y. & Poon, T. C. Biomarkers for prediction and diagnosis of necrotizing enterocolitis. Clin Perinatol 40, 149-159, doi:10.1016/j.clp.2012.12.005 (2013).
4 Goldberg, R. F. et al. Intestinal alkaline phosphatase is a gut mucosal defense factor maintained by enteral nutrition. Proc Natl Acad Sci USA 105, 3551-3556, doi: 10.1073/pnas.0712140105 (2008).
5 Horrigan, F. D. & Danovitch, S. H. The origin of human fecal alkaline phosphatase. Am J Dig Dis 19, 603-608 (1974).
6 Malo, M. S. A High Level of Intestinal Alkaline Phosphatase Is Protective Against Type 2 Diabetes Mellitus Irrespective of Obesity. EBioMedicine 2, 2016-2023, doi:10.1016/j.ebiom.2015.11.027 (2015).
7 Fawley, J. & Gourlay, D. M. Intestinal alkaline phosphatase: a summary of its role in clinical disease. J Surg Res 202, 225-234, doi:10.1016/j.jss.2015.12.008 (2016).
8 Malo, M. S. et al. Intestinal alkaline phosphatase promotes gut bacterial growth by reducing the concentration of luminal nucleotide triphosphates. Am J Physiol Gastrointest Liver Physiol 306, G826-838, doi:10.1152/ajpgi.00357.2013 (2014).
9 Biesterveld, B. E. et al. Intestinal alkaline phosphatase to treat necrotizing enterocolitis. J Surg Res 196, 235-240, doi:10.1016/j.jss.2015.02.030 (2015).

10 Lehmann, F. G., Hufnagel, H. & Lorenz-Meyer, H. Fecal intestinal alkaline phosphatase: a parameter for toxic damage of the small intestinal mucosa. Digestion 21, 156-162 (1981).

11 Thomas, D. W. & Henton, D. H. The use of fecal alkaline phosphatase as an indicator of intestinal damage. Digestion 31, 82-88 (1985).

12 Riggle, K. M. et al. Intestinal alkaline phosphatase prevents the systemic inflammatory response associated with necrotizing enterocolitis. J Surg Res 180, 21-26, doi:10.1016/j.jss.2012.10.042 (2013).

13 Rentea, R. M. et al. Intestinal alkaline phosphatase administration in newborns is protective of gut barrier function in a neonatal necrotizing enterocolitis rat model. J Pediatr Surg 47, 1135-1142, doi:10.1016/j.jpedsurg.2012.03.018 (2012).

14 Heinzerling, N. P. et al. Intestinal alkaline phosphatase is protective to the preterm rat pup intestine. J Pediatr Surg 49, 954-960; discussion 960, doi:10.1016/j.jpedsurg.2014.01.031 (2014).

15 Kampanatkosol, R. et al. The relationship between reticulated platelets, intestinal alkaline phosphatase, and necrotizing enterocolitis. J Pediatr Surg 49, 273-276, doi: 10.1016/j.jpedsurg.2013.11.037 (2014).

16 Malo, M. S. et al. Intestinal alkaline phosphatase preserves the normal homeostasis of gut microbiota. Gut 59, 1476-1484, doi:10.1136/gut.2010.211706 (2010).

17 Porstmann, B., Porstmann, T., Nugel, E. & Evers, U. Which of the commonly used marker enzymes gives the best results in colorimetric and fluorimetric enzyme immunoassays: horseradish peroxidase, alkaline phosphatase or beta-galactosidase? J Immunol Methods 79, 27-37 (1985).

18 McLachlan, R., Coakley, J., Murton, L. & Campbell, N. Plasma intestinal alkaline phosphatase isoenzymes in neonates with bowel necrosis. J Clin Pathol 46, 654-659 (1993).

19 Uauy, R. D. et al. Necrotizing enterocolitis in very low birth weight infants: biodemographic and clinical correlates. National Institute of Child Health and Human Development Neonatal Research Network. J Pediatr 119, 630-638 (1991).

20 Pedregosa, F. V. G., Gramfort A, et al. Scikit-learn: Machine learning in {P}ython. J Mach Learn Res 12, 2825-2830 (2011).

21 Rish, I. An empirical study of the Naive Bayes Classifier IJCAI 2001 Work Empir Methods Artif Intell 22230, 41-46 (2001).

22 Shulman, R. J., Buffone, G. & Wise, L. Enteric protein loss in necrotizing enterocolitis as measured by fecal alpha 1-antitrypsin excretion. J Pediatr 107, 287-289 (1985).

23 Shifrin, D. A., Jr. et al. Enterocyte microvillus-derived vesicles detoxify bacterial products and regulate epithelial-microbial interactions. Curr Biol 22, 627-631, doi: 10.1016/j.cub.2012.02.022 (2012).

24 Mulivor, R. A., Hannig, V. L. & Harris, H. Developmental change in human intestinal alkaline phosphatase. Proc Natl Acad Sci USA 75, 3909-3912 (1978).

25 Vockley, J., Meyer, L. J. & Harris, H. Differentiation of human adult and fetal intestinal alkaline phosphatases with monoclonal antibodies. Am J Hum Genet 36, 987-1000 (1984).

26 Whitehouse, J. S. et al. The protective role of intestinal alkaline phosphatase in necrotizing enterocolitis. J Surg Res 163, 79-85, doi:10.1016/j.jss.2010.04.048 (2010).

27 Tuin, A. et al. Role of alkaline phosphatase in colitis in man and rats. Gut 58, 379-387, doi:10.1136/gut.2007.128868 (2009).

28 Sisley, A. C., Desai, T. R., Hynes, K. L., Gewertz, B. L. & Dudeja, P. K. Decrease in mucosal alkaline phosphatase: a potential marker of intestinal reperfusion injury. J Lab Clin Med 133, 335-341 (1999).

29 Ballance, W. A., Dahms, B. B., Shenker, N. & Kliegman, R. M. Pathology of neonatal necrotizing enterocolitis: a ten-year experience. J Pediatr 117, S6-13 (1990).

Example 4

Summary

Results from three different biochemical tests, performed on preterm infant stool, were grouped by post-conceptual age, which permits comparison of gut development of preterm infants through term infants. Measurement of relative iAP content in stool is a biomarker for bowel infection. Measurement of iAP activity is a biomarker for maturation of intestine in preterm infants. Measurement of fecal protein concentration is correlated with an intestinal inflammation response or diseased state.

Overview and Results

Necrotizing enterocolitis (NEC) is a multi-factorial disease that predominately affects premature infants and is the leading cause of late mortality and morbidity in very preterm infants (Caplan, 2008; Christensen et al, 2010). Although the etiology of NEC Is not clearly defined (Dominguez and Moss, 2012; Gephart et al., 2012), NEC is believed to represent a severe inflammatory disorder in the intestine (Balance et al., 1990; Zhang et al., 2011). Excessive inflammatory responses to environmental insults in the immature intestine are a hallmark of NEC (Chan et al., 2009). Specifically, increased levels of LPS/TLR4 signaling have been suggested to contribute to the pathogenesis of NEC (Chan et al., 2009; Fusunyan et al., 2001; Leaphart et al, 2007; Nanthakumar et al., 2011). Inhibition of LPS/TLR4 signaling attenuates intestinal inflammation and mitigates NEC pathology in animal models (Chan et al., 2009; Gribar et al., 2009).

Intestinal alkaline phosphatase (iAP) is a critical component of innate intestinal immunity. The enzyme, typically anchored to the intestinal brush border, cleaves phosphate groups, and as such can dephosphorylate lipopolysaccharides (LPS). LPS dephosphorylation inhibits a potent signaling pathway; thus, proinflammatory cytokines release and immune responses by LPS-activation of TLR4 (toll-like receptor 4; Lalles, 2010) are blocked by iAP. In addition, iAP is concentrated in specialized membrane vesicles, which are released from distal tips of enterocyte microvilli into the intestinal lumen (McConnell et al., 2009; Shilfrin et al., 2012). These released vesicles interact with and limit the proinflammatory potential of both bacteria and bacterial products.

Thus, we would expect that iAP would be measureable in human stool samples; this is confirmed from iAP being one of the core proteins in the human stool proteome. A steady state baseline of iAP would be detected from intestinal epithelial cells shed in the lumen and detected in stool. iAP content in stool would increase from released membrane vesicles loaded with iAP, if there was risk of bacteria-induced inflammation. Samples from non-NEC infants that were grouped by post-conceptual age (grey bars, FIG. 14A) showed the premature infants have low amounts of iAP, relative to a positive control from human small intestine tissue lysate. Our data also show that infants who have NEC have a high relative content of iAP (120-320% of positive control) in their stool samples at the time of clinical diagnosis.

Second, a dynamic transition of iAP isozyme forms is associated with the maturation of fetal intestine (Mulivor et al., 1978; Suriura et al., 1981). The fetal isoform of intestinal AP has a low biochemical activity, whereas the adult iAP has a high biochemical activity. We hypothesized that iAP activity would change with fetal development, i.e. preterm infants would have lower iAP activity than full-term infants. We reasoned that the limited iAP biochemical activity in neonates could lead to overactive LPS/TLR4 signaling. We tested this hypothesis by comparing stool iAP activities from infants of different gestational ages. Stool thus provides an accurate measurement of iAP activity in the neonatal intestine.

Figure 14:
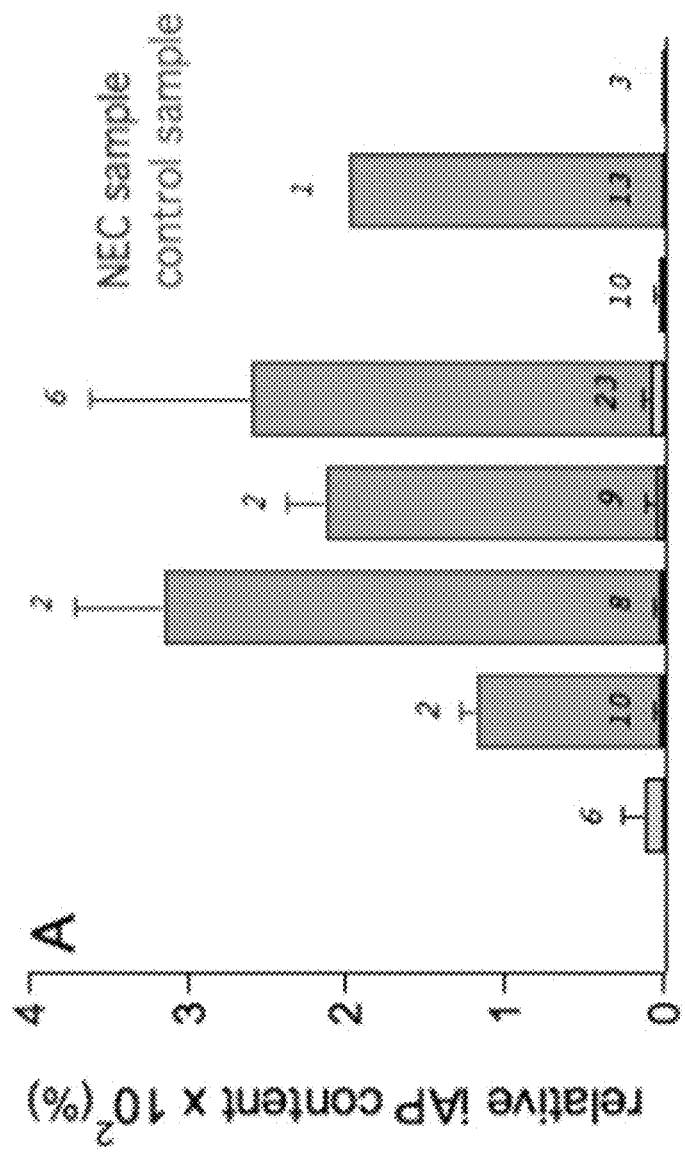
FIG. 14 shows relative iAP content, iAP activity, and protein concentration. NEC was classified according to the criteria of Bell et al. and modified by Walsh and Kliegman. For this analysis, the term 'suspected NEC' is stage I and the 'proven NEC' is stage II and more severe stages; the term 'perforated NEC' was used only to describe stage IIIB. Information from chart review was used to diagnose stage I. Radiographic determination of stage II required a record of pneumatosis intestinalis.

Our data indicate the premature infants have reduced iAP activity as compared to full-term infants. FIG. 14B shows average iAP activities, normalized to protein concentrations, of stool samples that are grouped by post-conceptual age (grey bars). There is a strong positive correlation between iAP activity and post-conceptual age. When comparing iAP activities spanning 24-41 weeks post-conceptual age, a one-way ANOVA and Tukey's multiple comparison test was performed and showed that the samples were statistically separated into two groups: the preterm group (post-conceptual age ≤35 weeks) and the full-term group (post-conceptual age ≥36 weeks). Comparison of all stool samples from full-term infants (post-conceptual age ≥36 weeks, n=28) with all samples from premature infants (post-conceptual age ≤35 weeks, n=79) revealed the latter group to have significantly lower iAP activities (p<0.0001; one-tailed t-test).

In comparison, infant stool collected on the same day of clinical NEC diagnosis (red bars) had much lower iAP activity, when compared to age-matched controls. Therefore, extremely low activity of iAP is correlated with NEC. Stool samples that have iAP activity below 240 U/mg can be used as a biomarker to identify infants at greatest risk for NEC. The sensitivity of this univariate biomarker is 100% with a 95% CI of 66-100%. The specificity is 100% with a 95% CI of 97-100%. For this sample set the disease prevalence is 7.8%, the positive predictive value is 100%, and the negative predictive value is 100%.

Without wishing to be bound by theory, the reduced capacity of preterm infant intestines to dephosphorylate proinflammatory LPS can increase the risk of excessive inflammatory responses to bacterial colonization and NEC development. Furthermore, based on these findings and without wishing to be bound by theory, prophylactic iAP supplementation to premature infants can warrant further study as a strategy for decreasing the risk of NEC. Our data also show that infants who have NEC have a high relative content of iAP and of protein in their stool samples at the time of clinical diagnosis.

Example 5

Feeding tolerance is demonstrated when the preterm infant is capable of safely ingesting and digesting the prescribed enteral (via mouth) feeding without complications associated with gastrointestinal dysfunction or infection. Clinical evidence of feeding tolerance in very low birth weight preterm infant is most often described in the literature as the number of days required to reach full-feeding volumes (reported ranged from 100-160 mL per kg per day), the number of episodes of feeding intolerance, the number of days feeds are withheld due to feeding intolerance symptoms, time to regain birth weight, lower leg growth, increase in weight gain, occipital-frontal head circumference, and length. None of the infants studied had reached full-feeding volumes.

Types of formula include, but are not limited to: EleCare (Abbott Nutrition), Neosure (Similac), EnfaCare (Enfamil), Pregestimil (Enfamil), Similac Special Care or SSC (Similac), and Gentlease (Enfamil).

Supplements can include without limitation Microlipid (Nestle Health Science).

Non-limiting examples of parenteral (or intravenous) nutrition comprise intravenous dextrose solutions, intravenous amino acid solutions, intravenous fat emulsions, intravenous vitamin and mineral supplements, or a combination thereof.

Example 6

NEC is a devastating GI disease that primarily affects premature infants (Incidence: 4-14%; Mortality: 15-30% (up to 50%); Morbidity: up to 50% of survivors). Clinical manifestations of NEC comprise abdominal distension, poor gastrointestinal motility, and bloody stools. X-ray findings comprise pneumatosis intestinalis and perforation.

Diagnosis of NEC is difficult because early manifestations are non-specific, the presence of pneumatosis intestinalis is inconsistent, and there is rapid clinical deterioration despite aggressive management. Pneumatosis, for example, is seen in only 48% of pathological confirmed necrotizing enterocolitis. There are currently no biochemical measures to identify those infants most at risk and to enable early diagnosis.

Figure 15:
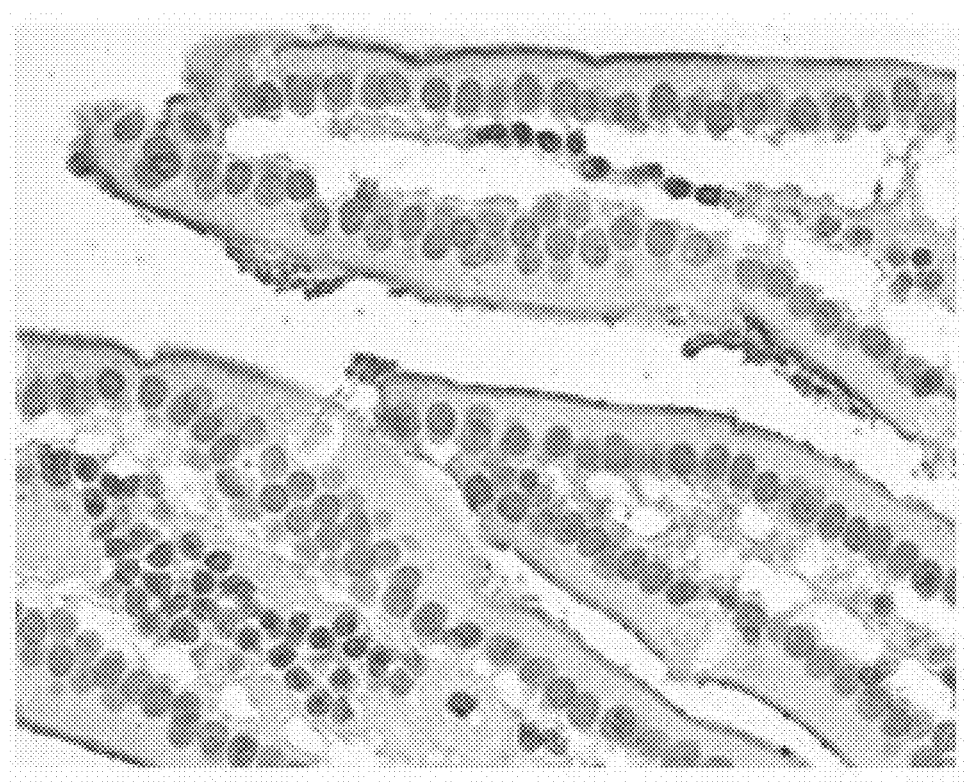
FIG. 15 shows immunohistochemical staining of intestinal tissue.
Figure 16:
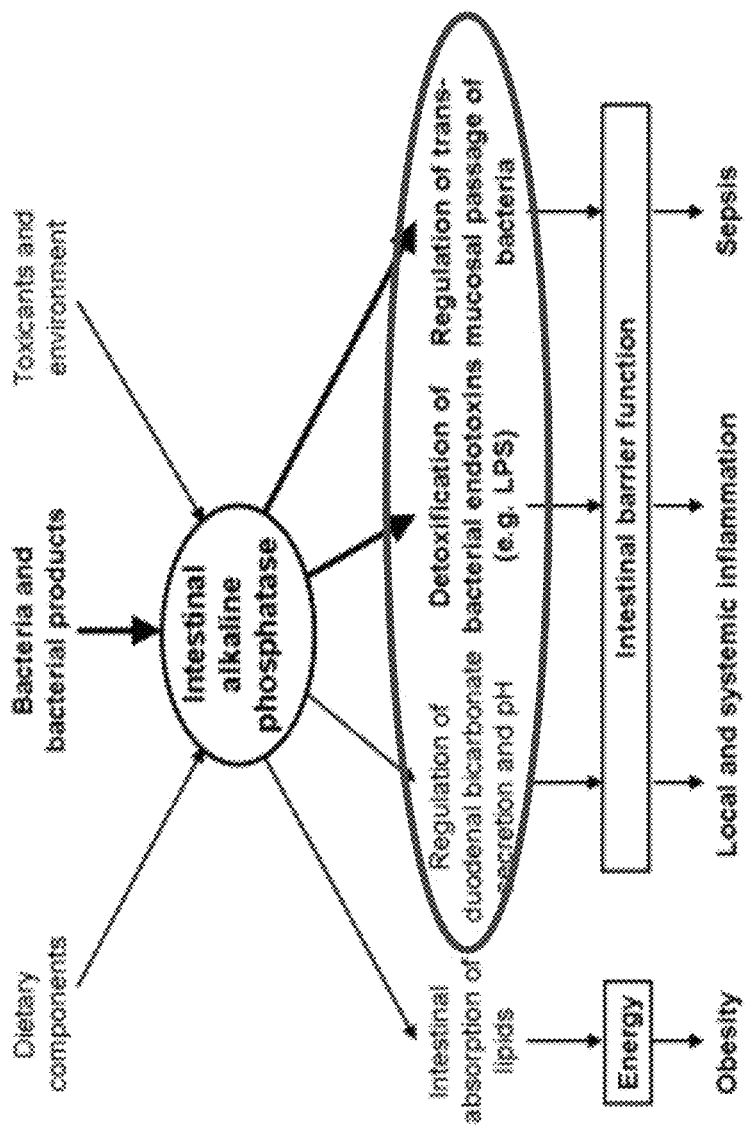
FIG. 16 shows schematic showing the many functions of iAP.

As described herein, intestinal alkaline phosphatase (iAP) can serve as a biomarker for NEC, and that deficiency of iAP is correlated with a predisposition to NEC.

iAP is produced by apical enterocytes and secreted into luminal brush border and catalyzes hydrolysis of phosphomonoesters. iAP is active as a homodimer and requires $Zn^{2+}$ and $Mg^{2+}$ ions in the active site. Substrates of iAP include LPS and nucleotide triphosphates. iAP has multiple roles affecting gut barrier function and inflammation. iAP is shed in stool. iAP is tissue specific AP, meaning made mostly in intestine, as demonstrated by immunohistochemical staining of intestinal tissue (FIG. 15).

iAP maintains gut barrier function (FIG. 16).

This study investigated whether fecal iAP is a diagnostic tool for NEC. Serial patient stool samples collected and processed within 4 days. Slurry of 200 mg stool/1 ml molecular grade water, Centrifugation at 14000 rpm at 4 degrees Celsius. Supernatants stored at −20 degrees Celsius until analysis. Biochemical Assays performed comprise concentration of total protein in stool, enzymatic activity of alkaline phosphatase, and western blot with human iAP. 16 infants from Touro Infirmary and Children's Hospital of New Orleans provided samples (NEC: 5 patients (25-35WGA); Non NEC: 11 Patients (23-34 WGA)). Over 100 stool samples processed and analyzed.

Figure 17:
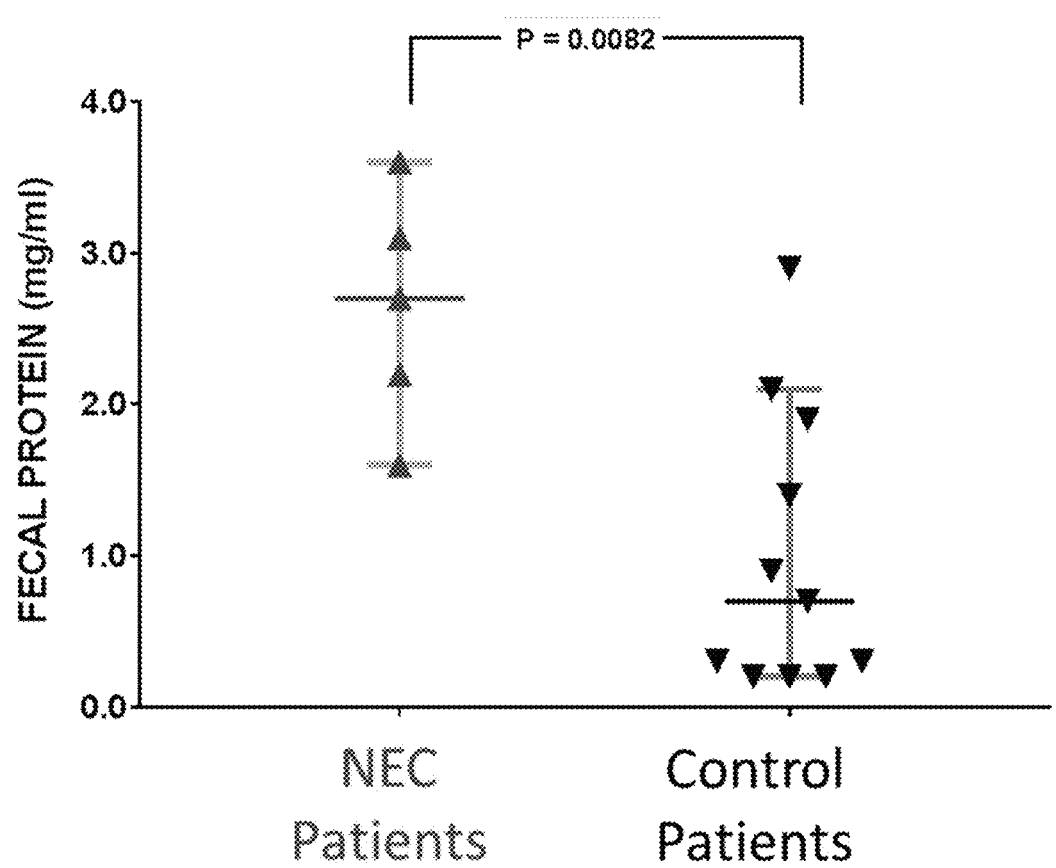
FIG. 17 shows fecal total protein content was higher in NEC patients than in control infants.

5 NEC patients at time of diagnosis were compared with 11 control patients, and the control patients fecal total protein between corrected gestational age 29-35 corresponding with the corrected gestational ages of the NEC patients was averaged. The results were statistically significant with median total fecal protein being 2.7 mg/ml in NEC patients and 0.7 mg/ml in Non NEC patients. Fecal total protein content was higher in NEC patients than in control infants (FIG. 17). The median (5%-95% CI) for Fecal Protein NEC 2.7 (1.6-3.6); Controls 0.7 (0.2-2.1).

The determination of fecal protein content requires ~1 hr of lab work. Measurement of fecal protein concentration above 2 mg/ml can serve as an early indicator of NEC onset.

Figure 18:
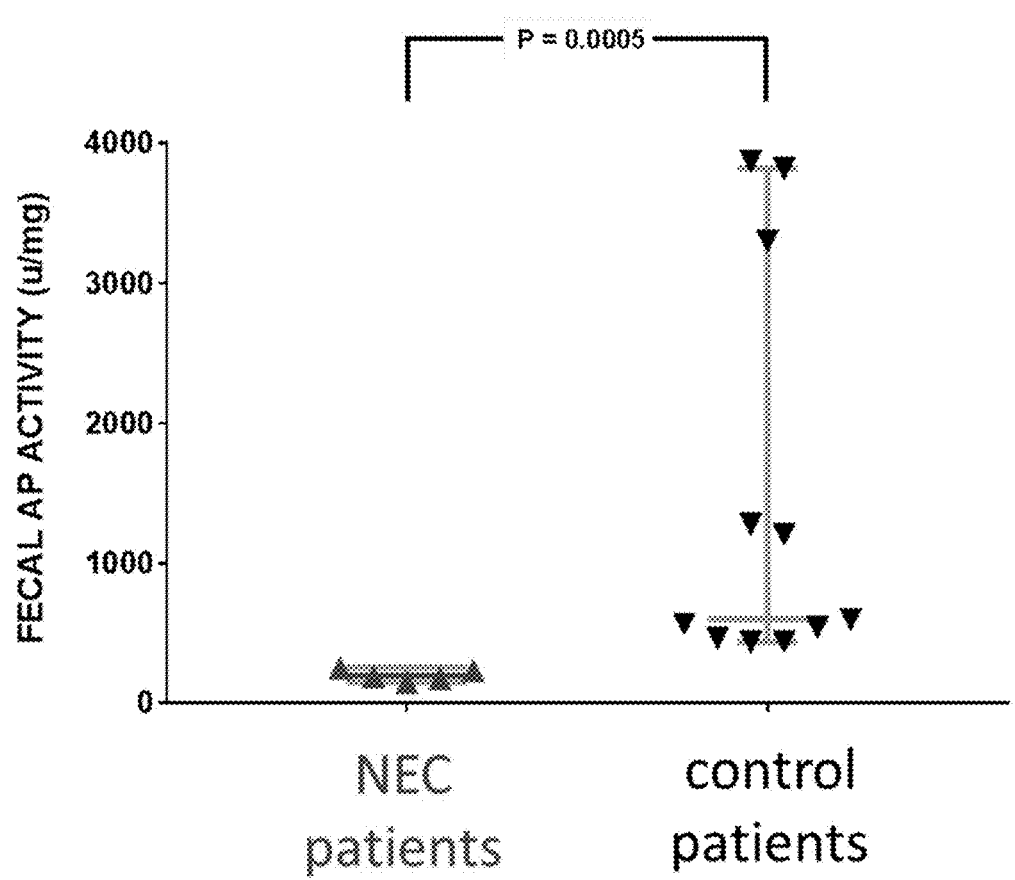
FIG. 18 shows fecal AP catalytic activity was consistently lower in NEC population.

Total fecal AP is predominantly intestinal isoform. There are other alkaline phosphatases in the intestine, such as bacterial and TNAP. We quantitated the proportion of intestinal AP catalytic activity from stool by using L-phenylalanine which specifically inhibits activity of only the intestinal type alkaline phosphatase. Specifically, we obtained AP activity with and without L-Phe added to determine specific iAP activity, and concluded that iAP is the main form of AP in stool. Fecal AP catalytic activity was consistently lower (statistically significant) in NEC population (FIG. 18).

TABLE 1

Median values 200 and 600.
Statistically significant difference
Summary of Data

| Parameter: | nec | controls |
|---|---|---|
| Mean: | 199.00 | 1501.6 |
| # of points: | 5 | 11 |
| Std deviation: | 42.279 | 1426.7 |
| Std error: | 18.908 | 430.17 |
| Minimum: | 146.00 | 434.00 |
| Maximum: | 250.00 | 3872.0 |
| Median: | 189.00 | 598.00 |
| Lower 95% CI: | 146.51 | 543.22 |
| Upper 95% CI: | 251.49 | 2460.1 |

Figure 19:
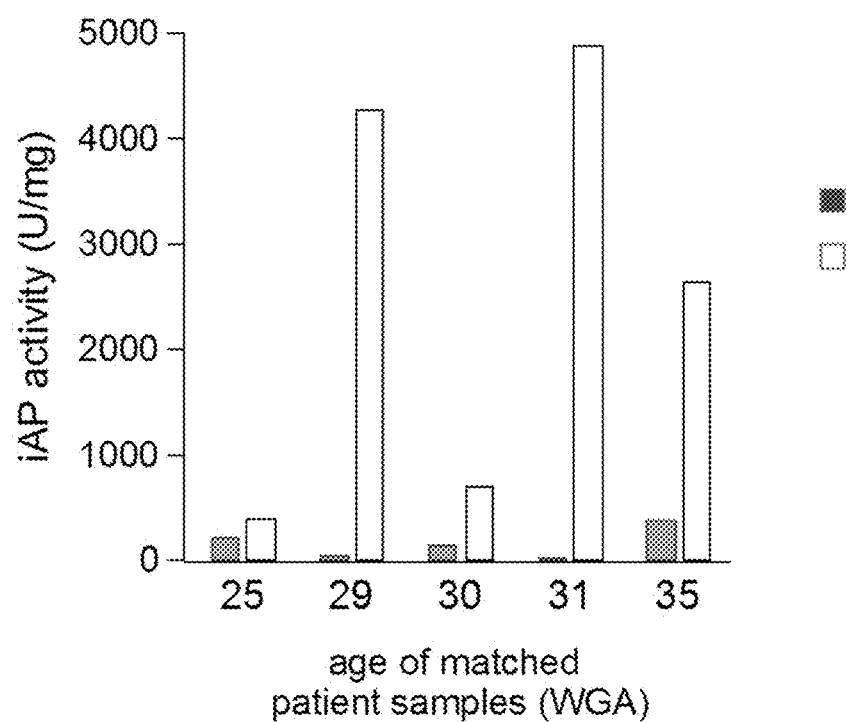
FIG. 19 shows AP enzyme activity at time of NEC diagnosis was always lower in matched patient samples.

When NEC patients were matched with a specific control of similar age and gestational age, the AP enzymatic activity was lower (FIG. 19).

Measurement of low AP activity (<200 U/mg) is a potential biomarker of NEC. There is a uniform reduction of alkaline phosphatase activity in NEC patients compared to matched controls. Without wishing to be bound by theory, iAP silencing can be a component of gut mucosal barrier dysfunction in critically-ill NEC patients. Goldberg et al. Proc Natl Acad Sci 105, 3551.

Figure 20:
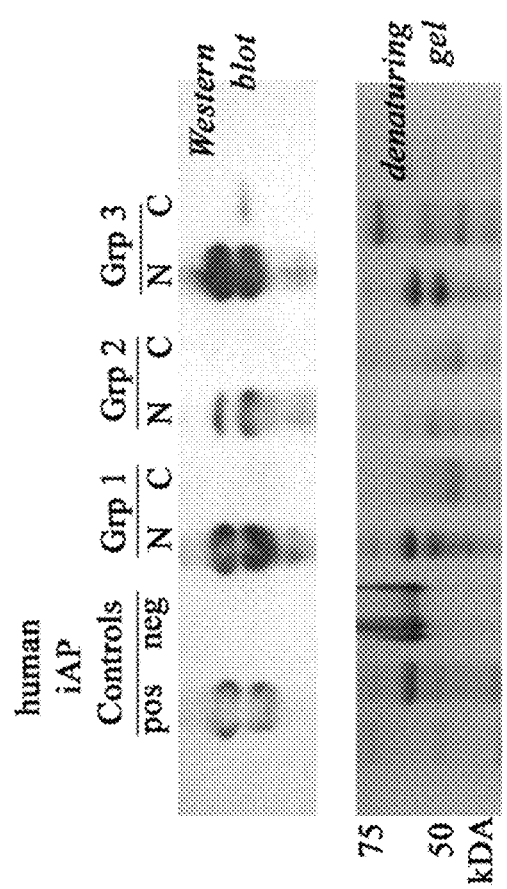
FIG. 20 shows high levels of iAP protein are detected in association with NEC.

Unexpectedly high levels of iAP protein are detected in association with NEC. A specific antibody for human iAP was used in western blot analyses and, surprisingly, detected appropriate signal only in the NEC samples (labeled N) and absent in control samples. Each group represents different NEC patients at the time of diagnosis and the controls which were age and gestational age matched. There are much higher iAP amounts present in stool of NEC patients at the time of diagnosis (FIG. 20).

Figure 21:
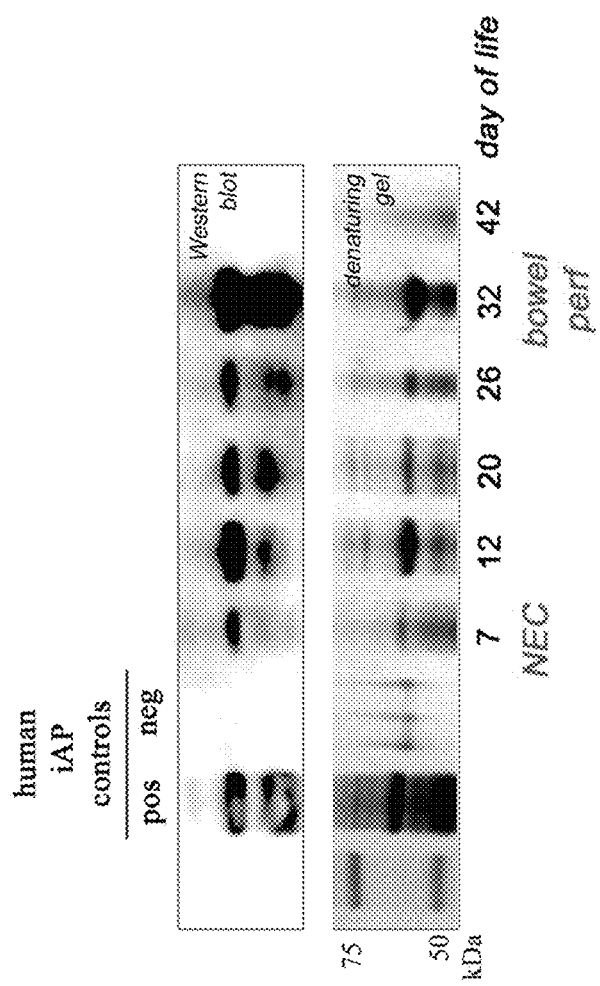
FIG. 21 shows increased fecal iAP protein levels in NEC episodes.
Figure 22:
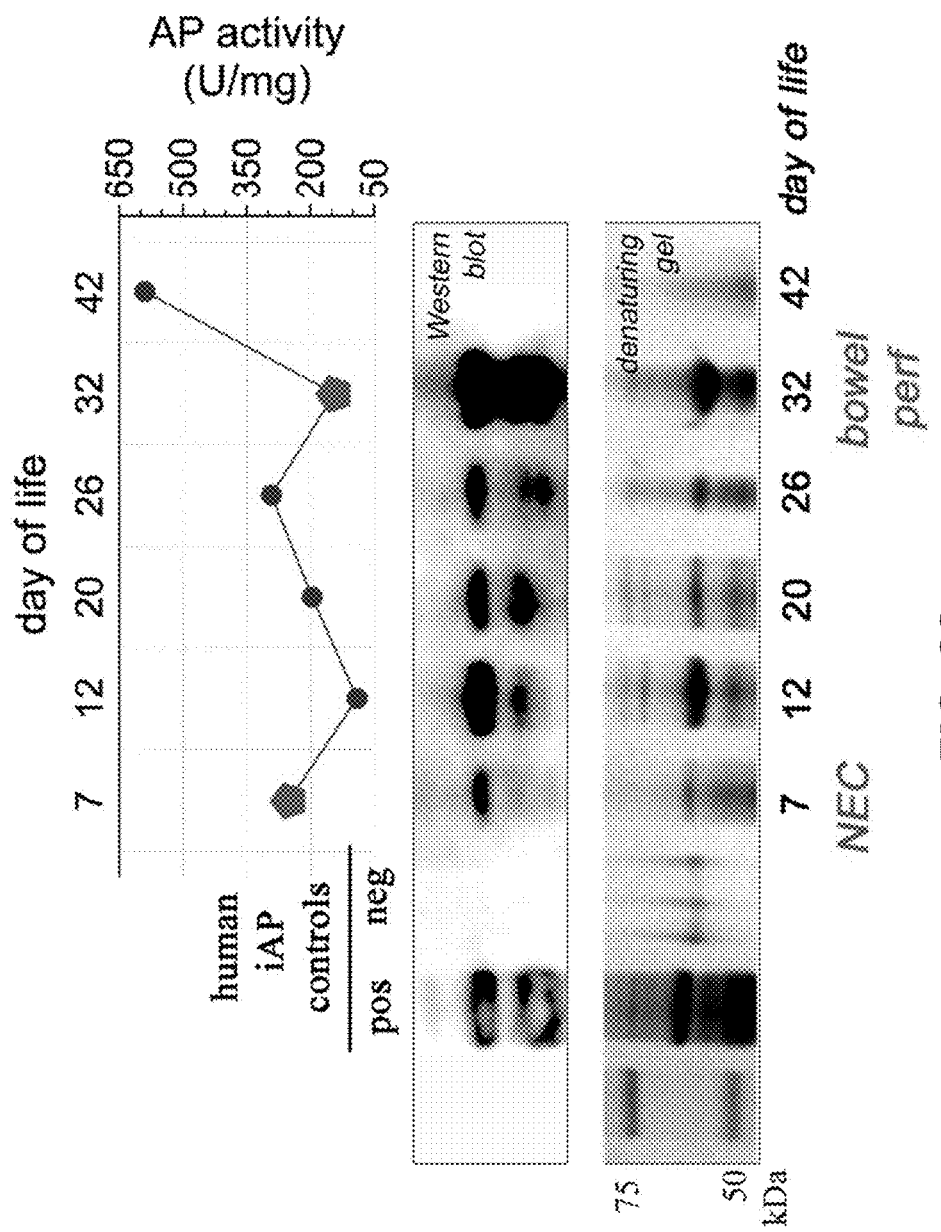
FIG. 22 shows increased iAP protein levels and decreased iAP enzyme activity in NEC episodes.

NEC episodes demonstrate increased fecal iAP protein levels. One NEC patient serially was followed and found that the patient continued to have high iAP levels even after medical management. The patient subsequently had a perforation followed by surgical intervention. Stool 10 days following surgery no longer has high levels of iAP protein. There is no signal on day 42 (FIG. 21). Contrasted with AP activity, the patient maintained lower AP activity until surgical intervention. 10 days after surgery AP activity begins to increase. The presence of persistent high fecal iAP levels and low activity could have been an indication of compromised bowel leading up to perforation. (FIG. 22).

iAP is developmentally regulated, and its expression and activity in rat models has been shown to be decreased in premature pups. Data corroborate iAP activity is decreased in human NEC infants, but not its expression. Without wishing to be bound by theory, a third NEC biomarker can be western blot analysis or ELISA of iAP protein levels in preterm infants (Rentea et al. Eur J Pediatr Surg 23, 39; Heinzerling et al. J Pediatr Surg 49, 954; Biesterveld et al. J Surg Res 196, 235).

This study provides preliminary evidence that three lab tests on stool samples can serve as biomarkers of NEC. Technique, length of time, and required equipment varies between the three tests. Combining the three markers can increase diagnostic value over using a single biomarker. Subsequent studies will optimize specificity and sensitivity of each method.

There are differences between proximal and distal halves of intestine in suckling rats. Structural differences comprise majority of iAP is membrane-bound in the proximal half of the intestine; in the ileum, however, iAP is found in the supernatant fraction of intestinal homogenate; in adults, more than 95% of iAP is membrane-associated. Functional differences comprise during suckling period, total alkaline phosphatase activity higher in ileum; when rat matures, activity falls in ileum and becomes higher in proximal bowel. Yedlin et al. J Biol Chem 256, 5620.

Figure 23:
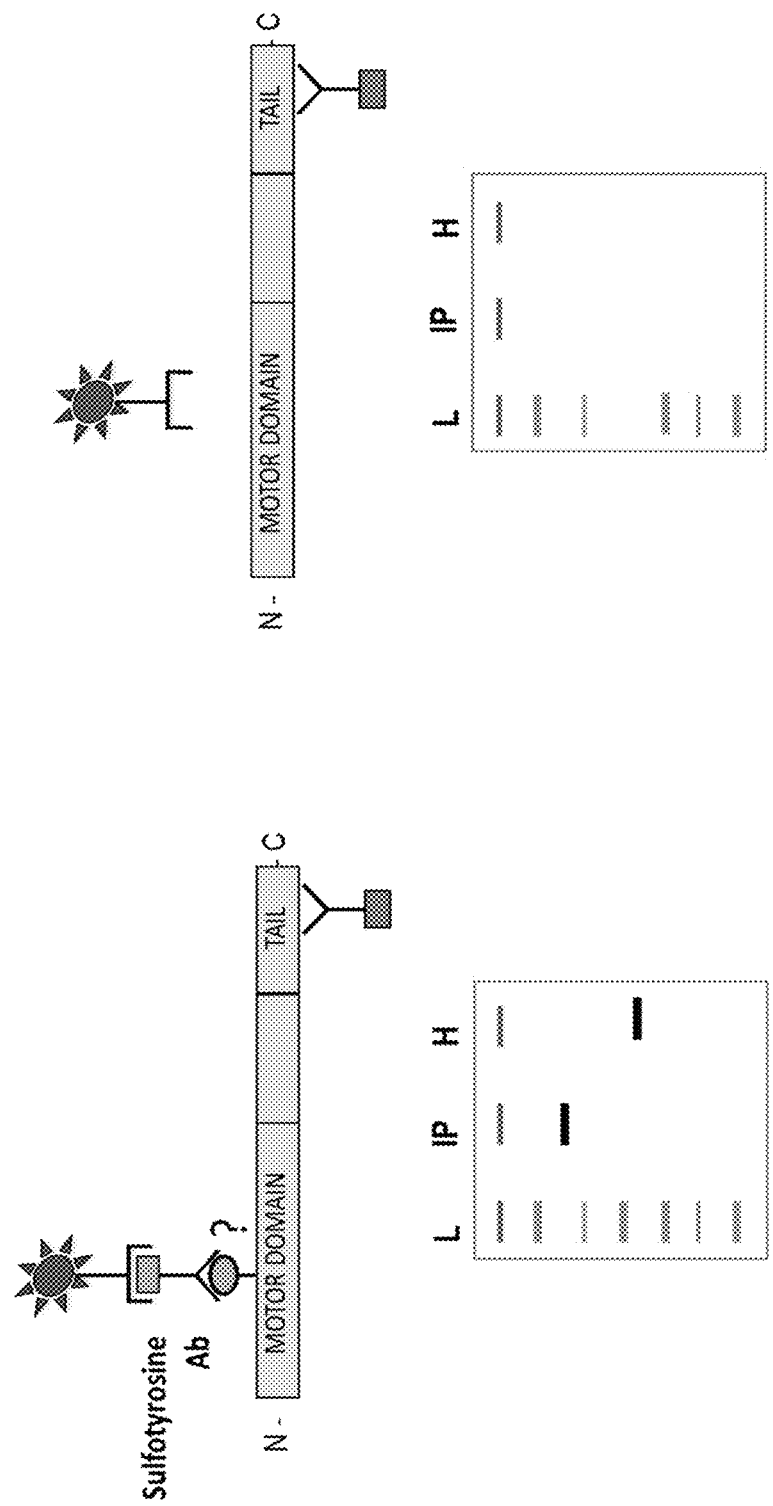
FIG. 23 shows a schematic for testing for non-specific binding of secondary antibody. Without being bound by theory, the enzyme assay can be conducted with just a secondary antibody conjugated with AP.
Figure 24:
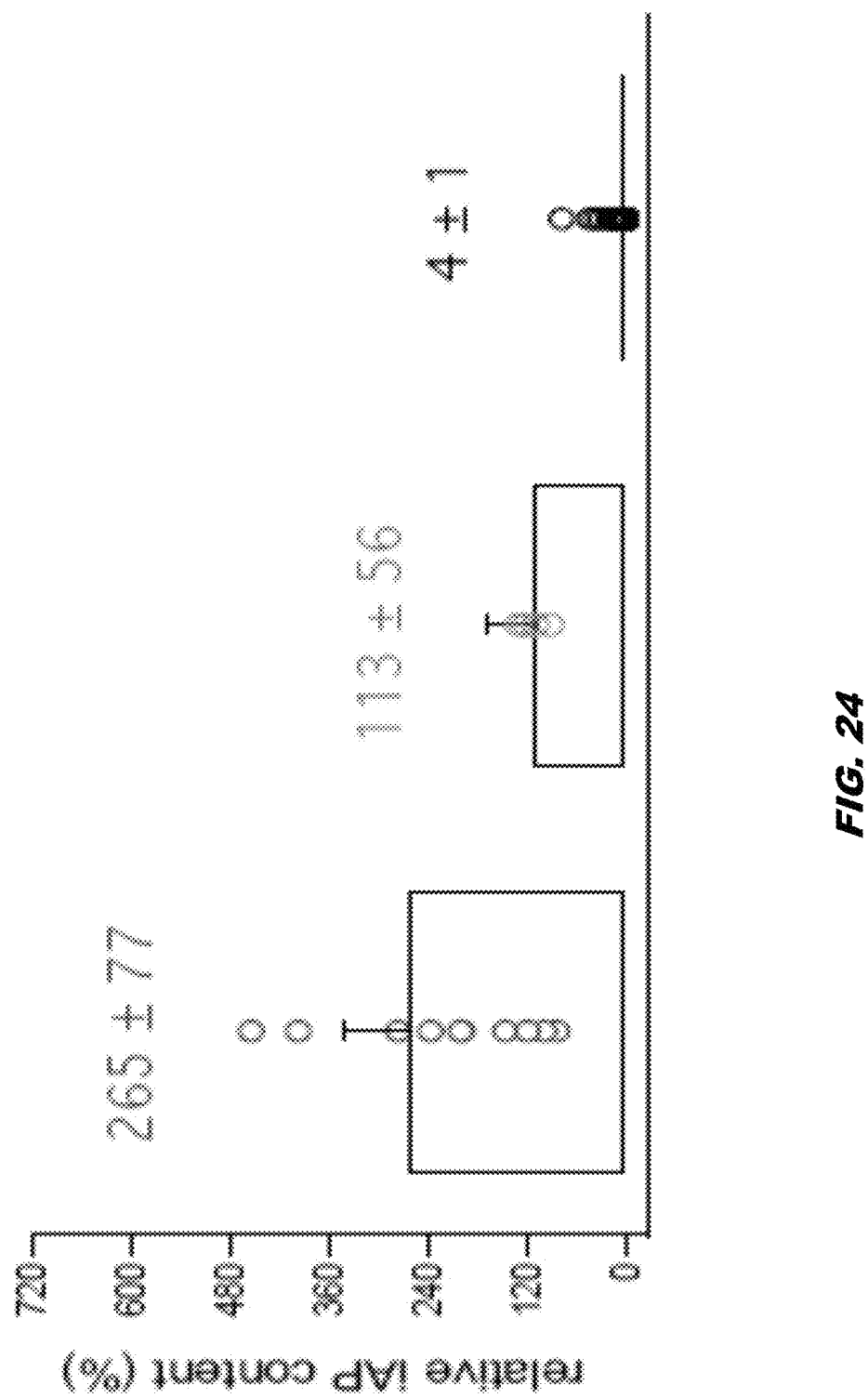
FIG. 24 shows clinical data that separates NEC diagnosis that matches X-ray and NEC suspicion (defined by neonatologists) and controls, demonstrating that the biomarker(s) can molecularly define NEC earlier.
Figure 25:
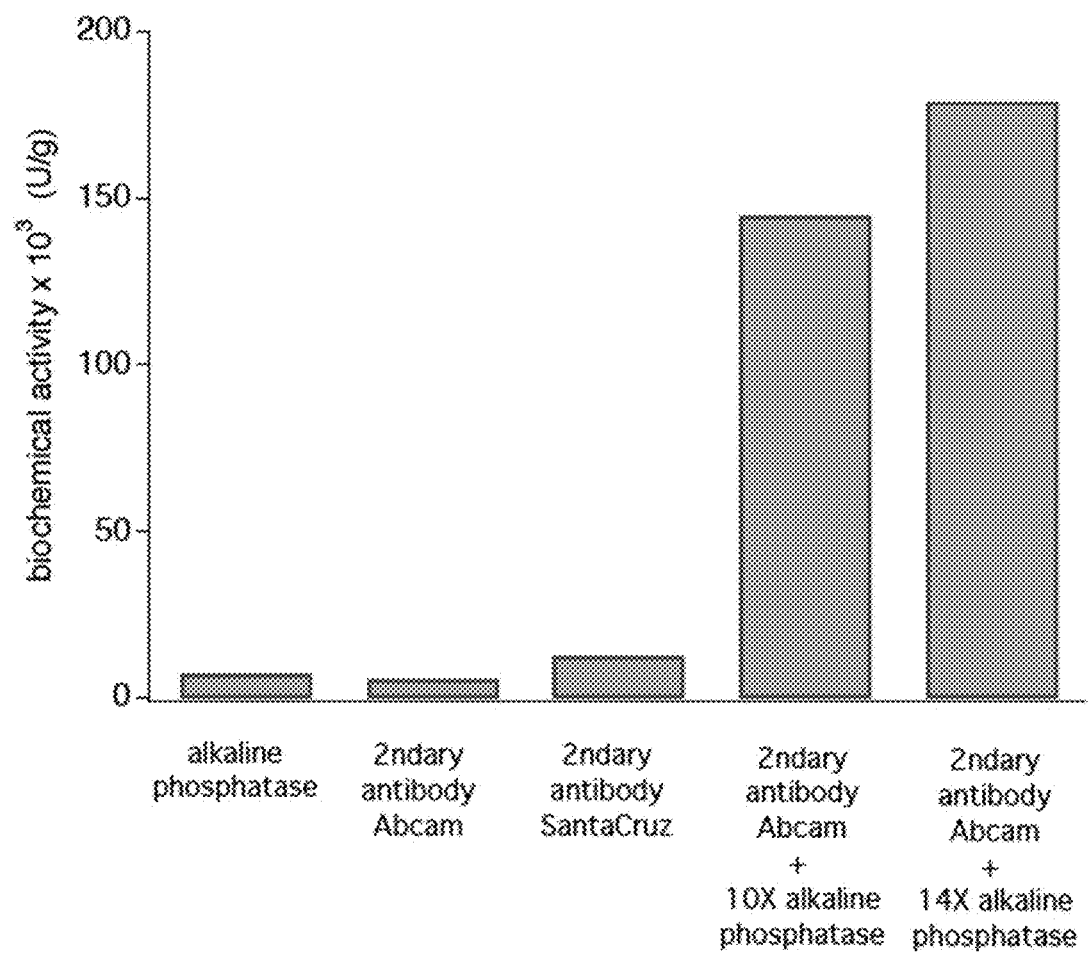
FIG. 25 is a bar graph showing that measurement of alkaline phosphatase can be confounded by signal from secondary antibodies. Isolated alkaline phosphatase can catalytically hydrolyze MUP to form the fluorescent product MU. Secondary antibodies, conjugated to AP, from two different commercial manufacturers can also hydrolyze MUP to form fluorescent product. When both alkaline phosphatase protein and the secondary antibody are in the same measurement, there is an increased level of catalytic activity observed. This can be monitored by both standard spectrophotometric readings of biochemical activity and by Western blot.

Testing for non-specific binding of secondary antibody (FIG. 23).

Methods: fluorimetric assays. Alkaline Phosphatase cleaves the phosphate group of the non-fluorescent 4-Methylumbelliferyl phosphate disodium salt (MUP) substrate; Results in an increased fluorescent signal when dephosphorylated; Measured using a spectrophotometer.

Example 7

Antibiotics for NEC

For NEC, 10-14 days of antibiotics is administrated to the infant, but the prescription is variable between hospital practices. Ideally, prescription would be for broad spectrum coverage for (i) gram-positive bacteria, (ii) gram-negative bacteria, and (iii) anaerobic bacteria. For example, Vancomycin (gram-positive including MRSA), ceftazidime (third generation cephalosporins—gram negative, some grant positive, and *Pseudomonas*), metronidazole (anaerobic coverage), oxacillin (gram positive).

Examples of general antibiotics regimes are: ampicillin+ gentamicin for possible vertically acquired infection from mother, and vancomycin+cetazidime for possible hospital acquired infections. Commonly used antibiotics are Gentamycin, Vancomycin, Ampicillin, Zosyn (combination of piperacillin and tazobactam), Flagyl (metronidazole generic), Clindamycin, Meropenem, Fluconazole (antifungal agent).

For sepsis, 7 days of antibiotics would be administered to the patient.

Feeding and Nutrition Regimens for Preterm Infants:

One of the challenging tasks for the neonatologist is to adequately and safely provide nutrition to very preterm infants. Enteral supply (feeding by mouth) is the most challenging balance of safety and nutrition. Signs for feed intolerance, or an inability to digest enteral feeds, is frequently encountered in preterm infants. Intolerance to enteral feeds can be a benign condition but there is overlap with necrotizing enterocolitis. Moreover, there are clear detrimental effects associated with fasting.

Complete parenteral nutrition (PN) solutions were provided on the first afternoon following birth. Infants receive stock solutions containing glucose (10 g/dL), amino acid (2.5 g/dL), and lipid s in the first 2 hours of life. Amino acid solutions contained AminosynPF10% (Hospira Inc) or TrophAmine 10% (B Braun Medical Inc). Intralipid 20% (Baxter) Liposyn III 20%, and Liposyn II 20% (Hospira Inc) provided parenteral lipids. Fluids typically provided 80 to 100 mL/kg per day at birth and increased by 20 mL/kg to 140-160 mL/kg per day in the first week of life. Acetate salts of sodium and potassium in PN solutions are buffers against metabolic acidosis.

PN solutions provided most of the nutrition in the first week of life. Enteral nutrition (EN) typically contributed only minimal energy until the end of the second week. The transition to exclusively EN was typically achieved before the end of the fourth week. When available, infants received their mother's breast milk. After tolerating breast milk at 150 mL/kg per day, infants received supplemental human milk fortifier (Mead-Johnson). When breast milk is not available, infants received formula specific for premature infants. The maximum caloric density of supplemented breast milk or formula was provided at 0.8 kcal/mL (80 kcal/dL; 24 kcal/oz).

Types of formula: Premature Enfamil Formula (Enfamil), EleCare (Abbott Nutrition), Neosure (Similac), EnfaCare (Enfamil), Pregestimil (Enfamil), Similac Special Care or SSC (Similac), Gentlease (Enfamil). Pregesternil and Elecare are hydrolyzed cow-based formulas, typically used for post-NEC babies or those with history of feeding intolerance. Enfacare and Neosure are discharge preterm formula Premature Enfamily Formula and Similac Special Care are hospital premature formula.

Feeding tolerance is demonstrated when the preterm infant is capable of safely ingesting and digesting the prescribed enteral feeding without complications associated with gastrointestinal dysfunction or infection. Clinical evidence of feeding tolerance in very low birth weight preterm infant is most often described in the literature as the number of days required to reach full-feeding volumes (reported ranged from 100-160 mL per kg per day), the number of episodes of feeding intolerance, the number of days feeds are withheld due to feeding intolerance symptoms, time to regain birth weight, lower leg growth, increase in weight gain, occipital-frontal head circumference, and length.

Proposed prevention/treatment strategies for feeding intolerance in preterm infants include:

TABLE 2

Proposed prevention/treatment strategies for feeding intolerance in preterm infants.

| Altered/immature function | Prevention/treatment strategy |
|---|---|
| 1. Motility | |
| a. Sucking-swallowing coordination | Non nutritive sucking<br>Tube Feeding:<br>I. Gastric vs transpyloric<br>II. Continuous vs intermittent bolus |
| b. Gastro-esophageal reflux | Infant positioning<br>Prevention/treatment of apnoeic episodes<br>Drugs:<br>I. Acid suppressors<br>II. prokinetics |
| c. Gastric emptying | Low fat content<br>Osmolality (?)<br>Prokinetic drugs |

TABLE 2-continued

Proposed prevention/treatment strategies for feeding intolerance in preterm infants.

| Altered/immature function | Prevention/treatment strategy |
|---|---|
| d. Intestinal motility | Prokinetic drugs<br>Osmotic solutions<br>Enemas<br>Abdominal massage (?) |
| 2. Digestion | |
| a. Lactose | Lactose free formula<br>Lactase-treated formula |
| b. Protein | Hydrolysed protein formula<br>Amino acid-based formula |
| c. Fat | MCT/LcPUFA content |
| 3. "Intestinal millieu" | |
| a. Microflora | Probiotics<br>Prebiotics<br>Lactoferrin |
| b. Intestinal barrier | Glutamine<br>Probiotics<br>Lactoferrin |

REFERENCES CITED IN THIS EXAMPLE

Herrmann and Herrman. 2010. Nutrition in Clinical Practice 25, 69-75

Fanaro. 2013. Early Human Development 89, S13-S20

Example 8

PROP=propensity of getting NEC=(1−activity)*WB

1. The Markov transition model was fitted with PROP, white blood cell count, antibiotic (Yes/No), and whether or not a baby had some volume of food (>0).

TABLE 3

| Variable | Coefficient + Confidence Interval | |
|---|---|---|
| | Transition to NEC | Transition to Non-NEC |
| PROP | 18.7845 (1.302252, 270.9) | 0.1038 (0.006116, 1.76) |
| White Blood Cell Count | 0.9975 (0.9777, 1.018) | 0.9726 (0.9246, 1.023) |
| Antibiotics | 0.5051 (0.1323, 1.928) | 11.9612 (3.8391, 37.267) |
| Volume Given > 0 | 1.1571 (0.3602, 3.717) | 0.8028 (0.2958, 2.179) |

Volume given = 0

Without being bound by theory, increased PROP significantly increases the risk of transitioning to NEC. Without wishing to be bound by theory, using Antibiotics increases the probability of transitioning to non-NEC from NEC status.

Without wishing to be bound by theory, when the data from the table are plotted, there is a symmetry relationship between the state 1 to 2 and the state 2 to 1 ratios.

For example, using the data set without the extra assay data from 2019, the coefficient for PROP was around 11 or 12.

The result printouts are below:

Maximum likelihood estimates
Baselines are with covariates set to their means
Transition intensities with hazard ratios for each covariate

|  | Baseline | PROP |
|---|---|---|
| State 1-State 1 | −0.01257 (−0.03220, −0.00491) | |
| State 1-State 2 | 0.01257 (0.00491, 0.03220) | 18.7845 (1.302252, 270.96) |
| State 2-State 1 | 1.22270 (0.43181, 3.46219) | 0.1038 (0.006116, 1.76) |
| State 2-State 2 | −1.22270 (−3.46219, −0.43181) | |
|  | ANTIBIOTICS | |
| State 1-State 1 | | |
| State 1-State 2 | 0.9975 (0.9777, 1.018) | 0.5051 (0.1323, 1.928) |
| State 2-State 1 | 0.9726 (0.9246, 1.023) | 11.9612 (3.8391, 37.267) |
| State 2-State 2 | | |
|  | VOL1TRUE | |
| State 1-State 1 | | |
| State 1-State 2 | | 1.1571 (0.3602, 3.717) |
| State 2-State 1 | | 0.8028 (0.2958, 2.179) |
| State 2-State 2 | | |

Using additional variables (IT ratio, Platelet count, Time) resulted in models that did not converge. Without wishing to be bound by theory, this may be due to the fact that observations are carried forth to days where we have missing values. For example, if it is known on Tuesday that a baby has a PROP score of 0.05 on a Monday, and another PROP value is not obtained until Thursday, the baby's PROP values on Tuesday and Wednesday are 0.05.

2. In embodiments, certain variables can be removed, for example if the model is complicated and the preliminary data is limiting. When it comes to predicting a transition into NEC status, a significant variable is PROP (since the confidence interval doesn't contain 1). Without wishing to be bound by theory, if a model is fitted with only this term, the table is as follows:

TABLE 4

|  | Coefficient + Confidence Interval | |
|---|---|---|
| Variable | Transition to NEC | Transition to Non-NEC |
| PROP | 52.5438 (5.51, 500.99) | 0.2727 (0.012, 6.01) |

In another embodiment, antibiotics is left in the analysis, which seem to be significantly related with a switch from NEC to non-NEC status. Without wishing to be bound by theory, in this case, the table is as follows:

|  | Coefficient + Confidence Interval | |
|---|---|---|
| Variable | Transition to NEC | Transition to Non-NEC |
| PROP | 24.12 (1.85, 313.85) | 0.137 (0.0079, 2.38) |
| Antibiotics | 0.3871 (0.126, 1.19) | 10.52 (3.59, 30.81) |

3. FIT of linear mixed model for PROP score

Next, a linear mixed model was run to predict PROP score as a function of ONLY the values currently in possession (i.e. we did not impute values of PROP by carrying one forward) over time. This resulted in 580 datapoints for 92 patients, with about 45 (7%) of these datapoints containing PROP values corresponding to patients with a NEC diagnosis at that time. This model was fit for only the covariates NEC, Antibiotics (YES/NO) and Volume fed >0 (NO/YES) since introducing more covariates dropped the complete cases to 78 datapoints. A linear and quadratic time effect was initially included, but, without being bound by theory, the likelihood ratio test showed that this was not necessary. The results of the reduced model without a time effect is below:

|  | Coef | S.E. | t | Pr(>|t|) |
|---|---|---|---|---|
| Intercept | −0.0636 | 0.0178 | −3.57 | 0.0004 |
| NEC | 0.0733 | 0.0149 | 4.93 | <0.0001 |
| ANTI | 0.0074 | 0.0086 | 0.86 | 0.3876 |
| VOL1 | 0.0502 | 0.0128 | 3.92 | 0.0001 |

In additional embodiments, having the explicit mathematical terms may allow analysis of data from the linear mixed model.

Without wishing to be bound by theory, mixed models are used for analysis of correlated data, such as longitudinal data or information that may have multiple dependencies. A key feature of mixed models is that, by introducing random effects in addition to fixed effects, they allow for addressing multiple sources of variation, i.e. within- and between-subject variation, and interactions between combinations of discrete and continuous variables. In an embodiment, the 't' in the information in Example 8 can refer to an abbreviation for time. In this embodiment, NEC PROP may be able to predict disease 4.93 days prior to x-ray.

As described herein, if a patient is diagnosed with NEC on a given day, it can be predicted that they will have a significantly higher PROP score, as the NEC coefficient is positive (0.0733) and the p value is less than 0.0001. There is an interaction between NEC Prop and no feeds; the Vol1 coefficient is 0.0502. This interaction is significant, as it has a p value of 0.0001. Without wishing to be bound by theory, such an interaction would be expected, since the medical staff halt feeds when NEC is diagnosed. Antibiotic use has no associative interaction with NEC propensity. This mixed model accounts for multiple observations on each interval over time.

Example 9

Without wishing to be bound by theory, PROP Score can be a function of iAP activity and WB value:

$$Prop_i = \left(1 - \frac{iAP_{Activity_i}}{\max(iAP_{Activity_i})}\right) \frac{WB_i}{\max(WB)}$$

Transition Model:

Does increased PROP increase (decrease) the rates of transition A and B?

A. PROP Only

In an embodiment, the analysis carried forth the patient's PROP score to days that did not have data. For example, if a patient had a PROP score from day 3 and 7, then their PROP score from days 4-6 are equal to that at day 3.

TABLE 5

| Variable | Coefficient + Confidence Interval | |
|---|---|---|
| | Transition to NEC | Transition to Non-NEC |
| PROP | 52.5 (5.51, 501) | 0.273 (0.01, 6.01) |

Increased PROP was associated with a significantly increased transition risk to NEC suspicion/(+).

B. PROP and Antibiotics

The same carry forward was done with the antibiotics, only considering whether or not the baby was on antibiotics, without considering what kind of antibiotics. for example.

TABLE 6

| Variable | Coefficient + Confidence Interval | |
|---|---|---|
| | Transition to NEC | Transition to Non-NEC |
| PROP | 24.1 (1.85, 314) | 0.14 (0.01, 2.38) |
| Antibiotics | 0.39 (0.13, 1.19) | 10.52 (3.59, 30.8) |

Increased PROP was associated with an increased risk of transition to NEC. Antibiotics increased the probability of transitioning from NEC to NEC(−).

C. Full Model

TABLE 7

| Variable | Coefficient + Confidence Interval | |
|---|---|---|
| | Transition to NEC | Transition to Non-NEC |
| PROP | 18.8 (1.30, 271) | 0.10 (0.01, 1.76) |
| White Blood Cell Count | 1.00 (0.98, 1.02) | 0.97 (0.92, 1.02) |
| Antibiotics | 0.51 (0.13, 1.93) | 12.0 (3.84, 37.3) |
| Volume Given = 0 | 1.16 (0.36, 3.72) | 0.80 (0.30, 2.18) |

In the referenced embodiment, additional covariates could not be considered due to convergence issues.

White blood cell counts were carried forward, as was whether the patient had not received food.

After adjusting for white blood cell count and whether or not the patient received food, the results demonstrate that PROP and antibiotics are significant predictors of transition risks.

Figure 26:
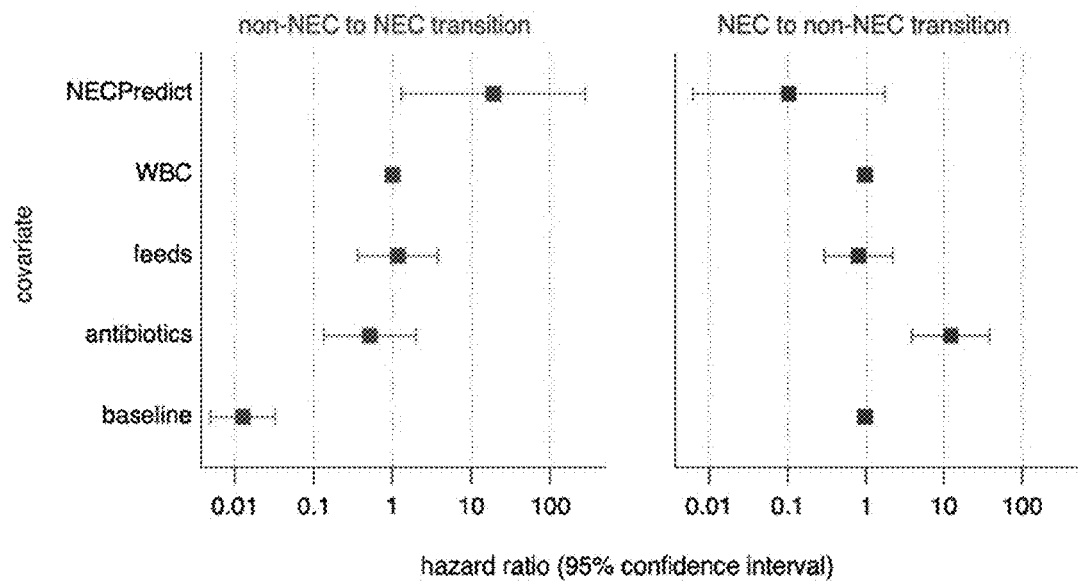
FIG. 26 shows the risk of non-NEC to NEC transition and NEC to non-NEC transition.
Figure 27:
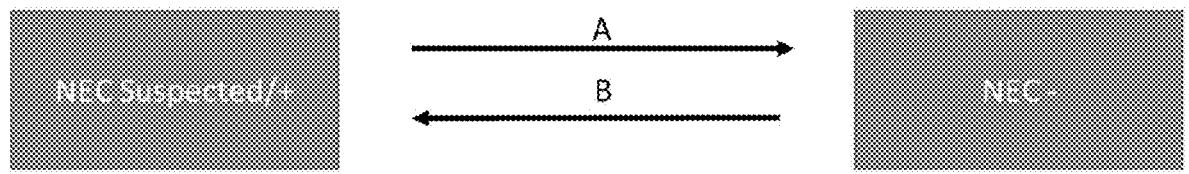
FIG. 27 shows a schematic of a Transition Model.

Data shows partial symmetry with that in FIG. 26.

Interval overlap with 1 infers no significant difference.

Linear Mixed Model for PROP Score

It is noted that we did not carry any points further; thus, without wishing to be bound by theory, we used observed 580 PROP datapoints on 92 patients Model Fits:

$$PROP_{ij} = a_1 NEC_{ij} + a_2 ANTI_{ij} + a_3 VOL0_{ij} + a_4 t_{ij} + a_5 t_{ij}^2 + b_i$$

$PROP_{ij}$ is the prop score of patient i at the jth measurement.

$t_{ij}$ is the time (in PCA days) of the jth measurement for patient i.

Time and Time^2 were not needed in the regression model.

TABLE 8

| Variable | Coefficient | Test Statistic | P-value |
|---|---|---|---|
| Nec+ | .0733 | 4.93 | <.0001 |
| Antibiotics | .0074 | .086 | .3876 |
| Volume = 0 | .0502 | 3.92 | .0001 |

NEC associated with a significant increase in PROP score.

Without wishing to be bound by theory, being fed no food on a given day associated with a significant increase in PROP score.

Without wishing to be bound by theory, assumed normality for PROP.A beta regression had mixed effects modeling capabilities.

Using beta regression without mixed effects, the same results are obtained

Embodiments could use Bayesian methods to fit the beta-mixed regression if desired

EQUIVALENTS

Those skilled in the art will recognize, or be able to ascertain, using no more than routine experimentation, numerous equivalents to the specific substances and procedures described herein. Such equivalents are considered to be within the scope of this invention, and are covered by the following claims.

What is claimed:

1. A method of identifying an infant afflicted with early-stage necrotizing enterocolitis, the method comprising:
   detecting the presence of at least one early-stage necrotizing enterocolitis biomarker in a stool sample from the infant,
   wherein the early-stage necrotizing enterocolitis biomarker comprises increased iAP protein level compared with age-matched controls, increased total protein level compared with age-matched controls, or a combination thereof,
   wherein the early-stage necrotizing enterocolitis biomarker is indicative of infant afflicted with early-stage necrotizing enterocolitis; and
   treating the infant afflicted with early-stage necrotizing enterocolitis, wherein treating comprises administering an effective amount of an antibiotic, a probiotic, an intravenous fluid, an iAP replacement composition, a small molecule effector of catalytic activity, an anti-inflammatory agent, parenteral or intravenous nutrition, a biologic, or a prebiotic; withholding oral feeding; surgery; or a combination thereof.

2. The method of claim 1, further comprising diagnosing the infant as having early-stage necrotizing enterocolitis if the total protein level in the sample is greater than about 1.0 mg/ml, if the level of iAP protein is greater than 10.7% of a positive control sample, or a combination thereof.

3. A method for screening the presence of an early-stage necrotizing enterocolitis signature, the method comprising:
   detecting the presence of at least one early-stage necrotizing enterocolitis biomarker in a stool sample from an infant, wherein the early-stage necrotizing enterocolitis biomarker comprises increased iAP protein level compared with age-matched controls, increased total protein level compared with age-matched controls, or a combination thereof, thereby providing a necrotizing enterocolitis signature that is indicative of necrotizing enterocolitis; and
   treating the infant afflicted with necrotizing enterocolitis, administering an effective amount of an antibiotic, a probiotic, an intravenous fluid, an iAP replacement composition, a small molecule effector of catalytic activity, an anti-inflammatory agent, parenteral or intravenous nutrition, a biologic, or a prebiotic; withholding oral feeding; surgery; or a combination thereof.

4. The method of claim 3, wherein the early-stage necrotizing enterocolitis biomarker is total protein level in the sample greater than about 1.0 mg/ml, iAP protein greater than 10.7% of a positive control sample, or a combination thereof.

5. A method for determining the prognosis of an infant afflicted with necrotizing enterocolitis, the method comprising:
   detecting the presence of at least one necrotizing enterocolitis biomarker in a stool sample from the infant, wherein the necrotizing enterocolitis biomarker comprises increased iAP protein level compared with age-matched controls, increased total protein level compared with age-matched controls, or a combination thereof, thereby providing a necrotizing enterocolitis signature that is indicative of necrotizing enterocolitis;
   comparing the presence of the at least one necrotizing enterocolitis biomarker to a reference level of the at least one necrotizing enterocolitis biomarker; and
   determining a prognosis for the infant, wherein a poor prognosis is indicated by an increase of iAP protein level compared to a positive control sample, increased total protein level compared with age-match controls, or a combination thereof.

6. The method of claim 5, wherein the method is carried out prior to administering an anti-NEC treatment to the infant.

7. The method of claim 5, further comprising identifying the infant as likely to benefit from administration of an anti-NEC treatment when the patient is determined to have an increase of iAP protein level compared with an age-matched control, an increased total protein level compared with an age-matched control, or a combination thereof.

8. The method of claim 5, further comprising treating the infant, wherein treating comprises administering an effective amount of an antibiotic, a probiotic, an intravenous fluid, an iAP replacement composition, a small molecule effector of catalytic activity, an anti-inflammatory agent, parenteral or intravenous nutrition, a biologic, or a prebiotic; withholding oral feeding; surgery; or a combination thereof.

9. The method of any one of claims 1, 3, or 5, wherein the infant is a premature infant.

10. The method of any one of claims 1, 3, or 5, wherein the detecting comprises performing an assay to determine total protein level, intestinal alkaline phosphatase protein level, or a combination thereof in the sample.

11. The method of claim 10, wherein the assay comprises an immunoassay, a colorimetric assay, a fluorimetric assay, a radioisotope assay, or a combination thereof.

12. The method of claim 11, wherein the immunoassay comprises a western blot assay, an enzyme-linked immunosorbent assay (ELISA), immunoprecipitation or a combination thereof.

13. The method of claim 1, 3, or 5, further comprising incubating the biological sample with an agent that binds intestinal alkaline phosphatase (iAP).

14. The method of claim 13, wherein the agent comprises an anti-iAP antibody or an anti-AP antibody.

15. The method of claim 10, wherein the assay comprises a kinetic assay or endpoint assay.

16. The method of claim 15, wherein the kinetic assay comprises 4-methylumbelliferyl phosphate, p-Nitrophenyl phosphate, an assay to detect ATP hydrolysis or its products, or a combination thereof.

17. The method of claim 1, 3, or 5, wherein the necrotizing enterocolitis biomarker further comprises decreased iAP enzymatic activity compared with age-matched controls.

18. The method of claim 17, further comprising diagnosing the infant as having necrotizing enterocolitis if the iAP enzymatic activity is lower than about 979 mU/mg.

19. The method of claim 17, wherein the detecting comprises an assay to determine intestinal alkaline phosphatase enzyme activity.

* * * * *